United States Patent
Bonda et al.

(10) Patent No.: US 9,867,800 B2
(45) Date of Patent: Jan. 16, 2018

(54) METHOD OF QUENCHING SINGLET AND TRIPLET EXCITED STATES OF PIGMENTS, SUCH AS PORPHYRIN COMPOUNDS, PARTICULARLY PROTOPORPHYRIN IX, WITH CONJUGATED FUSED TRICYCLIC COMPOUNDS HAVE ELECTRON WITHDRAWING GROUPS, TO REDUCE GENERATION OF REACTIVE OXYGEN SPECIES, PARTICULARLY SINGLET OXYGEN

(71) Applicant: HALLSTAR INNOVATIONS CORP., Chicago, IL (US)

(72) Inventors: Craig A. Bonda, Winfield, IL (US); Shengkui Hu, Darien, IL (US)

(73) Assignee: Hallstar Innovations Corp., Chicago, IL (US)

( * ) Notice: Subject to any disclaimer, the term of this patent is extended or adjusted under 35 U.S.C. 154(b) by 0 days.

(21) Appl. No.: 13/805,168

(22) PCT Filed: Dec. 3, 2012

(86) PCT No.: PCT/US2012/067519
§ 371 (c)(1),
(2) Date: Dec. 18, 2012

(87) PCT Pub. No.: WO2014/025370
PCT Pub. Date: Feb. 13, 2014

(65) Prior Publication Data
US 2015/0164852 A1 Jun. 18, 2015

Related U.S. Application Data

(60) Provisional application No. 61/681,916, filed on Aug. 10, 2012.

(51) Int. Cl.
*A61K 31/277* (2006.01)
*A61K 8/40* (2006.01)
(Continued)

(52) U.S. Cl.
CPC ............ *A61K 31/277* (2013.01); *A61K 8/40* (2013.01); *A61K 8/46* (2013.01); *A61K 8/494* (2013.01);
(Continued)

(58) Field of Classification Search
CPC ........ A61K 31/277; A61K 8/40; A61K 8/498; A61K 8/4986; A61K 17/04; A61K 31/382;
(Continued)

(56) References Cited

U.S. PATENT DOCUMENTS 3,218,166 A    11/1965    Reitter
3,408,187 A    10/1968    Mammino
(Continued)

FOREIGN PATENT DOCUMENTS

CN    101233191    7/2008
CN    101302219    11/2008
(Continued)

OTHER PUBLICATIONS

US 8,435,706, 05/2013, Sekido et al. (withdrawn)
(Continued)

*Primary Examiner* — Sean Basquill
(74) *Attorney, Agent, or Firm* — Baker & McKenzie LLP

(57) ABSTRACT

A method of quenching excited state energy from a pigment that has been excited by absorption of light having a wavelength in the wavelength range of 290-800 nm, comprising reacting a pigment with a conjugated fused tricyclic compound having electron withdrawing groups:
of Formula (II) or a salt thereof:

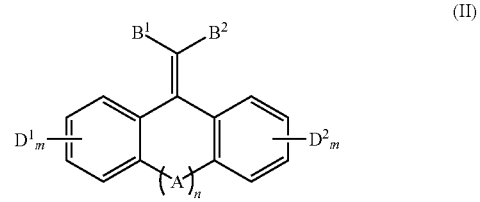

(II)

wherein:
A is selected from the group consisting of O, S, C=O, C=S, and (Continued)

$B^1$, $B^2$, $D^1$, and $D^2$ are each independently selected from the group consisting of F, Cl, Br, I, $CF_3$, $CCl_3$, $NR^3_3{}^+$, $NO_2$, CN, C(=O)$R^4$, C(=O)O$R^1$, $SO_2R^5$, aryl, and —C=CH$R^6$;

each m independently is 0, 1, 2, 3, or 4;

n is 0 or 1;

each $R^1$ is independently selected from the group consisting of H, alkyl, alkenyl, alkynyl, cycloalkyl, cycloalkenyl, and aryl;

$R^2$ is selected from the group consisting of H, alkyl, cycloalkyl, alkenyl, alkynyl, and aryl;

each $R^3$ is independently selected from the group consisting of H and $C_1$-$C_6$ alkyl;

each $R^4$ is independently selected from the group consisting of H, alkyl, alkenyl, alkynyl, cycloalkyl, cycloalkenyl, and aryl;

each $R^5$ is independently selected from the group consisting of H, O$^-$, OH, $NH_2$, and Cl; and, each $R^6$ is independently selected from the group consisting of alkyl, alkenyl, alkynyl, cycloalkyl, cycloalkenyl, and aryl.

33 Claims, 24 Drawing Sheets

(51) Int. Cl.
| | |
|---|---|
| A61K 8/49 | (2006.01) |
| A61Q 17/04 | (2006.01) |
| A61K 31/382 | (2006.01) |
| C07D 311/82 | (2006.01) |
| C07D 335/12 | (2006.01) |
| A61K 8/46 | (2006.01) |
| A61K 31/216 | (2006.01) |
| A61K 31/352 | (2006.01) |
| C07C 325/02 | (2006.01) |
| C07C 255/41 | (2006.01) |
| A61K 45/06 | (2006.01) |
| C09B 11/28 | (2006.01) |
| C09B 23/01 | (2006.01) |
| C09B 23/04 | (2006.01) |
| C09B 23/10 | (2006.01) |

(52) U.S. Cl.
CPC ............ *A61K 8/498* (2013.01); *A61K 8/4986* (2013.01); *A61K 31/216* (2013.01); *A61K 31/352* (2013.01); *A61K 31/382* (2013.01); *A61K 45/06* (2013.01); *A61Q 17/04* (2013.01); *C07C 255/41* (2013.01); *C07C 325/02* (2013.01); *C07D 311/82* (2013.01); *C07D 335/12* (2013.01); *C09B 11/28* (2013.01); *C09B 23/005* (2013.01); *C09B 23/0058* (2013.01); *C09B 23/04* (2013.01); *C09B 23/105* (2013.01); *C09B 23/107* (2013.01); *C07C 2603/18* (2017.05); *C07C 2603/24* (2017.05)

(58) Field of Classification Search
CPC ........ A61K 8/46; A61K 8/494; A61K 31/216; A61K 31/352; A61K 45/06; C07D 311/82; C07D 335/12; C07C 325/02; C07C 255/41; C07C 2603/18
See application file for complete search history.

(56) References Cited

U.S. PATENT DOCUMENTS

| | | |
|---|---|---|
| 3,408,188 A | 10/1968 | Mammino |
| 3,408,190 A | 10/1968 | Mammino |
| 3,615,412 A | 10/1971 | Hessel |
| 3,674,473 A | 7/1972 | Blanchette |
| 3,752,668 A | 8/1973 | Baltazzi |
| 3,791,824 A | 2/1974 | Bauer et al. |
| 3,841,871 A | 10/1974 | Blanchette |
| 3,864,126 A | 2/1975 | Nishide et al. |
| 3,933,505 A | 1/1976 | Shiba et al. |
| 3,976,485 A | 8/1976 | Groner |
| 3,984,378 A | 10/1976 | Kubota et al. |
| 4,012,251 A | 3/1977 | Turner |
| 4,018,602 A | 4/1977 | Chu |
| 4,032,226 A | 6/1977 | Groner |
| 4,040,735 A | 8/1977 | Winkelmann et al. |
| 4,069,046 A | 1/1978 | Hoegl et al. |
| 4,106,934 A | 8/1978 | Turnblom |
| 4,256,819 A | 3/1981 | Webster et al. |
| 4,350,748 A | 9/1982 | Lind |
| 4,427,753 A | 1/1984 | Fujimura et al. |
| 4,474,865 A | 10/1984 | Ong et al. |
| 4,515,881 A | 5/1985 | Sawada et al. |
| 4,546,059 A | 10/1985 | Ong et al. |
| 4,552,822 A | 11/1985 | Kazmaier et al. |
| 4,559,287 A | 12/1985 | McAneney et al. |
| 4,562,132 A | 12/1985 | Ong et al. |
| 4,567,124 A | 1/1986 | Ohta et al. |
| 4,576,886 A | 3/1986 | Hirose et al. |
| 4,579,800 A | 4/1986 | Hirose et al. |
| 4,599,287 A | 7/1986 | Fujimaki et al. |
| 4,606,861 A | 8/1986 | Ong et al. |
| 4,609,602 A | 9/1986 | Ong et al. |
| 4,810,608 A | 3/1989 | Ueda |
| 4,820,601 A | 4/1989 | Ong et al. |
| 4,822,704 A | 4/1989 | Akasaki et al. |
| 4,833,054 A | 5/1989 | Akasaki et al. |
| 4,835,081 A | 5/1989 | Ong et al. |
| 4,842,971 A | 6/1989 | Sugaiwa et al. |
| 4,845,263 A | 7/1989 | Ong et al. |
| 4,868,080 A | 9/1989 | Umehara et al. |
| 4,895,781 A | 1/1990 | Takai |
| 4,921,769 A | 5/1990 | Yuh et al. |
| 4,925,757 A | 5/1990 | Takenouchi et al. |
| 4,942,106 A | 7/1990 | Takai et al. |
| 4,943,501 A | 7/1990 | Kinoshita et al. |
| 4,948,911 A | 8/1990 | Bugner et al. |
| 4,990,634 A | 2/1991 | Mukai et al. |
| 4,997,737 A | 3/1991 | Bugner et al. |
| 5,011,757 A | 4/1991 | Akasaki et al. |
| 5,011,969 A | 4/1991 | Akasaki et al. |
| 5,017,645 A | 5/1991 | Ong et al. |
| 5,023,356 A | 6/1991 | Mukai et al. |
| 5,028,505 A | 7/1991 | Akasaki et al. |
| 5,034,294 A | 7/1991 | Go et al. |
| 5,053,302 A | 10/1991 | Makino et al. |
| 5,075,189 A | 12/1991 | Ichino et al. |
| 5,075,487 A | 12/1991 | Akasaki et al. |
| 5,077,164 A | 12/1991 | Ueda et al. |
| 5,080,991 A | 1/1992 | Ono et al. |
| 5,102,757 A | 4/1992 | Akasaki et al. |
| 5,132,190 A | 7/1992 | Yamada et al. |
| 5,153,085 A | 10/1992 | Akasaki et al. |
| 5,158,847 A | 10/1992 | Go et al. |
| 5,166,016 A | 11/1992 | Badesha et al. |
| 5,168,024 A | 12/1992 | Yamamoto et al. |
| 5,194,355 A | 3/1993 | Ohmura et al. |
| 5,213,924 A | 5/1993 | Sakamoto |
| 5,235,104 A | 8/1993 | Yamada et al. |
| 5,286,589 A | 2/1994 | Go et al. |
| 5,308,726 A | 5/1994 | Hirano et al. |
| 5,324,604 A | 6/1994 | Bugner et al. |
| 5,336,577 A | 8/1994 | Spiewak et al. |
| 5,356,746 A | 10/1994 | Sugiyama et al. |
| 5,389,481 A | 2/1995 | Saita et al. |
| 5,413,885 A | 5/1995 | Datta et al. |

(56) References Cited

U.S. PATENT DOCUMENTS

| | | | |
|---|---|---|---|
| 5,435,991 A | 7/1995 | Golman et al. | |
| 5,437,950 A | 8/1995 | Yu et al. | |
| 5,492,784 A | 2/1996 | Yoshikawa et al. | |
| 5,501,927 A | 3/1996 | Imai et al. | |
| 5,520,905 A * | 5/1996 | Uhlmann | A61K 8/44 424/59 |
| 5,578,405 A | 11/1996 | Ikegami et al. | |
| 5,658,702 A | 8/1997 | Nukada | |
| 5,663,213 A | 9/1997 | Jones et al. | |
| 5,677,095 A | 10/1997 | Kikuchi et al. | |
| 5,698,141 A | 12/1997 | Kumar | |
| 5,698,355 A | 12/1997 | Imai et al. | |
| 5,723,072 A | 3/1998 | Kumar | |
| 5,744,267 A | 4/1998 | Meerholz et al. | |
| 5,780,194 A | 7/1998 | Katsukawa et al. | |
| 5,795,690 A | 8/1998 | Takegawa et al. | |
| 5,834,144 A | 11/1998 | Kim et al. | |
| 5,871,877 A | 2/1999 | Ong et al. | |
| 5,874,193 A | 2/1999 | Liu et al. | |
| 5,916,719 A | 6/1999 | Kim et al. | |
| 5,942,359 A | 8/1999 | Kinoshita et al. | |
| 6,004,724 A | 12/1999 | Yamato et al. | |
| 6,036,946 A | 3/2000 | Greene | |
| 6,187,493 B1 | 2/2001 | Katsukawa et al. | |
| 6,194,110 B1 | 2/2001 | Hsiao et al. | |
| 6,287,737 B1 | 9/2001 | Ong et al. | |
| 6,322,941 B1 | 11/2001 | Hsiao et al. | |
| 6,465,648 B1 | 10/2002 | Tadokoro et al. | |
| 6,485,886 B1 | 11/2002 | Yamato et al. | |
| 6,544,701 B2 | 4/2003 | Tadokoro et al. | |
| 6,558,851 B1 | 5/2003 | Fjeldstad et al. | |
| 6,586,148 B1 | 7/2003 | Graham et al. | |
| 6,656,650 B1 | 12/2003 | Lin et al. | |
| 6,756,169 B2 | 6/2004 | Lin et al. | |
| 6,770,410 B2 | 8/2004 | Yu et al. | |
| 6,800,274 B2 | 10/2004 | Bonda et al. | |
| 6,806,024 B1 | 10/2004 | Kura et al. | |
| 6,849,367 B2 | 2/2005 | Shoshi et al. | |
| 6,858,363 B2 | 2/2005 | Belknap et al. | |
| 6,890,693 B2 | 5/2005 | Zhu et al. | |
| 6,899,984 B2 | 5/2005 | Tokarski et al. | |
| 6,905,804 B2 | 6/2005 | Law et al. | |
| 6,919,473 B2 | 7/2005 | Bonda et al. | |
| 6,926,887 B2 | 8/2005 | Bonda et al. | |
| 6,946,226 B2 | 9/2005 | Wu et al. | |
| 6,946,227 B2 | 9/2005 | Lin et al. | |
| 6,955,869 B2 | 10/2005 | Jubran et al. | |
| 6,962,692 B2 | 11/2005 | Bonda et al. | |
| 6,964,833 B2 | 11/2005 | Tokarski et al. | |
| 6,991,880 B2 | 1/2006 | Tong et al. | |
| 7,011,917 B2 | 3/2006 | Jubran et al. | |
| 7,029,812 B2 | 4/2006 | Tokarski et al. | |
| 7,037,630 B2 | 5/2006 | Vong et al. | |
| 7,037,632 B2 | 5/2006 | Jubran et al. | |
| 7,045,263 B2 | 5/2006 | Zhu et al. | |
| 7,045,264 B2 | 5/2006 | Yokota et al. | |
| 7,056,632 B2 | 6/2006 | Ioannidis | |
| 7,063,928 B2 | 6/2006 | Law et al. | |
| 7,067,230 B2 | 6/2006 | Cammack et al. | |
| 7,070,892 B2 | 7/2006 | Bender et al. | |
| 7,070,894 B2 | 7/2006 | Bender et al. | |
| 7,078,139 B2 | 7/2006 | Yokota et al. | |
| 7,090,953 B2 | 8/2006 | Getautis et al. | |
| 7,094,510 B2 | 8/2006 | Jubran et al. | |
| 7,115,348 B2 | 10/2006 | Zhu et al. | |
| 7,126,013 B2 | 10/2006 | Heeney et al. | |
| 7,129,012 B2 | 10/2006 | Sekiya et al. | |
| 7,163,771 B2 | 1/2007 | Ioannidis et al. | |
| 7,172,843 B2 | 2/2007 | Lee et al. | |
| 7,175,958 B2 | 2/2007 | Shoshi et al. | |
| 7,183,026 B2 | 2/2007 | Zhu et al. | |
| 7,205,080 B2 | 4/2007 | Iwasaki et al. | |
| 7,223,507 B2 | 5/2007 | Ioannidis et al. | |
| 7,232,633 B2 | 6/2007 | Qi et al. | |
| 7,235,587 B2 | 6/2007 | Bonda et al. | |
| 7,244,541 B2 | 7/2007 | Tokarski et al. | |
| 7,291,431 B2 | 11/2007 | Tokarski et al. | |
| 7,291,432 B2 | 11/2007 | Lin et al. | |
| 7,297,458 B2 | 11/2007 | Belknap et al. | |
| 7,312,007 B2 | 12/2007 | Lin et al. | |
| 7,326,511 B2 | 2/2008 | Matsumoto et al. | |
| 7,354,534 B2 | 4/2008 | Lee et al. | |
| 7,357,919 B2 | 4/2008 | Candau | |
| 7,357,920 B2 | 4/2008 | Candau | |
| 7,390,601 B2 | 6/2008 | Wu et al. | |
| 7,396,622 B2 | 7/2008 | Nagasaka et al. | |
| 7,431,917 B2 | 10/2008 | Candau | |
| 7,491,989 B2 | 2/2009 | Loutfy et al. | |
| 7,501,216 B2 | 3/2009 | Jubran et al. | |
| 7,544,350 B2 | 6/2009 | Bonda et al. | |
| 7,544,453 B2 | 6/2009 | Freeman et al. | |
| 7,560,161 B2 | 7/2009 | Qi et al. | |
| 7,588,702 B2 | 9/2009 | Bonda et al. | |
| 7,592,113 B2 | 9/2009 | Nagasaka et al. | |
| 7,597,825 B2 | 10/2009 | Bonda et al. | |
| 7,745,083 B2 | 6/2010 | Nagasaka et al. | |
| 7,776,614 B2 | 8/2010 | Bonda | |
| 7,799,317 B2 | 9/2010 | Bonda et al. | |
| 7,893,192 B2 | 2/2011 | Sasaki et al. | |
| 7,928,249 B2 | 4/2011 | Marks et al. | |
| 7,981,402 B2 | 7/2011 | Bonda et al. | |
| 8,119,107 B2 | 2/2012 | Müller et al. | |
| 8,236,469 B2 | 8/2012 | Belknap et al. | |
| 9,125,829 B2 | 9/2015 | Bonda et al. | |
| 9,145,383 B2 | 9/2015 | Bonda et al. | |
| 9,611,246 B2 | 4/2017 | Bonda et al. | |
| 2002/0102484 A1 | 8/2002 | Miyamoto et al. | |
| 2003/0013028 A1 | 1/2003 | Tadokoro et al. | |
| 2003/0190540 A1 | 10/2003 | Shashi et al. | |
| 2003/0194626 A1 | 10/2003 | Zhu et al. | |
| 2003/0198880 A1 | 10/2003 | Law et al. | |
| 2003/0211413 A1 | 11/2003 | Lin et al. | |
| 2003/0228534 A1 | 12/2003 | Zhu | |
| 2003/0232261 A1 | 12/2003 | Tokarski et al. | |
| 2003/0232264 A1 | 12/2003 | Tokarski et al. | |
| 2003/0235771 A1 | 12/2003 | Yokota et al. | |
| 2004/0013960 A1 | 1/2004 | Lim et al. | |
| 2004/0018439 A1 | 1/2004 | Tong et al. | |
| 2004/0018440 A1 | 1/2004 | Lin et al. | |
| 2004/0043313 A1 | 3/2004 | Zhu et al. | |
| 2004/0043314 A1 | 3/2004 | Jubran et al. | |
| 2004/0057912 A1 | 3/2004 | Bonda et al. | |
| 2004/0057914 A1 | 3/2004 | Bonda et al. | |
| 2004/0057916 A1 | 3/2004 | Bonda et al. | |
| 2004/0062726 A1 | 4/2004 | Bonda et al. | |
| 2004/0063011 A1 | 4/2004 | Lin et al. | |
| 2004/0081903 A1 | 4/2004 | Tokarski et al. | |
| 2004/0086796 A1 | 5/2004 | Yu et al. | |
| 2004/0096761 A1 | 5/2004 | Lin et al. | |
| 2004/0101772 A1 | 5/2004 | Zhu et al. | |
| 2004/0101773 A1 | 5/2004 | Zhu et al. | |
| 2004/0137345 A1 | 7/2004 | Yokota et al. | |
| 2004/0142257 A1 | 7/2004 | Ioannidis | |
| 2004/0142260 A1 | 7/2004 | Lee et al. | |
| 2004/0151996 A1 | 8/2004 | Vong et al. | |
| 2004/0161685 A1 | 8/2004 | Getautis et al. | |
| 2004/0170909 A1 | 9/2004 | Jubran et al. | |
| 2004/0176560 A1 | 9/2004 | Heeney et al. | |
| 2004/0197685 A1 | 10/2004 | Ioannidis et al. | |
| 2004/0197686 A1 | 10/2004 | Belknap et al. | |
| 2004/0200999 A1 | 10/2004 | Cammack et al. | |
| 2004/0241562 A1 | 12/2004 | Jubran et al. | |
| 2004/0242841 A1 | 12/2004 | Cammack et al. | |
| 2005/0042533 A1 | 2/2005 | Wu et al. | |
| 2005/0051758 A1 | 3/2005 | Yamamoto et al. | |
| 2005/0069793 A1 | 3/2005 | Jubran et al. | |
| 2005/0069795 A1 | 3/2005 | Jubran et al. | |
| 2005/0069796 A1 | 3/2005 | Iwasaki et al. | |
| 2005/0069798 A1 | 3/2005 | Jubran et al. | |
| 2005/0089789 A1 | 4/2005 | Zhu | |
| 2005/0112487 A1 | 5/2005 | Shoshi et al. | |
| 2005/0123849 A1 | 6/2005 | Law et al. | |
| 2005/0153244 A1 | 7/2005 | Matsumoto et al. | |
| 2005/0164106 A1 | 7/2005 | Bender et al. | |

(56) References Cited

U.S. PATENT DOCUMENTS

| | | |
|---|---|---|
| 2005/0172422 A1 | 8/2005 | Kravtchenko et al. |
| 2005/0175913 A1 | 8/2005 | Bender et al. |
| 2005/0214664 A1 | 9/2005 | Lin et al. |
| 2005/0222307 A1 | 10/2005 | Bonda et al. |
| 2005/0238974 A1 | 10/2005 | Sekiya et al. |
| 2005/0287453 A1 | 12/2005 | Ioannidis et al. |
| 2005/0287454 A1 | 12/2005 | Belknap et al. |
| 2006/0002869 A1 | 1/2006 | Bonda et al. |
| 2006/0029803 A1 | 2/2006 | Qi et al. |
| 2006/0029872 A1 | 2/2006 | Qi et al. |
| 2006/0057480 A1 | 3/2006 | Lin et al. |
| 2006/0083698 A1 | 4/2006 | Candau |
| 2006/0083699 A1 | 4/2006 | Candau |
| 2006/0104924 A1 | 5/2006 | Candau |
| 2006/0127794 A1 | 6/2006 | Tokarski et al. |
| 2006/0142444 A1 | 6/2006 | Lee et al. |
| 2006/0147827 A1 | 7/2006 | Tokarski et al. |
| 2006/0210898 A1 | 9/2006 | Jubran |
| 2006/0257338 A1 | 11/2006 | Bonda et al. |
| 2006/0286470 A1 | 12/2006 | Wu et al. |
| 2006/0292469 A1 | 12/2006 | Nagasaka et al. |
| 2007/0023747 A1 | 2/2007 | Loutfy et al. |
| 2007/0026331 A1 | 2/2007 | Lee et al. |
| 2007/0077505 A1 | 4/2007 | Lin et al. |
| 2007/0082283 A1 | 4/2007 | Freeman et al. |
| 2007/0148571 A1 | 6/2007 | Iwasaki et al. |
| 2007/0213503 A1 | 9/2007 | Sasaki et al. |
| 2008/0075921 A1 | 3/2008 | Tateishi |
| 2008/0193793 A1 | 8/2008 | Johannes et al. |
| 2008/0194821 A1 | 8/2008 | Johannes et al. |
| 2008/0233499 A1 | 9/2008 | Nagasaka et al. |
| 2008/0286693 A1 | 11/2008 | Matsumoto et al. |
| 2008/0305417 A1 | 12/2008 | Sugimura et al. |
| 2009/0036643 A1 | 2/2009 | Marks et al. |
| 2009/0039323 A1 | 2/2009 | Bonda et al. |
| 2009/0297218 A1 | 12/2009 | Nagasaka et al. |
| 2010/0143272 A1 | 6/2010 | Müller et al. |
| 2010/0294368 A1 | 11/2010 | Ushiro et al. |
| 2011/0033396 A1 | 2/2011 | Bonda et al. |
| 2011/0037063 A1 | 2/2011 | Buesing et al. |
| 2011/0143273 A1 | 6/2011 | Sekido et al. |
| 2011/0195353 A1 | 8/2011 | Belknap et al. |
| 2011/0251242 A1 | 10/2011 | Bonda et al. |
| 2011/0268472 A1 | 11/2011 | Sekido et al. |
| 2012/0121524 A1 | 5/2012 | Müller et al. |
| 2016/0002200 A1 | 1/2016 | Bonda et al. |
| 2016/0022555 A1* | 1/2016 | Bonda .................. C07D 335/12 252/183.12 |
| 2016/0024046 A1* | 1/2016 | Bonda .................. C07D 335/12 442/181 |

FOREIGN PATENT DOCUMENTS

| | | | |
|---|---|---|---|
| CS | 221362 | 9/1982 | |
| EP | 0351887 | 1/1990 | |
| EP | 0761201 A1 | 3/1997 | |
| EP | 0761214 | 3/1997 | |
| EP | 1661548 | 5/2006 | |
| EP | 2025324 | 2/2009 | |
| EP | 2070550 | 6/2009 | |
| JP | H1048554 | 2/1998 | |
| JP | H1048854 | 2/1998 | |
| JP | 2000-162798 | 6/2000 | |
| JP | 2005-139263 | 6/2005 | |
| JP | 2010127963 | 6/2010 | |
| WO | 0061585 | 10/2000 | |
| WO | 03045942 | 6/2003 | |
| WO | 2004047821 | 6/2004 | |
| WO | 2004110394 | 12/2004 | |
| WO | WO2004/110394 | * 12/2004 | ............... A61K 7/00 |
| WO | 2005048944 | 6/2005 | |
| WO | 2006034968 | 4/2006 | |
| WO | 2009020673 | 2/2009 | |
| WO | WO-2009/020676 A1 | 2/2009 | |

OTHER PUBLICATIONS

Takashi Nogami, et al, The Synthesis of New Electron Acceptors, 9,10-Bis[cyano-(ethoxycarbonyl)methylene]-9,10-dihydroanthracene and 10-[Cyano(ethoxycarbonyl)methylene]-9-anthrone, 54 Bull. Chem. Soc. Jpn. 3601 (1981).*

James Kennedy & Roy Pottier, Endogenous Protoporphyrin IX, a Clinically Useful Photosensitizer for Photodynamic Therapy, 14 J Photochem. Photobiol. B: Biol. 275 (1992).*

Chemistry of Porphyrins, 7 pages, downloaded from the Internet Jul. 12, 2012: <http://www.org-chem.org/yuuki/porphyrin/porphyrin.html>.

Hafez et al., Carbonyl and thiocarbonyl compounds. V. synthesis of newer unsaturated nitriles, carboxylic acids, and esters derived from xanthene and thiaxanthene, J. Org. Chem., 26:3988-91 (1961).

Latif et al., Cleavage of xanthene ethers: a new route to 9-substituted xanthenes, Can. J. Chem., 42:1736-40 (1964).

Latif et al., Cyano esters and malonitriles. V. Cyano(fluorenyl)acetic esters, hydroxy nitriles and benzimidazolylacetonitriles, Aust. J. Chem., 30:2263-9 (1977).

Lin et al., Inhibition of hepadnavirus reverse transcriptase-epsilon RNA interaction by porphyrin compounds, J. Virol., 82(5):2305-12 (2008).

National Cancer Institute, Antioxidants and Cancer Prevention: Fact Sheet (Jul. 28, 2004).

Nogami et al., The synthesis of new electron acceptors, 9,10-bis[cyano(ethoxycarbonyl)methylene]-9,10-dihydroanthracene and 10-[cyano(ethoxycarbonyl)methylene]-9-anthrone, Bull. Chem. Soc., 54:3601-2 (1981).

Photodynamic Therapy, downloaded from the Internet <http://en.wikipedia.org/wiki/photodynamic_therapy> (last modified Mar. 9, 2013).

Walter et al., Porphyrins and phthalocyanines in solar photovoltaic cells, J. Porphyrins Phthalocyanines, 14:759-92 (2010).

Worlikar et al., Palladium-catalyzed synthesis of 9-fluorenylidenes through aryne annulation, Org. Lett., 11(11):2413-6 (2009).

Zeid et al., Reactions of 4-chloro-9H-xanthene-9-thione with tetrachloro-o-benzoquinone, Liebigs Ann. Chem., 196-8 (1984).

P.R. Droupadi et al. "Charge Transfer Complexes of Pheophytin a with Nitroaromatics. Electron Transfer from Excited Singlet of Pheophytin A to Nitroaromatics", Photochemistry and Photobiology, vol. 39, No. 2, Feb. 1, 1984, pp. 161-167, XP055072972.

International Search Report and the Written Opinion of PCT/US2012/067519 dated Nov. 18, 2013.

International Search Report and the Written Opinion of PCT/US2013/054408 dated Dec. 2, 2013.

Jing Li et al, "Synthesis of New C2-Symmetric Fluoren-9-ylidene Malonate Derived Bis(oxazoline) Ligands and Their Application in Friedel-Crafts Reactions", Molecules, vol. 15, No. 12, Nov. 26, 2010, pp. 8582-8592, XP055240050.

Naela Assadi et al, "Overcrowded naphthologs of mono-bridged tetraarylethylenes: analogs of bistricyclic aromatic enes", Structural Chemistry, Kluwer Academic Publishers-Plenum Publishers, NE vol. 20, No. 4, May 13, 2009, pp. 541-556, XP019688913.

M.M. Sidky et al, "Action of Triphenylphosphine on some Episulphides; a new Method for the Synthesis of Thermochromic Ethylenes", Journal Fuer Praktische Chemie, vol. 312, No. 1, Jan. 1, 1970, pp. 51-54, XP055240149.

Nishino et al, "Manganese (III)-Mediated Carbon-Carbon Bond Formation in the Reaction of Kanthense With Active Methylene Compounds" The Journal of Organic Chemistry, American Chemical Society, US, vol. 57, Jan. 1, 1992, pp. 3551-3557, XP000984589.

Xiaojie Zhang et al, "Synthesis, Self-Assembly, and Charge Transporting Property of Contorted Tetrabenzocoronenes", The Journal of Organic Chemistry, vol. 75, No. 23, Dec. 3, 2010, pp. 3069-8077, XP055240158.

Ruirui Zhang et al, "Multifuntional Core-Shell Nanoparticles as Highly Efficient Imaging and Photosensitizing Agents", Langmuir, vol. 25, No. 17, Sep. 1, 2009, pp. 10153-10158, XP055240180, New York, NY.

P.R. Droupadi et al, "Charge Transfer Complexes of Pheophytic a With Nitroaromatics. Electron Transfer From Excited Singlet of Pheophytin a to Nitroaromatics" Photochemistry and Photobiology, vol. 39, No. 2, Feb. 1, 1984, pp. 161-167, XP055072972.

(56) References Cited

OTHER PUBLICATIONS

Tapan K. Mukherjee et al "9-Dicyanomethylene-2, 4, 7-Trinitrofluorene, a New Electron Acceptor", The Journal of Organic Chemistry, vol. 30, No. 2, Feb. 1, 1965, pp. 644-646, XP055240094.
Extended European Search Report dated Jan. 21, 2016 for European Patent Application No. 13827223.2.
International Preliminary Report on Patentability and Written Opinion from corresponding PCT/US2013/054408 dated Feb. 10, 2015.
International Preliminary Report on Patentability and Written Opinion from corresponding PCT/US2012/067519 dated Feb. 10, 2015.
Examination report from co-pending Australian application number 2013299403 dated Apr. 18, 2016.
Examination report from co-pending Australian application number 2013299403 dated Apr. 18, 2017.
Jones et al., Tetrahedron, 1966, 22(9), pp. 3021-3026.
Caira et al., Acta Crys. Sec. C, 1984, C40(10), pp. 1710-1712.
Hirakawa et al., J. Org. Chem., 1986, 51(7), pp. 1083-1087.
First Official Action from Chinese Patent Application No. 201380053282.5 dated Dec. 22, 2015.
Second Official Action from Chinese Patent Application No. 201380053282.5 dated Jul. 1, 2016.
Third Official Action from Chinese Patent Application No. 201380053282.5 dated Jan. 25, 2017.
International Search Report and Written Opinion for PCT/US2012/067519 dated Nov. 18, 2013.
International Search Report and Written Opinion for PCT/US2013/054408 dated Dec. 2, 2013.

\* cited by examiner

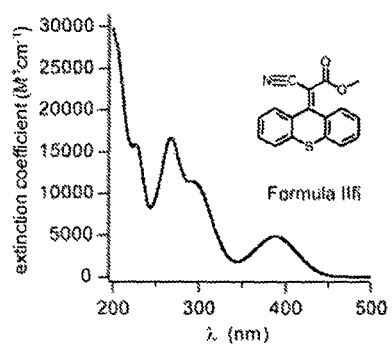
FIG. 1E
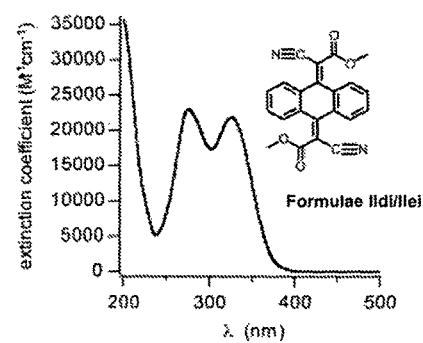
FIG. 1F
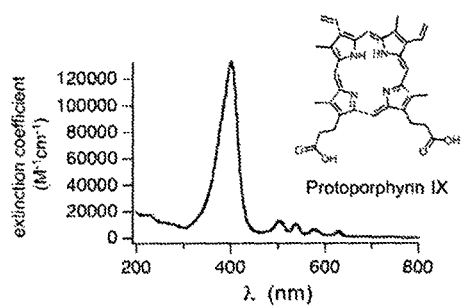
FIG. 2A
FIG. 2B

FIG. 3A
FIG. 3B
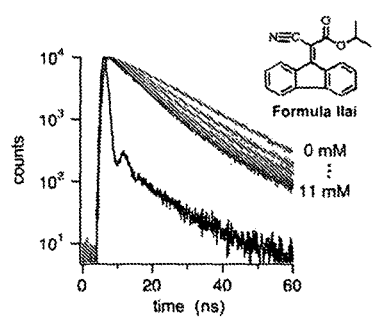
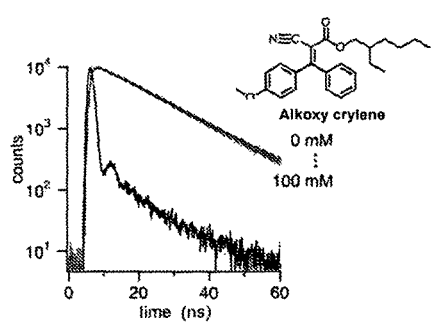
FIG. 4A
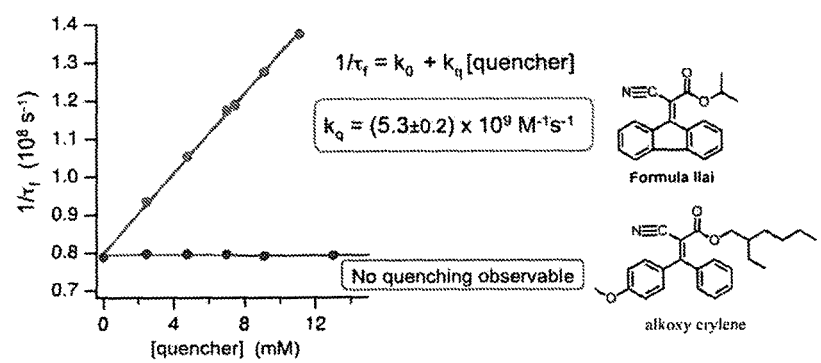

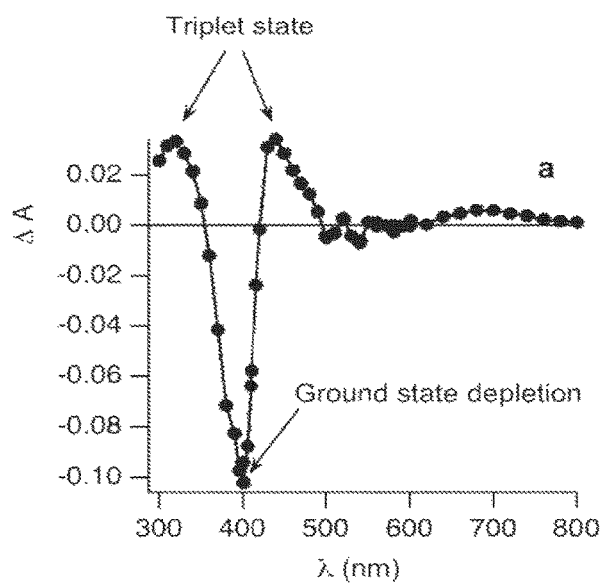
FIG. 5A
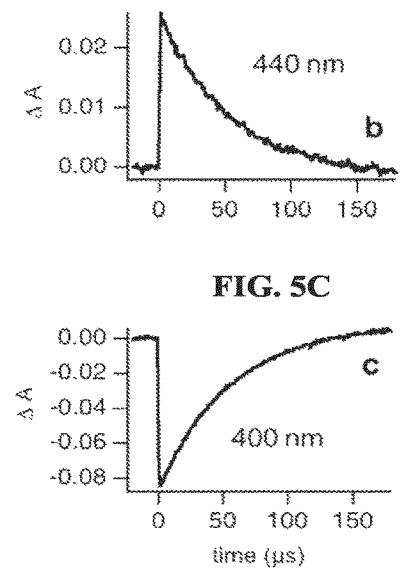
FIG. 5B
FIG. 5C
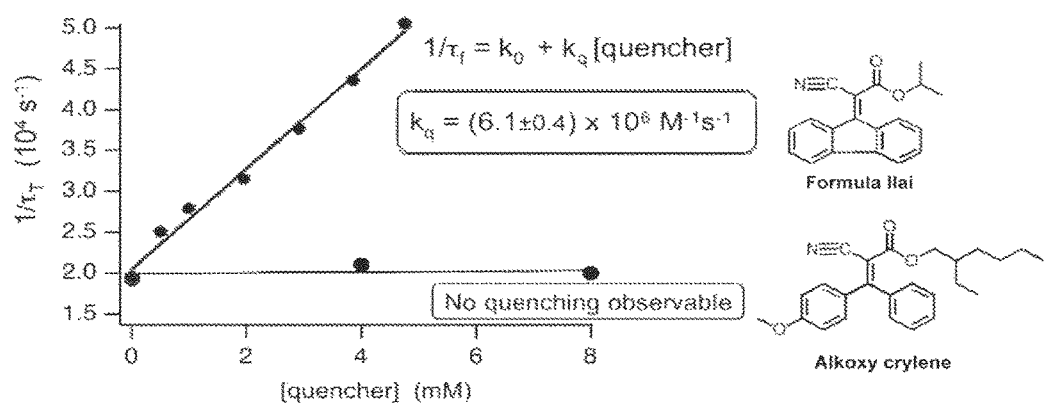
FIG. 6A

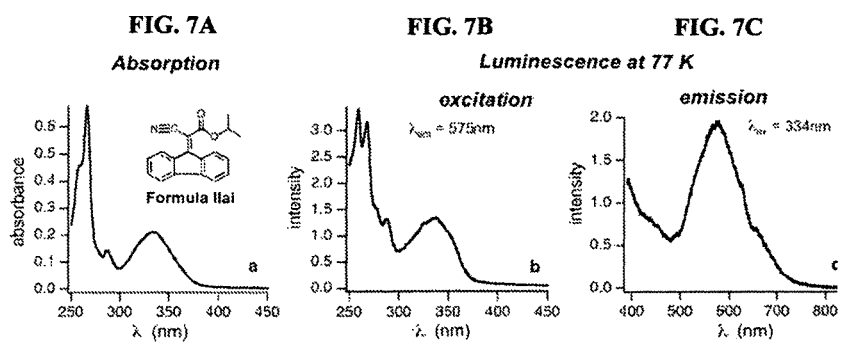
FIG. 7A Absorption
FIG. 7B Luminescence at 77 K — excitation
FIG. 7C emission
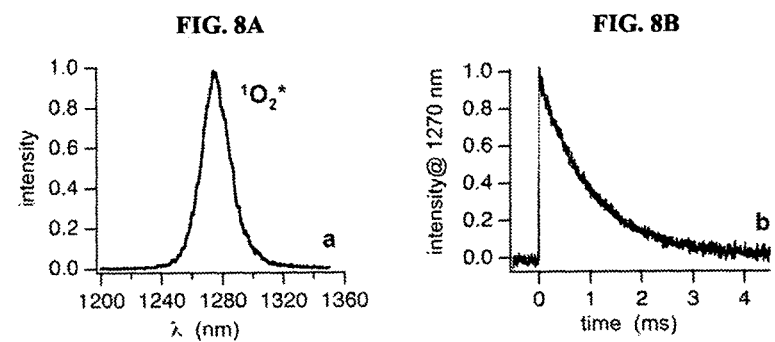
FIG. 8A
FIG. 8B

FIG. 12A      FIG. 12B
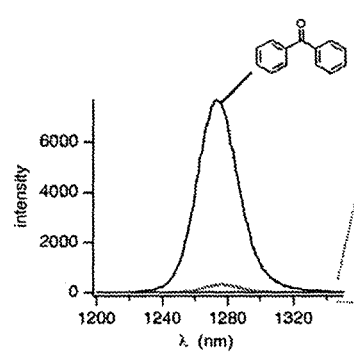
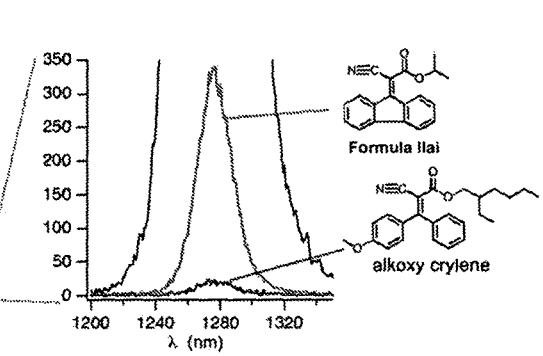

$I_0/I = 1 + k_q \tau_f [\text{quencher}]$ $K_{SV} = k_{q,q} \tau_{f,s}$

Formula IIci

Formula IIdi

Formula IIei

METHOD OF QUENCHING SINGLET AND TRIPLET EXCITED STATES OF PIGMENTS, SUCH AS PORPHYRIN COMPOUNDS, PARTICULARLY PROTOPORPHYRIN IX, WITH CONJUGATED FUSED TRICYCLIC COMPOUNDS HAVE ELECTRON WITHDRAWING GROUPS, TO REDUCE GENERATION OF REACTIVE OXYGEN SPECIES, PARTICULARLY SINGLET OXYGEN

CROSS-REFERENCE TO RELATED APPLICATIONS

This application claims priority to International Patent Application No. PCT/US2012/67519, filed Dec. 3, 2012, which claims the benefit of U.S. Provisional Patent Application No. 61/681,916, filed on Aug. 10, 2012, which is incorporated by reference in its entirety.

FIELD OF THE INVENTION

The present invention is directed to a method of quenching singlet and triplet electronic excited states of photodegradable pigments with conjugated fused tricyclic compounds having electron withdrawing groups. More particularly, it has been found that conjugated fused tricyclic compounds having electron withdrawing groups quench the singlet and triplet excited states of pigments, such as porphyrin compounds, by accepting or donating an electron, thereby returning the pigments back to their ground state to reduce the formation of free radical (singlet state) oxygen and/or other reactive oxygen species and radical compounds that are damaging to skin cells. Porphyrin compounds, for example, reach an excited state when excited by visible radiation at a wavelength in the range of about 290 to about 800 nm, e.g., sunlight, and when the excited porphyrin compound is reacted with a conjugated fused tricyclic compound having electron withdrawing groups, the excited porphyrin compound, and other photolabile pigments, are returned to their ground state before interacting with cellular oxygen, thereby generating substantially less singlet state oxygen, and preventing oxidative stress to skin cells.

BACKGROUND AND PRIOR ART

Endogenous pigments are substances in living matter that absorb visible light. They may also absorb UV radiation. These substances are produced either within tissues and serve a physiological function, or they are by-products of the metabolic process. Endogenous pigments can be classified into non-hematogenous pigments and hematogenous (i.e., blood derived) pigments. Non-hematogenous pigments include, e.g., melanins, flavins, pterins, and urocanic acid. Melanins are derived from tyrosine, and include eumelaninm pheomelanin, and neuromelanin. Flavins are a group of organic compounds based on pteridine, formed by the tricyclic heteronuclear organic ring isoalloxazine. Examples of flavins include riboflavin, flavin mononucleotide, flavoproteins, and flavin adenine dinucleotide. Pterins are heterocyclic compounds composed of a pteridine ring system, with a keto group and an amino group on positions 4 and 2, respectively. Examples of pterins include pteridine, biopterin, tetrahydrobiopterin, molybdopterin, cyanopterin, tetrahydromethanopterin, and folic acid. Urocanic acid is an intermediate in the catabolism of L-histidine. Hematogenous pigments include, e.g., hemoglobin, bile pigments, and porphyrins. Hemoglobin is a basic, conjugated protein that is responsible for the transportation of oxygen and carbon dioxide within the blood stream. It is composed of protein, globin, and heme—four molecules of heme are attached to each molecule of globin.

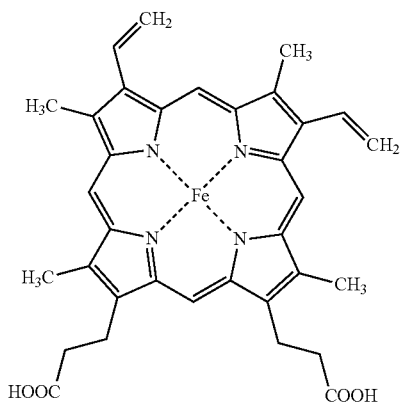

Heme B group of hemoglobin complexed to four interior nitrogen atoms Bile pigments are the metabolic products of heme, and include bilirubin (yellow, tetrapyrrolic breakdown product) and biliverdin (green, tetrapyrrolic breakdown product).

Porphyrins are a group of organic compounds, mainly naturally occurring, but also can be exogenous. Porphyrins are heterocyclic macrocycles composed of four modified pyrrole subunits interconnected at their a carbon atoms via methine bridges (=CH—), as shown in Formula (I). Porphyrins are aromatic. That is, they obey Hückel's rule for aromaticity, possessing $4n+2$ $\pi$ electrons ($n=4$ for the shortest cyclic path) delocalized over the macrocycle. Thus, porphyrin macrocycles are highly conjugated systems and typically have very intense absorption bands in the visible region and may be deeply colored. The macrocycle has 26 $\pi$ electrons in total. The parent porphyrin is porphine, and substituted porphines are called porphyrins. The porphyrin compounds that have their singlet and triplet excited states quenched by the conjugated, fused tricyclic compound having electron withdrawing groups include any porphyrin compound that includes the moiety of Formula (I) (and derivatives and tautomers thereof), as shown in Formula Ia, particularly protoporphyrin IX, Formula Ib.

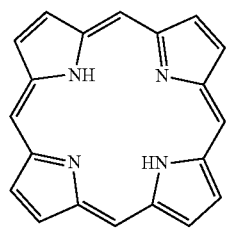

(I)

-continued

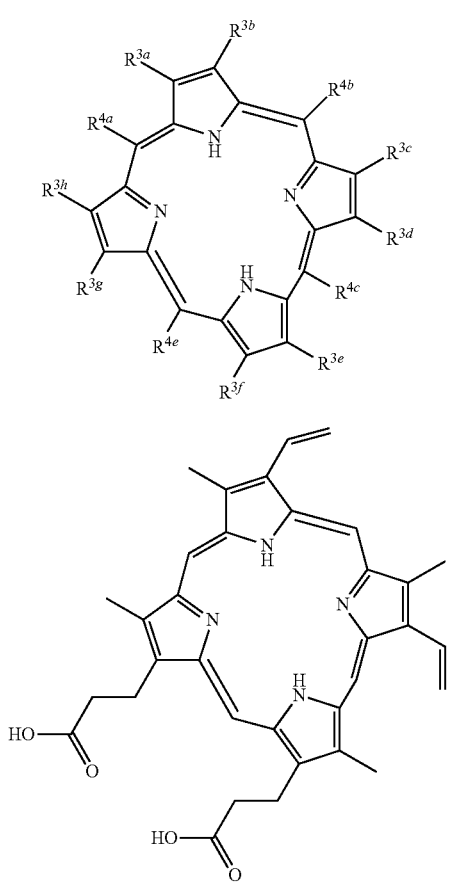

Ia

Ib

Structure of Porphine,
The Simplest Porphyrin

A porphyrin without a metal-ion in its cavity is a free base. Some iron-containing porphyrins are called hemes, the pigment in red blood cells. As previously discussed, heme is a cofactor of the protein hemoglobin. Heme-containing proteins, or hemoproteins, are found extensively in nature. Hemoglobin and myoglobin are two $O_2$-binding proteins that contain iron porphyrins. Various cytochromes are also hemoproteins.

The absorption of visible light (at about 400 to about 800 nm and UV of about 290 to about 400 nm) by a porphyrin compound causes the excitation of an electron in the porphyrin molecule from an initially occupied, lower energy orbital to a higher energy, previously unoccupied orbital. The energy of the absorbed photon is used to energize an electron and cause it to "jump" to a higher energy orbital. See Turro, Modern Molecular Photochemistry, 1991. Two excited electronic states derive from the electronic orbital configuration produced by visible light absorption. In one state, the electron spins are paired (antiparallel) and in the other state the electron spins are unpaired (parallel). The state with paired spins has no resultant spin magnetic moment, but the state with unpaired spins possesses a net spin magnetic moment. A state with paired spins remains a single state in the presence of a magnetic field, and is termed a singlet state. A state with unpaired spins interacts with a magnetic field and splits into three quantized states, and is termed a triplet state.

In the electronically excited state, the porphyrin molecule can transfer its excited state energy to oxygen contained in blood and/or skin cells, thereby generating cell-damaging singlet excited state oxygen (hereinafter "singlet oxygen"), or free radical oxygen. To photostabilize the excited state of the porphyrin molecule so that it does not generate cell-toxic singlet oxygen, the excited state of the porphyrin molecule must be returned to the ground state before it transfers its excited state energy to nearby oxygen molecule.

On the other hand, the excited state of porphyrins has also been intentionally harnassed to administer photodynamic therapy (PDT). Protoporphyrin IX ($C_{34}H_{34}N_4O_4$) is used in PDT, for example, as a treatment for basal cell carcinoma (BCC), which is the most common form of skin cancer in humans. The PDT treatment involves applying a photosensitizer precursor, such as aminolevulinic acid (ALA) to the cancerous cells, waiting a few hours for the ALA to be taken up by the cells and converted to protoporphyrin IX, and then irradiating the cancerous cells with light in the wavelength of about 380 to about 650 nm which excites the protoporphyrin IX to a singlet excited state after which it intersystem crosses to a triplet excited state thereby making it reactive with oxygen, thereby generating cytotoxic singlet oxygen that kills cancerous and pre-cancerous cells.

SUMMARY

In one aspect, the disclosure provides a method of quenching excited state energy from a photodegradable pigment compound that has been excited by exposure to and absorption of light having a wavelength in the wavelength range of about 290 to about 800 nm, comprising reacting the photodegraded pigment in its excited states with a conjugated fused tricyclic compound having electron withdrawing groups of Formula (II) or a salt thereof:

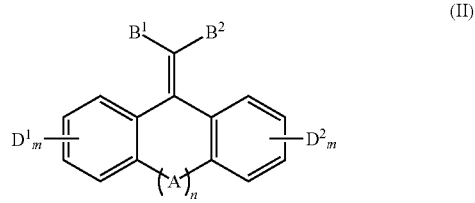

(II)

wherein:
A is selected from the group consisting of O, S, C=O, C=S,

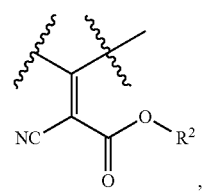

and

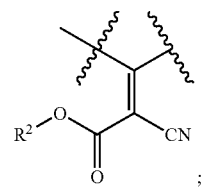

;

B¹, B², D¹, and D² are each independently selected from the group consisting of F, Cl, Br, I, $CF_3$, $CCl_3$, $NR^3_3{}^+$, $NO_2$, CN, C(=O)R⁴, C(=O)OR¹, $SO_2R^5$, aryl, and —C=CHR⁶;

each m independently is 0, 1, 2, 3, or 4;

n is 0 or 1;

each R¹ is independently selected from the group consisting of H, alkyl, alkenyl, alkynyl, cycloalkyl, cycloalkenyl, and aryl;

R² is selected from the group consisting of H, alkyl, cycloalkyl, alkenyl, alkynyl, and aryl;

each R³ is independently selected from the group consisting of H and $C_1$-$C_6$ alkyl;

each R⁴ is independently selected from the group consisting of H, alkyl, alkenyl, alkynyl, cycloalkyl, cycloalkenyl, and aryl;

each R⁵ is independently selected from the group consisting of H, O⁻, OH, $NH_2$, and Cl; and, each R⁶ is independently selected from the group consisting of alkyl, alkenyl, alkynyl, cycloalkyl, cycloalkenyl, and aryl.

In another aspect, the disclosure provides a method of suppressing the generation of singlet oxygen and/or other reactive oxygen species or radical compounds by an excited pigment when mammalian-contained pigment is exposed to light, thereby exciting the pigment to an excited state, by quenching the excited state of the pigment compound with a conjugated fused tricyclic compound having electron withdrawing groups of Formula (II) or a salt thereof. Other oxygen species presented from forming include free radical oxygen, superoxide anion, peroxide, hydroxyl radical, and hydroxyl ion.

In yet another aspect, the invention provides a method of protecting skin from oxidative stress caused by the generation of free radical oxygen comprising coating the skin with a pigment excited state quencher capable of accepting or donating an electron from or to a pigment compound in the excited state and returning the excited pigment compound to its ground state, said pigment quencher comprising a conjugated fused tricyclic compound having electron withdrawing groups of Formula (II) or a salt thereof.

In still another aspect, the invention provides a method of protecting healthy cells adjacent to cancerous or pre-cancerous cells undergoing photodynamic therapy comprising applying a composition comprising a pigment excited state quencher compound to said adjacent cells to reduce the generation of free radical oxygen and other reactive oxygen species from said healthy cells while the photodynamic therapy generates free radical oxygen from said cancerous or pre-cancerous cells with a conjugated fused tricyclic compound having electron withdrawing groups of Formula (II) or a salt thereof.

In some exemplary embodiments of any of the above aspects, the pigment compound is a porphyrin compound comprising a porphyrin moiety of Formula (I) or a derivative or tautomer thereof:

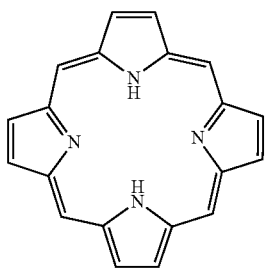

(I)

In another aspect, the invention provides a cosmetic or dermatological composition for coating a skin surface to protect the skin from getting damaging amounts of singlet oxygen when skin cell-contained or blood-contained porphyrin compounds are exposed to sunlight, or other visible light comprising a compound of Formula IIb, IIc, IId, IIe, IIf, IIg, IIh, IIi, IIj, IIk, III, IIm, IIn, or a combination thereof:

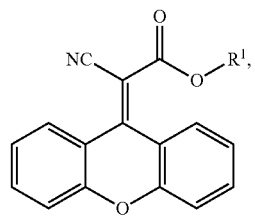

Formula IIb

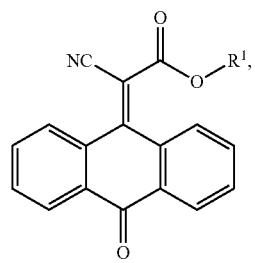

Formula IIc

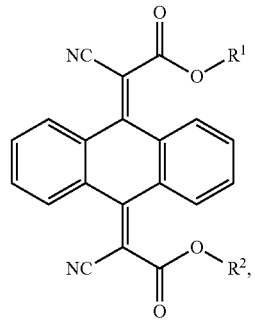

Formula IId

Formula IIe

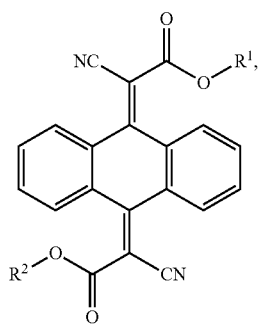

Formula IIf

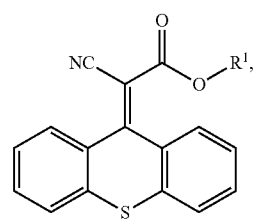

Formula IIg

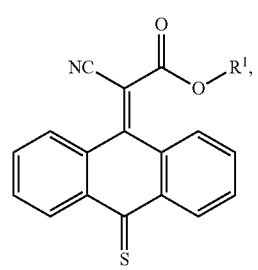

Formula IIh

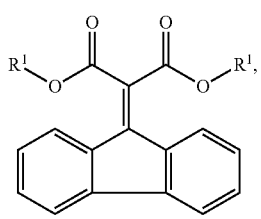

Formula IIi

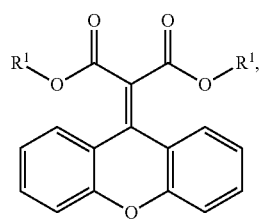

Formula IIj

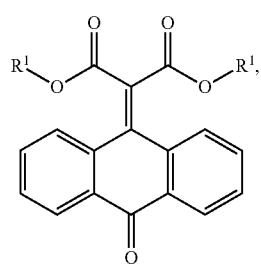

Formula IIk

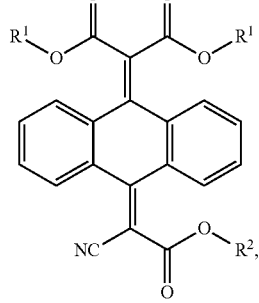

Formula IIl

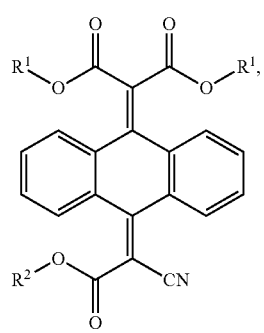

Formula IIm

Formula IIn

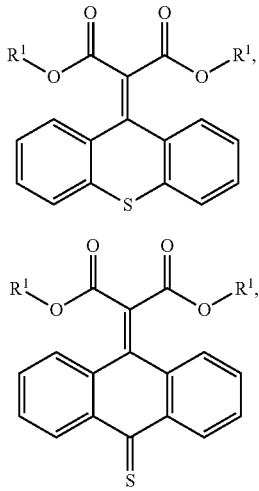

wherein:
each $R^1$ is independently selected from the group consisting of H, alkyl, alkenyl, alkynyl, cycloalkyl, cycloalkenyl, and aryl; and,
$R^2$ is selected from the group consisting of H, alkyl, cycloalkyl, alkenyl, alkynyl, and aryl.

BRIEF DESCRIPTION OF THE DRAWINGS

FIG. 2 shows an absorption spectrum (FIG. 2a) and a fluorescence spectrum (FIG. 2b) of protoporphyrin IX in acetonitrile. λex=510 nm.

FIG. 3 shows fluorescence decay traces monitored at 690 nm using time correlated single photon counting of the compound of Formula IIai (FIG. 3a) and alkoxy crylene (FIG. 3b) in acetonitrile solutions in the absence and presence of different amounts of stabilizers. λex=490 nm.

FIG. 5 is a graph showing a transient absorption spectrum (FIG. 5a) of an argon saturated acetonitrile solution of protoporphyrin IX recorded 0.1 to 1.5 µs after pulsed laser excitation (355 nm, 5 ns pulse width). Selected kinetic traces at different observation wavelengths are also included (FIGS. 5b, 5c).

FIG. 6a is a graph showing determination of $k_q$, the bimolecular rate constant for quenching of protoporphyrin IX triplet states by the compounds of Formula IIai and alkoxy crylene.

FIG. 7 shows luminescence excitation (FIG. 7b) and emission (FIG. 7c) spectra of the compound of Formula IIai in an ethanol matrix at 77 K. Room temperature absorption spectrum (FIG. 7a) of Formula IIai in ethanol solution is also shown.

FIG. 8 shows a singlet oxygen phosphorescence spectrum (FIG. 8a) and a decay trace (FIG. 8b) generated by photoexcitation (532 nm) of tetraphenylporphyrin in air saturated $CCl_4$ solutions using steady-state lamp excitation (FIG. 8a) or pulsed laser excitation (FIG. 8b).

FIG. 12 shows singlet oxygen phosphorescence spectra generated by photoexcitation of Formula IIai (FIG. 12a) or alkoxy crylene (FIG. 12b) at 355 nm in benzophenone in air saturated $CCl_4$ solutions. The concentrations were adjusted to have an absorbance of 0.3 at 355 nm. FIG. 12b is an amplification of FIG. 12a.

DETAILED DESCRIPTION OF THE PREFERRED EMBODIMENTS

Figure 1A:
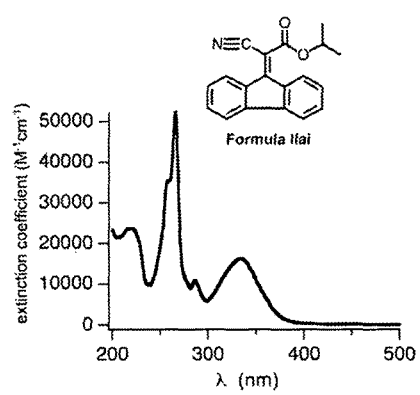
FIG. 1 shows absorption spectra of the compound of Formula IIai (FIG. 1a), Formula IIbi (FIG. 1c), Formula IIci (FIG. 1d), Formula IIfi (FIG. 1e), and a mixture of Formulae IIdi and IIei (FIG. 1f) in acetonitrile and alkoxy crylene (FIG. 1b) in acetonitrile.
Figure 1B:
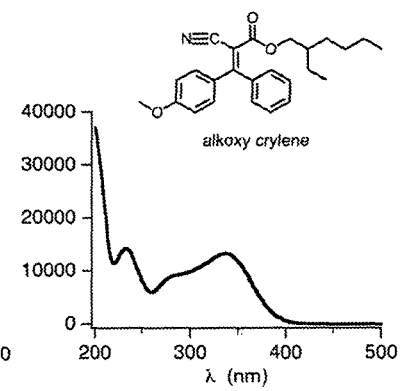
Figure 1C:
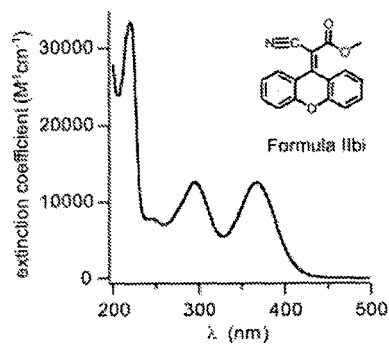

Quite surprisingly, it has been found that conjugated fused tricyclic compounds having electron withdrawing groups will quench electronically excited pigments, such as porphyrin molecules, caused when the pigment (e.g., a porphyrin) is excited by absorption of visible light. As a result, the excited state of photodegradable pigments, such as porphyrin molecules, particularly protoporphyrin IX, is returned to the ground state, thereby reducing the generation of singlet oxygen and protecting mammalian skin from oxidative stress, which would otherwise develop from sunlight-induced production of singlet state oxygen. Accordingly, by applying one or more of the conjugated fused tricyclic compounds having electron withdrawing groups, in a dermatologically or cosmetically acceptable carrier, onto mammalian skin, e.g., human skin, the skin will not suffer from oxidative stress due to the generation of potentially cytotoxic singlet oxygen and other reactive oxygen species. Thus, the compositions and methods described herein advantageously quench the excited state reached by pigments, such as porphyrins, particularly protoporphyrin IX, thereby significantly reducing the generation of singlet oxygen and other reactive oxygen species in cells, and thereby preventing oxidative stress.

Ranges may be expressed herein as from "about" or "approximately" one particular value and/or to "about" or "approximately" another particular value. When such a range is expressed, another embodiment includes from the one particular value and/or to the other particular value.

Similarly, when values are expressed as approximations, by use of the antecedent "about," it will be understood that the particular value forms another embodiment.

Definitions

The term "alkyl" refers to straight chained and branched saturated hydrocarbon groups containing one to thirty carbon atoms, for example, one to thirty carbon atoms, one to twenty carbon atoms, and/or one to ten carbon atoms. The term $C_n$ means the alkyl group has "n" carbon atoms. For example, $C_4$ alkyl refers to an alkyl group that has 4 carbon atoms. $C_1$-$C_7$ alkyl refers to an alkyl groups having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl(2-methylpropyl), t-butyl(1,1-dimethylethyl), 3,3-dimethylpentyl, and 2-ethylhexyl. Unless otherwise indicated, an alkyl group can be an unsubstituted alkyl group or a substituted alkyl group. When the term "alkyl" is in parenthesis (e.g., (alkyl)acrylate), then the alkyl group is optional.

The term "alkenyl" is defined identically as "alkyl" except for containing at least one carbon-carbon double bond, e.g., ethenyl, 1-propenyl, 2-propenyl, and butenyl. Unless otherwise indicated, an alkenyl group can be an unsubstituted alkenyl group or a substituted alkenyl group.

The term "alkynyl" is defined identically as "alkyl" except for containing at least one carbon-carbon triple bond, e.g., ethynyl, 1-propynyl, 2-propynyl, and butynyl. Unless otherwise indicated, an alkynyl group can be an unsubstituted alkynyl group or a substituted alkynyl group.

The term "cycloalkyl" as used herein refers to an aliphatic cyclic hydrocarbon group containing three to eight carbon atoms (e.g., 3, 4, 5, 6, 7, or 8 carbon atoms). The term $C_n$ means the cycloalkyl group has "n" carbon atoms. For example, $C_5$ cycloalkyl refers to a cycloalkyl group that has 5 carbon atoms in the ring. $C_5$-$C_8$ cycloalkyl refers to cycloalkyl groups having a number of carbon atoms encompassing the entire range (i.e., 5 to 8 carbon atoms), as well as all subgroups (e.g., 5-6, 6-8, 7-8, 5-7, 5, 6, 7, and 8 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group.

The term "heterocycloalkyl is defined similarly as cycloalkyl, except the ring contains one to three heteroatoms independently selected from the group consisting of oxygen, nitrogen, and sulfur. Nonlimiting examples of heterocycloalkyl groups include piperadine, tetrahydrofuran, tetrahydropyran, dihydrofuran, morpholine, thiophene, and the like. Cycloalkyl and heterocycloalkyl groups can be saturated or partially unsaturated ring systems optionally substituted with, for example, one to three groups, independently selected from the group consisting of alkyl, alkyleneOH, C(O)NH$_2$, NH$_2$, oxo (=O), aryl, haloalkyl, halo, and OH. Heterocycloalkyl groups optionally can be further N-substituted with alkyl, hydroxyalkyl, alkylenearyl, or alkyleneheteroaryl.

The term "cycloalkenyl" is defined identically as "cycloalkyl" except for containing at least one double bond, e.g., cyclobutenyl, cyclopentenyl, cyclohexenyl, cycloheptenyl, and cyclooctenyl. Unless otherwise indicated, a cycloalkenyl group can be an unsubstituted cycloalkenyl group or a substituted cycloalkenyl group.

The term "aryl" as used herein refers to monocyclic or polycyclic (e.g., fused bicyclic and fused tricyclic) carbocyclic aromatic ring systems. Examples of aryl groups include, but are not limited to, phenyl, naphthyl, tetrahydronaphthyl, phenanthrenyl, biphenylenyl, indanyl, indenyl, anthracenyl, and fluorenyl. Unless otherwise indicated, an aryl group can be an unsubstituted aryl group or a substituted aryl group.

The term "heteroaryl" as used herein refers to monocyclic or polycyclic (e.g., fused bicyclic and fused tricyclic) aromatic ring systems, wherein one to four-ring atoms are selected from the group consisting of oxygen, nitrogen, and sulfur, and the remaining ring atoms are carbon, said ring system being joined to the remainder of the molecule by any of the ring atoms. Nonlimiting examples of heteroaryl groups include, but are not limited to, pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, quinolinyl, isoquinolinyl, benzoxazolyl, benzimidazolyl, and benzothiazolyl. Unless otherwise indicated, a heteroaryl group can be an unsubstituted heteroaryl group or a substituted heteroaryl group.

The term "hydroxy" or "hydroxyl" as used herein refers to an "—OH" group.

The term "alkoxy" or "alkoxyl" as used herein refers to an "—O-alkyl" group.

The term "ester" as used herein refers to a group of the general Formula:

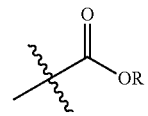

wherein R is an alkyl group or a cycloalkyl group.

The term "ether" as used herein refers to a $C_1$-$C_{30}$ alkyl group that includes at least one oxygen atom inserted within the alkyl group.

The term "amino" as used herein refers a —NH$_2$ or —NH— group, wherein each hydrogen in each Formula can be replaced with an alkyl, cycloalkyl, aryl, heteroaryl, or heterocycloalkyl group.

The term "carboxy" or "carboxyl" as used herein refers to a "—COOH" group.

The term "carboxylic ester" as used herein refers to a "—(C=O)O-alkyl" group.

The term "sulfhydryl" as used herein refers to a "—SH" group.

The term "halo" as used herein refers to a halogen (e.g., F, Cl, Br, or I).

The term "cyano" as used herein refers to a —C≡N group, also designated —CN.

A "substituted" alkyl, alkenyl, alkynyl, cycloalkyl, cycloalkenyl, aryl, heteroaryl, alkoxyl, ester, ether, or carboxylic ester refers to an alkyl, alkenyl, alkynyl, cycloalkyl, cycloalkenyl, aryl, heteroaryl, alkoxyl, ester, ether, or carboxylic ester having at least one hydrogen radical that is substituted with a non-hydrogen radical (i.e., a substitutent). Examples of non-hydrogen radicals (or substituents) include, but are not limited to, alkyl, cycloalkyl, alkenyl, cycloalkenyl, alkynyl, ether, aryl, heteroaryl, heterocycloalkyl, heterocycloalkyl, hydroxyl, oxy (or oxo), alkoxyl, ester, thioester, acyl, carboxyl, cyano, nitro, amino, amido, sulfur, and halo. When a substituted alkyl group includes more than one non-hydrogen radical, the substituents can be bound to the same carbon or two or more different carbon atoms.

The term "hydroxyalkyl" as used herein refers to an alkyl group that is substituted with a hydroxyl group.

The term "carboxyalkyl" as used herein refers to an alkyl group that is substituted with a carboxyl group.

The term "esteralkyl" as used herein refers to an alkyl group that is substituted with an ester group.

The term "sulfhydrylalkyl" as used herein refers to an alkyl group that is substituted with a sulfhydryl group.

The term "photogenerated reactive oxygen" as used herein refers to singlet oxygen or free radical oxygen, superoxide anion, peroxide, hydroxyl radical, hydroxyl ion, and other reactive oxygen species that are generated when a photodegradable pigment is excited by light having a wavelength of 290 nm to 800 nm.

Embodiments

The conjugated fused tricyclic compounds having electron withdrawing groups capable of quenching the excited state energy of pigments, such as the porphyrins compounds of Formulae (I) and Ia, are the compounds of Formula (II) or a salt thereof:

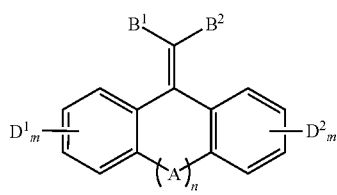

Formula (II)

Conjugated Fused Tricyclic Compounds Having Electron Withdrawing Groups wherein:

A is selected from the group consisting of O, S, C=O, C=S,

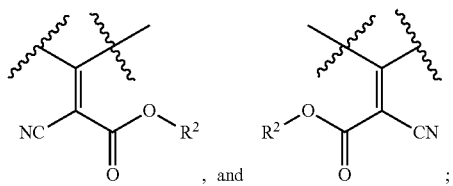

, and ;

$B^1$, $B^2$, $D^1$, and $D^2$ are each independently selected from the group consisting of F, Cl, Br, I, $CF_3$, $CCl_3$, $NR^3_3{}^+$, $NO_2$, CN, $C(=O)R^4$, $C(=O)OR^1$, $SO_2R^5$, aryl, and —C=$CHR^6$;
each m independently is 0, 1, 2, 3, or 4;
n is 0 or 1;
each $R^1$ is independently selected from the group consisting of H, alkyl, alkenyl, alkynyl, cycloalkyl, cycloalkenyl, and aryl;
$R^2$ is selected from the group consisting of H, alkyl, cycloalkyl, alkenyl, alkynyl, and aryl;
each $R^3$ is independently selected from the group consisting of H and $C_1$-$C_6$ alkyl;
each $R^4$ is independently selected from the group consisting of H, alkyl, alkenyl, alkynyl, cycloalkyl, cycloalkenyl, and aryl;
each $R^5$ is independently selected from the group consisting of H, O$^-$, OH, $NH_2$, and Cl; and,
each $R^6$ is independently selected from the group consisting of alkyl, alkenyl, alkynyl, cycloalkyl, cycloalkenyl, and aryl.

In some embodiments:
$B^1$ and $B^2$ are each independently selected from the group consisting of $CF_3$, $CCl_3$, $NR^3_3{}^+$, $NO_2$, CN, $C(=O)R^4$, $C(=O)OR^1$, $SO_2R^5$, aryl, and —C=$CHR^6$;
$D^1$ and $D^2$ are each independently selected from the group consisting of F, Cl, Br, I, $CF_3$, $CCl_3$, $NR^3_3{}^+$, $NO_2$, CN, $C(=O)R^4$, $C(=O)OR^1$, $SO_2R^5$, aryl, and —C=$CHR^6$;
each m independently is 0, 1, or 2;
n is 0 or 1;
each $R^1$ is independently selected from the group consisting of H, alkyl, alkenyl, alkynyl, and aryl;
$R^2$ is selected from the group consisting of H, alkyl, cycloalkyl, alkenyl, alkynyl, and aryl;
each $R^3$ is independently selected from the group consisting of H and $C_1$-$C_6$ alkyl;
each $R^4$ is independently selected from the group consisting of H, alkyl, alkenyl, alkynyl, and aryl;
each $R^5$ is independently selected from the group consisting of H, O$^-$, OH, $NH_2$, and Cl; and,
each $R^6$ is independently selected from the group consisting of alkyl, alkenyl, alkynyl, and aryl.

In some embodiments:
$B^1$ and $B^2$ are each independently selected from the group consisting of CN, $C(=O)R^4$, $C(=O)OR^1$, $SO_2R^5$;
$D^1$ and $D^2$ are each independently selected from the group consisting of F, Cl, Br, $CF_3$, $CCl_3$, $NR^3_3{}^+$, $NO_2$, CN, $C(=O)R^4$, $C(=O)OR^1$, and $SO_2R^5$;
each m independently is 0, 1, or 2;
n is 0 or 1;
each $R^1$ is independently selected from the group consisting of H, $C_1$-$C_{20}$ alkyl, $C_1$-$C_{20}$ alkenyl, $C_1$-$C_{20}$ alkynyl, and aryl;
$R^2$ is selected from the group consisting of H, alkyl, cycloalkyl, alkenyl, alkynyl, and aryl;
each $R^3$ is independently selected from the group consisting of H and $C_1$-$C_4$ alkyl;
each $R^4$ is independently selected from the group consisting of H, $C_1$-$C_{20}$ alkyl, $C_1$-$C_{20}$ alkenyl, $C_1$-$C_{20}$ alkynyl, and aryl; and,
each $R^5$ is independently selected from the group consisting of H, O$^-$, OH, $NH_2$, and Cl.

In some of these embodiments, both $B^1$ and $B^2$ are CN, both $B^1$ and $B^2$ are $C(=O)OR^1$, or one of $B^1$ and $B^2$ is CN and the other is $C(=O)OR^1$, wherein each $R^1$ is independently selected from the group consisting of H, $C_1$-$C_{10}$ alkyl $C_1$-$C_{10}$ alkenyl, $C_1$-$C_{10}$ alkynyl, and aryl.

In some embodiments where $R^1$, $R^2$, and/or $R^4$ is alkenyl, then the double bond can be internal or terminal. In some exemplary embodiments, the double bond is terminal. For example, $R^1$, $R^2$, and/or $R^4$ can be, e.g.,

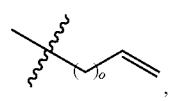

wherein o is 0, 1, 2, 3, 4, 5, 6, 7, 8, 9, 10, 11, 12, 13, 14, 15, 16, 17, 18, 19, or 20. In some embodiments, o is 9.

In some embodiments where one of $B^1$ and $B^2$ is CN and the other is C(=O)OR$^1$, the compounds of Formula (II) include the compounds of Formula IIa, IIb, IIc, IId, IIe, IIf, and IIg:

Formula IIa

Formula IIb

Formula IIc

Formula IId

Formula IIe

Formula IIf

Formula IIg and mixtures thereof.

In some of these embodiments, $R^1$ is H, $C_1$-$C_{30}$ alkyl, $C_1$-$C_{20}$ alkyl, or $C_1$-$C_{10}$ alkyl. In some exemplary embodiments, $R^1$ can include H, methyl, ethyl, propyl, butyl, pentyl, hexyl, heptyl, octyl, nonyl, or decyl. For example, $R^1$ can include, but is not limited to, H, methyl, ethyl, propyl, isopropyl, n-butyl, sec-butyl, isobutyl, tert-butyl, or 2-ethylhexyl.

In some of these embodiments, $R^2$ is H, $C_1$-$C_{30}$ alkyl, $C_1$-$C_{20}$ alkyl, or $C_1$-$C_{10}$ alkyl. In some exemplary embodiments, $R^2$ can include methyl, ethyl, propyl, butyl, pentyl, hexyl, heptyl, octyl, nonyl, or decyl. For example, $R^2$ can include, but is not limited to, H, methyl, ethyl, propyl, isopropyl, n-butyl, sec-butyl, isobutyl, tert-butyl, or 2-ethylhexyl.

In some exemplary embodiments where one of $B^1$ and $B^2$ is CN and the other is C(=O)OR$^1$, the compound of Formula (II) is selected from the group consisting of:

Formula IIai

Formula IIbi

Formula IIci
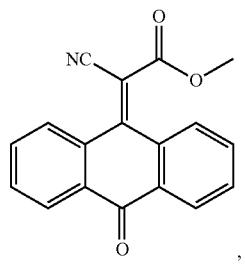
Formula IIdi
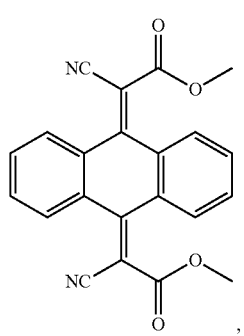
Formula IIei
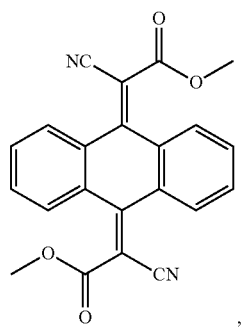
Formula IIfi
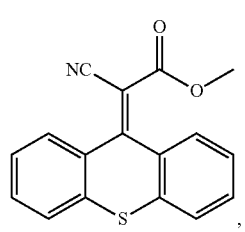
Formula IIgi
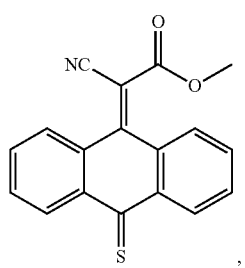
and mixtures thereof.
In some embodiments where both of $B^1$ and $B^2$ are C(=O)$OR^1$, the compounds of Formula (II) include the compounds of Formula IIh, IIi, IIj, IIk, IIl, IIm, and IIn:
Formula IIh
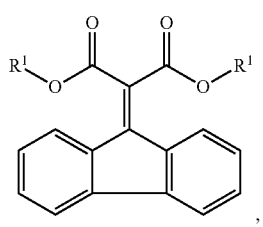
Formula IIi
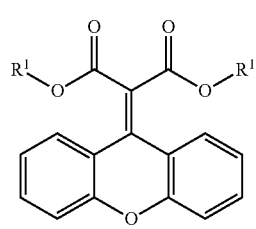
Formula IIj
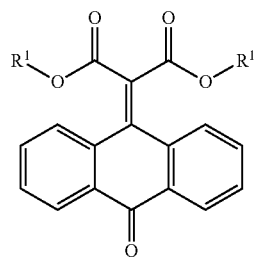
Formula IIk
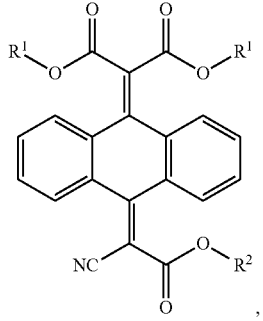
Formula IIl
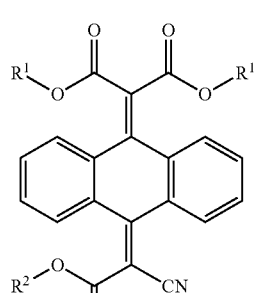
Formula IIm
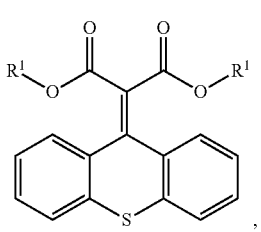

-continued

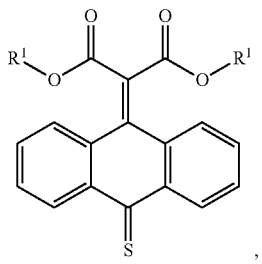

Formula IIn and mixtures thereof.

In some of these embodiments, $R^1$ is H, $C_1$-$C_{30}$ alkyl, $C_1$-$C_{20}$ alkyl, or $C_1$-$C_{10}$ alkyl. In some exemplary embodiments, $R^1$ can include H, methyl, ethyl, propyl, butyl, pentyl, hexyl, heptyl, octyl, nonyl, or decyl. For example, $R^1$ can include, but is not limited to, H, methyl, ethyl, propyl, isopropyl, n-butyl, sec-butyl, isobutyl, tert-butyl, or 2-ethylhexyl.

In some of these embodiments, $R^2$ is H, $C_1$-$C_{30}$ alkyl, $C_1$-$C_{20}$ alkyl, or $C_1$-$C_{10}$ alkyl. In some exemplary embodiments, $R^2$ can include H, methyl, ethyl, propyl, butyl, pentyl, hexyl, heptyl, octyl, nonyl, or decyl. For example, $R^2$ can include, but is not limited to, H, methyl, ethyl, propyl, isopropyl, or 2-ethylhexyl.

In some exemplary embodiments where both of $B^1$ and $B^2$ are C(=O)O$R^1$, the compound of Formula (II) is selected from the group consisting of:

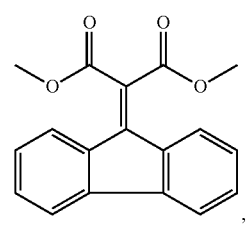

Formula IIhi

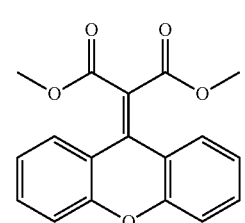

Formula IIii

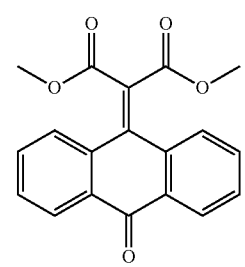

Formula IIji

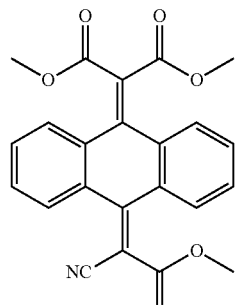

Formula IIki

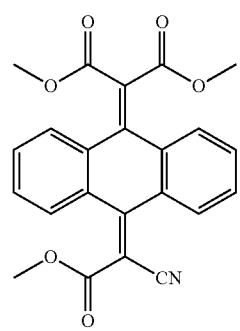

Formula IIli

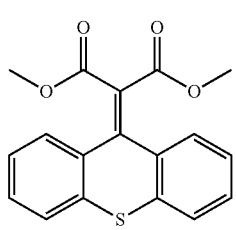

Formula IImi

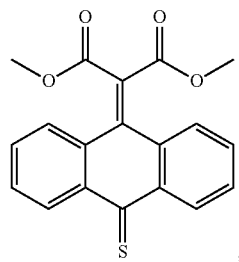

Formula IIni and mixtures thereof.

The photodegradable pigments described herein can include exogenous pigments, such as exogenous porphyrin compounds, or endogenous pigments, such as non-hematogenous pigments, hematogenous (i.e., blood derived) pigments, or mixtures thereof.

In some embodiments, the endogenous photodegradable pigment is a non-hematogenous pigment, such as, for example, melanins, flavins, pterins, urocanic acid.

In some of these embodiments, the photodegradable non-hematogenous pigment is a melanin, such as, for example, eumelanin, pheomelanin, neuromelanin, or mixtures thereof.

In some of these embodiments, the photodegradable non-hematogenous pigment is a flavin, such as, for example, riboflavin, flavin mononucleotide, a flavoprotein, flavin adenine dinucleotide.

In some of these embodiments, the photodegradable non-hematogenous pigment is a pterin, such as, for example, pteridine, biopterin, tetrahydrobiopterin, molybdopterin, cyanopterin, tetrahydromethanopterin, folic acid, and combinations thereof.

In some of these embodiments, the photodegradable non-hematogenous pigment is urocanic acid.

In some embodiments, the photodegradable endogenous pigment is a hematogenous pigment. The hematogenous pigment can include, for example, hemoglobin, bile pigments, porphyrins, and mixtures thereof.

In some embodiments, the photodegradable hematogenous pigment is hemoglobin.

In some embodiments, the photodegradable hematogenous pigment is a bile pigment. In some embodiments, the bile pigment is bilirubin, biliverdin, or a mixture thereof.

In some embodiments, the photodegradable hematogenous pigment is a porphyrin. In other embodiments, the pigment is an exogenous porphyrin. The porphyrin compounds described herein include a porphyrin moiety of Formula (I) or a derivative or tautomer thereof:

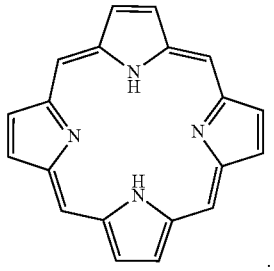
(I)

In some embodiments, the porphyrin moiety of Formula Ia is:

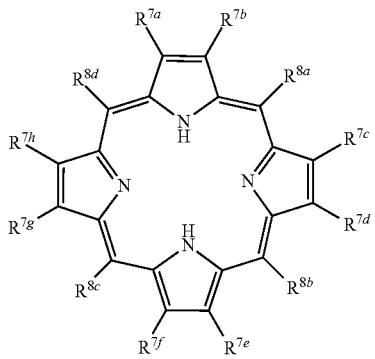

or a multimer thereof,
wherein:

$R^{7a}$, $R^{7b}$, $R^{7c}$, $R^{7d}$, $R^{7e}$, $R^{7f}$, $R^{7g}$, $R^{7h}$ are each independently selected from the group consisting of H, alkyl, alkenyl, alkynyl, hydroxyl, alkoxyl, carboxyl, carboxylic ester, amino, sulfhydryl, aryl, and heteroaryl; and, $R^{8a}$, $R^{8b}$, $R^{8c}$, $R^{8d}$, and $R^{8e}$ are each independently selected from the group consisting of H, alkyl, alkenyl, alkynyl, hydroxyl, alkoxyl, carboxyl, carboxylic ester, amino, sulfhydryl, aryl, and heteroaryl.

In some embodiments, $R^{7a}$, $R^{7b}$, $R^{7c}$, $R^{7d}$, $R^{7e}$, $R^{7f}$, $R^{7g}$, $R^{7h}$ are each independently selected from the group consisting of H, $C_1$-$C_6$ unsubstituted alkyl, $C_1$-$C_6$ hydroxyalkyl, $C_1$-$C_6$ carboxyalkyl, $C_1$-$C_6$ esteralkyl, $C_1$-$C_6$ sulfhydrylalkyl $C_1$-$C_6$ alkenyl, amino, aryl, and heteroaryl.

In some exemplary embodiments, $R^{7a}$, $R^{7b}$, $R^{7c}$, $R^{7d}$, $R^{7e}$, $R^{7f}$, $R^{7g}$, $R^{7h}$ are each independently selected from the group consisting of H, $C_1$-$C_4$ unsubstituted alkyl, $C_1$-$C_4$ hydroxyalkyl, $C_1$-$C_4$ carboxyalkyl, $C_1$-$C_4$ esteralkyl, $C_1$-$C_6$ sulfhydrylalkyl, $C_1$-$C_4$ alkenyl, aryl, and heteroaryl. For example, $R^{7a}$, $R^{7b}$, $R^{7c}$, $R^{7d}$, $R^{7e}$, $R^{7f}$, $R^{7g}$, $R^{7h}$ can each independently be selected from the group consisting of H, methyl, ethyl, propyl, isopropyl, n-butyl, sec-butyl, iso-butyl, tert-butyl, ethenyl, 1-propenyl, 2-propenyl, 1-hydroxyethyl, 2-hydroxyethyl, phenyl, acetic acid, methyl acetate, ethyl acetate, propionic acid, methyl propanate, ethylpropanate, and

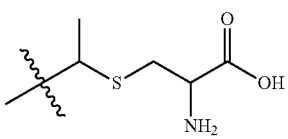

In some embodiments, $R^{8a}$, $R^{8b}$, $R^{8c}$, $R^{8d}$, and $R^{8e}$ are each independently selected from the group consisting of H, $C_1$-$C_6$ alkyl, $C_1$-$C_6$ alkenyl, aryl, and heteroaryl. In some exemplary embodiments, $R^{8a}$, $R^{8b}$, $R^{8c}$, $R^{8d}$, and $R^{8e}$ are each independently selected from the group consisting of H, $C_1$-$C_4$ alkyl, $C_1$-$C_4$ alkenyl, phenyl, naphthyl, and pyridyl. For example, $R^{8a}$, $R^{8b}$, $R^{8c}$, $R^{8d}$, and $R^{8e}$ can each independently be selected from the group consisting of H, phenyl, hydroxyphenyl, dihydroxyphenyl, trihydroxyphenyl, methoxyphenyl, dimethoxyphenyl, trimethoxyphenyl, carboxyphenyl, trimethylanilinium, naphthyl, sulfonatophenyl, pyridyl, and N-methylpyridyl.

In some embodiments, $R^{7a}$, $R^{7b}$, $R^{7c}$, $R^{7d}$, $R^{7e}$, $R^{7f}$, $R^{7g}$, $R^{7h}$ are each independently selected from the group consisting of H, alkyl, alkenyl, alkynyl, hydroxyl, alkoxyl, carboxyl, carboxylic ester, amino, sulfhydryl, aryl, and heteroaryl; and $R^{8a}$, $R^{8b}$, $R^{8c}$, $R^{8d}$, and $R^{8e}$ are each independently selected from the group consisting of H, alkyl, alkenyl, alkynyl, hydroxyl, alkoxyl, carboxyl, carboxylic ester, amino, sulfhydryl, aryl, and heteroaryl.

In other embodiments, $R^{7a}$, $R^{7b}$, $R^{7c}$, $R^{7d}$, $R^{7e}$, $R^{7f}$, $R^{7g}$, $R^{7h}$ are each independently selected from the group consisting of H, $C_1$-$C_6$ unsubstituted alkyl, $C_1$-$C_6$ hydroxyalkyl, $C_1$-$C_6$ carboxyalkyl, $C_1$-$C_6$ esteralkyl, $C_1$-$C_6$ sulfhydrylalkyl $C_1$-$C_6$ alkenyl, amino, aryl, and heteroaryl; and $R^{8a}$, $R^{8b}$, $R^{8c}$, $R^{8d}$, and $R^{8e}$ are each independently selected from the group consisting of H, $C_1$-$C_6$ alkyl, $C_1$-$C_6$ alkenyl, aryl, and heteroaryl.

In yet other embodiments, $R^{7a}$, $R^{7b}$, $R^{7c}$, $R^{7d}$, $R^{7e}$, $R^{7f}$, $R^{7g}$, $R^{7h}$ are each independently selected from the group consisting of H, $C_1$-$C_4$ unsubstituted alkyl, $C_1$-$C_4$ hydroxyalkyl, $C_1$-$C_4$ carboxyalkyl, $C_1$-$C_4$ esteralkyl, $C_1$-$C_6$ sulfhydrylalkyl, $C_1$-$C_4$ alkenyl, aryl, or heteroaryl; and $R^{8a}$, $R^{8b}$, $R^{8c}$, $R^{8d}$, and $R^{8e}$ are each independently selected from the group consisting of H, $C_1$-$C_4$ alkyl, $C_1$-$C_4$ alkenyl, phenyl, naphthyl, and pyridyl.

In still other embodiments, $R^{7a}$, $R^{7b}$, $R^{7c}$, $R^{7d}$, $R^{7e}$, $R^{7f}$, $R^{7g}$, $R^{7h}$ are each independently selected from the group consisting of H, methyl, ethyl, propyl, isopropyl, n-butyl, sec-butyl, iso-butyl, tert-butyl, ethenyl, 1-propenyl, 2-propenyl, 1-hydroxyethyl, 2-hydroxyethyl, phenyl, acetic acid, methyl acetate, ethyl acetate, propionic acid, methyl propanate, ethylpropanate, and

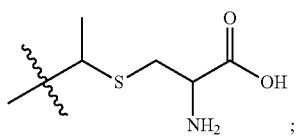

and $R^{8a}$, $R^{8b}$, $R^{8c}$, $R^{8d}$, and $R^{8e}$ are each independently selected from the group consisting of H, phenyl, hydroxyphenyl, dihydroxyphenyl, trihydroxyphenyl, methoxyphenyl, dimethoxyphenyl, trimethoxyphenyl, carboxyphenyl, trimethylanilinium, naphthyl, sulfonatophenyl, pyridyl, and N-methylpyridyl.

All porphyrin compounds that are excited by visible light are returned to their ground state by the conjugated fused tricyclic compounds having electron withdrawing groups described herein. The porphyrin compounds include, but are not limited to, 5-azaprotoporphyrin IX, bis-porphyrin, coproporphyrin III, deuteroporphyrin, deuteroporphyrin IX dichloride, diformyl deuteroprophyrin IX, dodecaphenylporphyrin, hematoporphyrin, hematoporphyrin IX, hematoporphyrin monomer, hematoporphyrin dimer, hematoporphyrin derivative, hematoporphyrin derivative A, hematoporphyrin IX dihydrochloride, hematoporphyrin dihydrochloride, mesoporphyrin, mesoporphyrin IX, monohydroxyethylvinyl deuteroporphyrin, 5,10,15,20-tetra(o-hydroxyphenyl)porphyrin, 5,10,15,20-tetra(m-hydroxyphenyl)porphyrin, 5,10,15,20-tetra(p-hydroxyphenyl) porphyrin, 5,10,15,20-tetrakis(3-methoxyphenyl)-porphyrin, 5,10,15,20-tetrakis(3,4-dimethoxyphenyl)porphyrin, 5,10,15,20-tetrakis(3,5-dimethoxyphenyl)porphyrin, 5,10,15,20-tetrakis(3,4,5-trimethoxyphenyl)porphyrin, 2,3,7,8,12,13,17,18-octaethyl-5,10,15,20-tetraphenylporphyrin, porphyrin c, protoporphyrin, protoporphyrin IX, tetra-(4-N-carboxyphenyl)-porphine, tetra-(3-methoxyphenyl)-porphine, tetra-(3-methoxy-2,4-difluorophenyl)-porphine, 5,10,15,20-tetrakis(4-N-methylpyridyl)porphine, tetra-(4-N-methylpyridyl)-porphine tetrachloride, tetra-(3-N-methylpyridyl)-porphine, tetra-(2-N-methylpyridyl)-porphine, tetra(4-N,N,N-trimethylanilinium)porphine, tetra-(4-N,N,N''-trimethylamino-phenyl)porphine tetrachloride, tetranaphthaloporphyrin, tetraphenylporphyrin, tetra-(4-sulfonatophenyl)-porphine, 4-sulfonatophenylporphine, uroporphyrin, uroporphyrin III, uroporphyrin IX, and uroporphyrin I, and esters thereof.

In some embodiments, the porphyrin compound is an ester selected from the group consisting of 5-azaprotoporphyrin dimethylester, coproporphyrin III tetramethylester, deuteroporphyrin IX dimethylester, diformyl deuteroporphyrin IX dimethylester, hematoporphyrin IX dimethylester, mesoporphyrin dimethylester, mesoporphyrin IX dimethylester, monoformyl-monovinyl-deuteroporphyrin IX dimethylester, protoporphyrin dimethylester, and protoporphyrin IX dimethylester.

In some exemplary embodiments, the porphyrin compound is selected from the group consisting of coproporphyrin III, coproporphyrin III tetramethylester, deuteroporphyrin, deuteroporphyrin IX dichloride, deuteroporphyrin IX dimethylester, hematoporphyrin, hematoporphyrin IX, hematoporphyrin derivative, hematoporphyrin derivative A, hematoporphyrin IX dihydrochloride, hematoporphyrin dihydrochloride, hematoporphyrin IX dimethylester, mesoporphyrin, mesoporphyrin dimethylester, mesoporphyrin IX, mesoporphyrin IX dimethylester, protoporphyrin, protoporphyrin IX, protoporphyrin dimethylester, protoporphyrin IX dimethylester, uroporphyrin, uroporphyrin III, uroporphyrin IX, and uroporphyrin I.

For example, the porphyrin compound can include protoporphyrin IX, deuteroporphyrin IX dichloride, deuteroporphyrin IX dimethylester, hematoporphyrin, hematoporphyrin IX, hematoporphyrin derivative, mesoporphyrin dimethylester, mesoporphyrin IX, or mesoporphyrin IX dimethylester.

In some embodiments, the porphyrin compound exists as a free base. In other embodiments, the porphyrin compound is chelated to a metal. In some embodiments, the metal has a 2+ or 3+ oxidation state. In some embodiments, the metal can include, for example, beryllium, magnesium, aluminum, calcium, strontium, barium, radium, scandium, titanium, vanadium, chromium, manganese, iron, cobalt, nickel, copper, zinc, gallium, yttrium, zirconium, niobium, molybdenum, technetium, ruthenium, rhodium, palladium, silver, cadmium, indium, tin, lead, and platinum.

A particularly useful porphyrin compound is protoporphyrin IX having the structure (Ib):

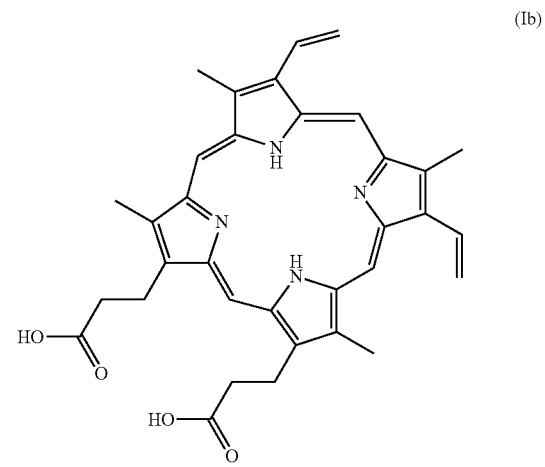 [SMILES: C=CC1=C(C)c2cc3[nH]c(cc4nc(cc5[nH]c(cc1n2)c(C)c5CCC(=O)O)C(CCC(=O)O)=C4C)c(C)c3C=C]

Thus, one aspect provides a method of quenching excited state energy from an photodegradable pigment compound that has been excited by absorption of light having a wavelength in the wavelength range of about 290 to about 800 nm, comprising reacting the pigment compound with a conjugated fused tricyclic compound having electron withdrawing groups of Formula (II) or a salt thereof:

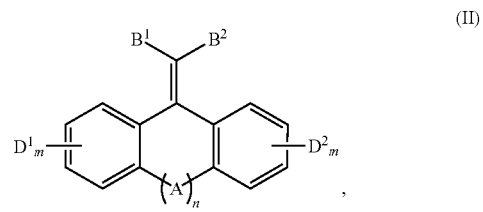

as previously defined above.

In some exemplary embodiments of this aspect, the photodegradable pigment compound includes a porphyrin compound comprising a porphyrin moiety of Formula (I) or a derivative or tautomer thereof:

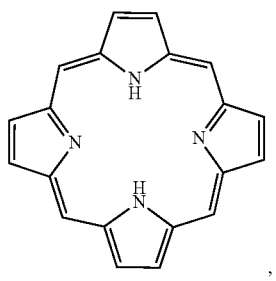

(I)

as previously defined above.

Another aspect provides a method of suppressing the generation of singlet oxygen by an excited pigment when a mammalian-contained pigment is exposed to light, thereby exciting the pigment to an excited state, by quenching the excited state of the pigment compound with a conjugated fused tricyclic compound having electron withdrawing groups of Formula (II) or a salt thereof:

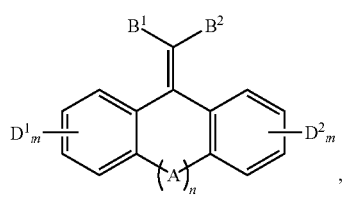

(II)

as previously defined above.

In some exemplary embodiments of this aspect, the pigment compound includes a porphyrin compound comprising a porphyrin moiety of Formula (I) or a derivative or tautomer thereof:

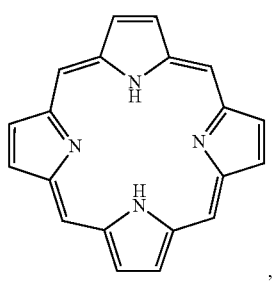

(I)

as previously defined above.

Yet another aspect provides a method of protecting skin from oxidative stress caused by the generation of free radical oxygen comprising contacting, preferably coating the skin with an pigment excited state quencher capable of accepting or donating an electron from or to an pigment compound in the excited state and returning the excited pigment compound to its ground state, said pigment quencher comprising a conjugated fused tricyclic compound having electron withdrawing groups of Formula (II) or a salt thereof:

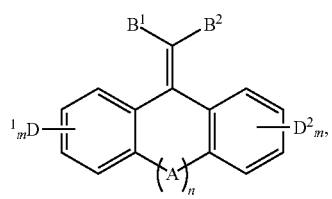

(II)

as previously defined above.

In some exemplary embodiments of this aspect, the pigment compound includes a porphyrin compound comprising a porphyrin moiety of Formula (I) or a derivative or tautomer thereof:

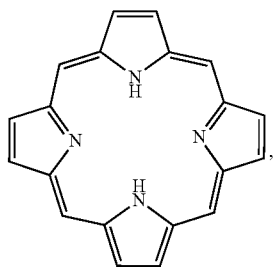

(I)

as previously defined above.

Still another aspect provides a method of protecting healthy cells adjacent to cancerous or pre-cancerous cells undergoing photodynamic therapy comprising applying a coating composition containing a pigment excited state quencher compound to said adjacent cells to reduce the generation of free radical oxygen and other reactive oxygen species from said healthy cells while the photodynamic therapy generates free radical oxygen from said cancerous or pre-cancerous cells, with a conjugated fused tricyclic compound having electron withdrawing groups of Formula (II) or a salt thereof:

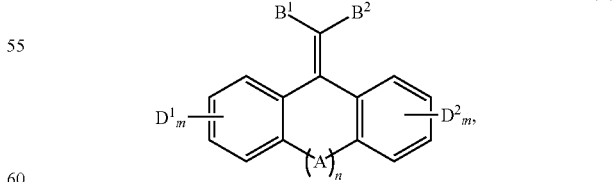

(II)

as previously defined above.

In some exemplary embodiments of this aspect, the pigment compound includes a porphyrin compound comprising a porphyrin moiety of Formula (I) or a derivative or tautomer thereof:

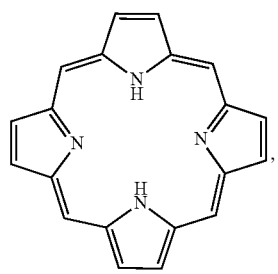

(I)

as previously defined above.

In accordance with one important embodiment, a conjugated fused tricyclic compound having electron withdrawing groups of Formula (II), IIa, IIb, IIc, IId, IIe, IIf, IIg, IIh, IIi, IIj, IIk, IIl, IIm, IIn, or a combination thereof is included in a cosmetic or dermatological composition for contacting, and preferably coating a skin surface to protect the skin from contacting damaging amounts of singlet oxygen and other reactive oxygen species which, without the presence of the conjugated fused tricyclic compound having electron withdrawing groups, would be generated when skin cell-contained or blood-contained porphyrin compounds, particularly protoporphyrin IX, are exposed to sunlight, or other visible light. In another embodiment, the cosmetic or dermatological composition can also include a UVA filter and/or UVB filter compound and/or a broad-band filter compound for protection of the skin from UVA and/or UVB wavelengths.

The conjugated fused tricyclic compounds having electron withdrawing groups of Formula (II) can be used to suppress the generation of other reactive oxygen species or radical compounds. Some of these reactive oxygen species include, for example, free radical oxygen, superoxide anion, peroxide, hydroxyl radical, and hydroxyl ion. It should be understood that throughout this disclosure whenever singlet state oxygen or free radical oxygen is described as being suppressed, these other oxygen species also may be suppressed.

The conjugated fused tricyclic compound having electron withdrawing groups of Formula (II) can be included in the cosmetic or dermatological composition in an amount of about 0.01% by weight to about 20% by weight, preferably from about 0.1 to about 20% by weight, more preferably from about 0.1% to about 10% by weight, in each case based on the total weight of the composition.

The total amount of one or more water-soluble UV filter substances in the finished cosmetic or dermatological compositions is advantageously chosen from the range of about 0.01% by weight to about 20% by weight, preferably from about 0.1% to about 20% by weight, more preferably from about 0.1% to about 10% by weight, in each case based on the total weight of the composition.

Preferred UV filter compounds, and photostabilizers for the UV filter compounds, are disclosed in published PCT application WO 2009/020676, hereby incorporated by reference for preferred water-soluble, organic and particulate UV filter compounds.

In some embodiments, the UV filter compound is a benzotriazole compound having the structure

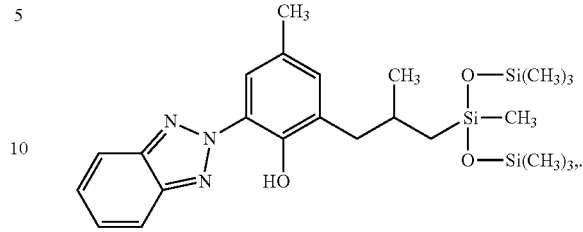

The cosmetic or dermatological compositions can include an additional photoactive compound. In some embodiments, the additional photoactive compound is selected from the group consisting of p-aminobenzoic acid and salts and derivatives thereof; anthranilate and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naphtholsulfonate and salts and derivatives thereof; benzalacetophenone naphtholsulfonate and salts and derivatives thereof; dihydroxy-naphthoic acid and salts thereof; o-hydroxydiphenyldisulfonate and salts and derivatives thereof; p-hydroxydiphenyldisulfonate and salts and derivatives thereof; coumarin and derivatives thereof; diazole derivatives; quinine derivatives and salts thereof; quinoline derivatives; hydroxyl-substituted benzophenone derivatives; naphthalate derivatives; methoxy-substituted benzophenone derivatives; uric acid derivatives; vilouric acid derivatives; tannic acid and derivatives thereof; hydroquinone; benzophenone derivatives; 1,3,5-triazine derivatives; phenyldibenzimidazole tetrasulfonate and salts and derivatives thereof; terephthalylidene dicamphor sulfonic acid and salts and derivatives thereof; methylene bis-benzotriazolyl tetramethylbutylphenol and salts and derivatives thereof; bis-ethylhexyloxyphenol methoxyphenyl triazine and salts, diethylamino hydroxyl benzoyl and derivatives thereof; and combinations of the foregoing.

The cosmetic or dermatological composition may include a cinnamate ester, such as 2-ethylhexyl p-methoxycinnamate, isoamyl p-methoxycinnamate, and a combination thereof. For example, the cinnamate ester can be 2-ethylhexyl p-methoxycinnamate. In some of these embodiments, the cinnamate ester is present in the composition in an amount in a range of about 0.1 wt. % to about 15 wt. %, based on the total weight of the composition.

The cosmetic or dermatological composition also may include about 0.1 to about 10 wt. % of a triplet quencher selected from the group consisting of octocrylene, methyl benzylidene camphor, diethylhexyl 2,6-naphthalate, and combinations thereof.

The cosmetic or dermatological composition also may include about 0.1 to about 10 wt. % of a singlet quencher such as an alkoxy crylene (e.g., ethylhexyl methoxy crylene), a copolymer of adipic acid and neopentyl glycol that is terminated with cyanodiphenyl propenoic acid, and mixtures thereof.

The cosmetic or dermatological compositions may have conventional additives and solvents used for the treatment, care and cleansing of skin and/or the hair and as a make-up product in decorative cosmetics.

For use in protecting skin from oxidative stress, the cosmetic and/or dermatological compositions can contain about 0.01 wt. % to about 20 wt. % conjugated fused tricyclic compound(s) having electron withdrawing groups and the composition is applied to the skin and/or the hair in a sufficient quantity in the manner customary for cosmetics.

The cosmetic and dermatological compositions described herein can comprise cosmetic auxiliaries such as those conventionally used in such preparations, e.g. preservatives, bactericides, perfumes, antifoams, dyes, pigments which have a coloring effect, thickeners, moisturizers and/or humectants, fats, oils, waxes or other conventional constituents of a cosmetic or dermatological composition, such as alcohols, polyols, polymers, foam stabilizers, electrolytes, organic solvents or silicone derivatives.

An additional content of antioxidants is generally preferred. According to the invention, favorable antioxidants which can be used are any antioxidants suitable or conventional for cosmetic and/or dermatological applications.

The antioxidants are particularly advantageously chosen from the group consisting of amino acids (e.g. glycine, histidine, tyrosine, tryptophan) and derivatives thereof, imidazoles (e.g. urocanic acid) and derivatives thereof, peptides such as D,L-camosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, .gamma.-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine sulfoximine, buthionine sulfones, penta-, hexa-, heptathionine sulfoximine) in very low tolerated doses (e.g. pmol to μmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. .gamma.-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of gum benzoin, rutinic acid and derivatives thereof, α-glycosylrutin, ferulic acid, furfurylideneglucitol, carnosine, butylhydroxytoluene, butylhydroxyanisole, nordihydroguaiaretic acid, trihydroxybutyro-phenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention.

Thus, in some embodiments, the cosmetic or dermatological composition can include one or more oxidation-sensitive or UV-sensitive ingredients selected from the group consisting of retinoid compounds, carotenoid compounds, lipoic acid and derivatives thereof, vitamin E and derivatives thereof, vitamin F and derivatives thereof, and dioic acid in an amount from about 0.0001 wt % to about 10 wt %, based on the total weight of the composition.

Advantageous hydrophilic active ingredients which (individually or in any combinations with one another) are stabilized by their use together with one or more conjugated fused tricyclic compounds having electron withdrawing groups include those listed below: biotin; carnitine and derivatives; creatine and derivatives; folic acid; pyridoxine; niacinamide; polyphenols (in particular flavonoids, very particularly alpha-glucosylrutin); ascorbic acid and derivatives; Hamamelis; Aloe Vera; panthenol; and amino acids.

Particularly advantageous hydrophilic active ingredients for the purposes of the present invention are also water-soluble antioxidants, such as, for example, vitamins.

The amount of hydrophilic active ingredients (one or more compounds) in the compositions is preferably about 0.0001% to about 10% by weight, particularly preferably about 0.001% to about 5% by weight, based on the total weight of the composition.

Particularly advantageous compositions are also obtained when antioxidants are used as additives or active ingredients. According to the invention, the cosmetic or dermatological compositions advantageously comprise one or more antioxidants. Favorable, but nevertheless optional antioxidants which may be used are all antioxidants customary or suitable for cosmetic and/or dermatological applications.

The amount of antioxidants (one or more compounds) in the compositions is preferably about 0.001% to about 30% by weight, particularly preferably about 0.05% to about 20% by weight, in particular about 0.1% to about 10% by weight, based on the total weight of the composition.

If vitamin E and/or derivatives thereof are the antioxidant or antioxidants, it is advantageous to choose their respective concentrations from the range from about 0.001% to about 10% by weight, based on the total weight of the composition.

If vitamin A or vitamin A derivatives, or carotenes or derivatives thereof are the antioxidant or antioxidants, it is advantageous to choose their respective concentrations from the range from about 0.001% to about 10% by weight, based on the total weight of the composition.

It is particularly advantageous when the cosmetic or dermatological compositions, according to the present invention, comprise further cosmetic or dermatological active ingredients, preferred active ingredients being additional antioxidants which can further protect the skin against additional oxidative stress.

Advantageous further active ingredients are natural active ingredients and/or derivatives thereof, such as e.g. ubiquinones, retinoids, carotenoids, creatine, taurine and/or β-alanine.

Compositions according to the invention, which comprise e.g. known antiwrinkle active ingredients, such as flavone glycosides (in particular α-glycosylrutin), coenzyme Q10, vitamin E and/or derivatives and the like, are particularly advantageously suitable for the prophylaxis and treatment of cosmetic or dermatological changes in skin, as arise, for example, during skin aging (such as, for example, dryness, roughness and formation of dryness wrinkles, itching, reduced refatting (e.g. after washing), visible vascular dilations (teleangiectases, couperosis), flaccidity and formation of wrinkles and lines, local hyperpigmentation, hypopigmentation and abnormal pigmentation (e.g. age spots), increased susceptibility to mechanical stress (e.g. cracking) and the like). In addition, they are advantageously suitable against the appearance of dry or rough skin.

The cosmetic or dermatological compositions can include triazines, benzotriazoles, latex particles, organic pigments, inorganic pigments, and mixtures thereof.

Preferred particulate UV filter substances for the purposes of the present invention are inorganic pigments, especially metal oxides and/or other metal compounds which are slightly soluble or insoluble in water, especially oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals, and mixtures of such oxides, and the sulfate of barium ($BaSO_4$).

Zinc oxides for the purposes of the present invention may also be used in the form of commercially available oily or aqueous predispersions. Zinc oxide particles and predispersions of zinc oxide particles which are suitable according to the invention are distinguished by a primary particle size of <300 nm and can be obtained under the following proprietary names from the stated companies:

| Proprietary name | Coating | Manufacturer |
| --- | --- | --- |
| Z-Cote HP1 | 2% Dimethicone | BASF |
| Z-Cote | / | BASF |
| ZnO NDM | 5% Dimethicone | H&R |
| ZnO Neutral | / | H&R |
| MZ-300 | / | Tayca Corporation |
| MZ-500 | / | Tayca Corporation |
| MZ-700 | / | Tayca Corporation |
| MZ-303S | 3% Methicone | Tayca Corporation |
| MZ-505S | 5% Methicone | Tayca Corporation |
| MZ-707S | 7% Methicone | Tayca Corporation |
| MZ-303M | 3% Dimethicone | Tayca Corporation |
| MZ-505M | 5% Dimethicone | Tayca Corporation |
| MZ-707M | 7% Dimethicone | Tayca Corporation |
| Z-Sperse Ultra | ZnO (>=56%)/Ethylhexyl Hydroxystearate Benzoate/ Dimethicone/Cyclomethicone | Collaborative Laboratories |
| Samt-UFZO-450/D5 (60%) | ZnO (60%)/Cyclomethicone/ Dimethicone | Miyoshi Kasei |

Particularly preferred zinc oxides for the purposes of the invention are Z-Cote HP1 and Z-Cote from BASF and zinc oxide NDM from Haarmann & Reimer.

Titanium dioxide pigments of the invention may be in the form of both the rutile and anatase crystal modification and may for the purposes of the present invention advantageously be surface-treated ("coated"), the intention being for example to form or retain a hydrophilic, amphiphilic or hydrophobic character. This surface treatment may consist of providing the pigments by processes known per se with a thin hydrophilic and/or hydrophobic inorganic and/or organic layer. The various surface coatings may for the purposes of the present invention also contain water.

Inorganic surface coatings for the purposes of the present invention may consist of aluminum oxide ($Al_2O_3$), aluminum hydroxide $Al(OH)_3$ or aluminum oxide hydrate (also: alumina, CAS No.: 1333-84-2), sodium hexametaphosphate ($NaPO_3)_6$, sodium metaphosphate $(NaPO_3)_n$, silicon dioxide ($SiO_2$) (also: silica, CAS No.: 7631-86-9), or iron oxide ($Fe_2O_3$). These inorganic surface coatings may occur alone, in combination and/or in combination with organic coating materials.

Organic surface coatings for the purposes of the present invention may consist of vegetable or animal aluminum stearate, vegetable or animal stearic acid, lauric acid, dimethylpolysiloxane (also: dimethicones), methylpolysiloxane (methicones), simethicones (a mixture of dimethylpolysiloxane with an average chain length of from about 200 to about 350 dimethylsiloxane units and silica gel) or alginic acid. These organic surface coatings may occur alone, in combination and/or in combination with inorganic coating materials.

Coated and uncoated titanium dioxides may be used in the form of commercially available oily or aqueous predispersions. It may be advantageous to add dispersion aids and/or solubilization mediators.

Suitable titanium dioxide particles and predispersions of titanium dioxide particles for addition to the compositions described herein are obtainable under the following proprietary names from the stated companies:

| Proprietary name | Coating | Additional ingredients of the predispersion | Manufacturer |
| --- | --- | --- | --- |
| MT-150W | None | — | Tayca Corporation |
| MT-150A | None | — | Tayca Corporation |
| MT-500B | None | — | Tayca Corporation |
| MT-600B | None | — | Tayca Corporation |
| MT-100TV | Aluminum hydroxide Stearic acid | — | Tayca Corporation |
| MT-100Z | Aluminum hydroxide Stearic acid | — | Tayca Corporation |
| MT-100T | Aluminum hydroxide Stearic acid | — | Tayca Corporation |
| MT-500T | Aluminum hydroxide Stearic acid | — | Tayca Corporation |
| MT-100S | Aluminum hydroxide Lauric acid | — | Tayca Corporation |
| MT-100F | Stearic acid Iron oxide | — | Tayca Corporation |
| MT-100SA | Alumina Silica | — | Tayca Corporation |
| MT-500SA | Alumina Silica | — | Tayca Corporation |
| MT-600SA | Alumina Silica | — | Tayca Corporation |
| MT-100SAS | Alumina Silica Silicone | — | Tayca Corporation |

-continued

| Proprietary name | Coating | Additional ingredients of the predispersion | Manufacturer |
|---|---|---|---|
| MT-500SAS | Alumina Silica Silicone | — | Tayca Corporation |
| MT-500H | Alumina | — | Tayca Corporation |
| MT-100AQ | Silica Aluminum hydroxide Alginic acid | — | Tayca Corporation |
| Eusolex T | Water Simethicone | — | Merck KgaA |
| Eusolex T-2000 | Alumina Simethicone | — | Merck KgaA |
| Eusolex T-Olio F | Silica Dimethylsilate Water | $C_{12-15}$ Alkylbenzoate Calcium Polyhydroxystearate Silica Dimethylsilate | Merck KgaA |
| Eusolex T-Olio P | Water Simethicone | Octyl Palmitate PEG-7 Hydrogenated Castor Oil Sorbitan Oleate Hydrogenated Castor Oil Beeswax Stearic acid | Merck KgaA |
| Eusolex T-Aqua | Water Alumina Sodium metaphosphate | Phenoxyethanol Sodium Methylparabens Sodium metaphosphate | Merck KgaA |
| Eusolex T-45D | Alumina Simethicone | Isononyl Isononanuate Polyglyceryl Ricinoleate | Merck KgaA |
| Kronos 1171 (Titanium dioxide 171) | None | — | Kronos |
| Titanium dioxide P25 | None | — | Degussa |
| Titanium dioxide T805 | Octyltri- methylsilane (Uvinul $TiO_2$) | — | Degussa |
| UV-Titan X610 | Alumina Dimethicone | — | Kemira |
| UV-Titan X170 | Alumina Dimethicone | — | Kemira |
| UV-Titan X161 | Alumina Silica Stearic acid | — | Kemira |
| UV-Titan M210 | Alumina | — | Kemira |
| UV-Titan M212 | Alumina | Glycerol | Kemira |
| UV-Titan M262 | Alumina Silicone | — | Kemira |
| UV-Titan M160 | Alumina Silica Stearic acid | — | Kemira |
| Tioveil AQ 10PG | Alumina Silica | Water Propylene glycol | Solaveil Uniquema |
| Mirasun TiW 60 | Alumina Silica | Water | Rhone-Poulenc |

Preferred titanium dioxides are distinguished by a primary particle size between about 10 nm to about 150 nm.

Titanium dioxides particularly preferred for the compositions described herein are MT-100 Z and MT-100 TV from Tayca Corporation, Eusolex T-2000 from Merck and titanium dioxide T 805 from Degussa.

Further advantageous pigments are latex particles. Latex particles which are advantageously included in the compositions described herein are described in the following publications: U.S. Pat. No. 5,663,213 and EP 0 761 201. Particularly advantageous latex particles are those formed from water and styrene/acrylate copolymers and available for example under the proprietary name "Alliance Sun-Sphere" from Rohm & Haas.

An advantageous organic pigment for addition to the compositions described herein is 2,2'-methylenebis(6-(2H-benzotriazol-2-yl)-4-(1,1,3,3-tetramethylbutyl-)phenol) (INCI: bis-octyltriazol), which is obtainable under the proprietary name Tinosorb® M from CIBA-Chemikalien GmbH.

Examples

Initially planned experiments involved the effects of the photoprotecting conjugated fused tricyclic compounds having electron withdrawing groups of Formula (II) and the alkoxy crylene photostabilizer in the examples of this assignee's U.S. Pat. No. 7,597,825 (hereby incorporated by reference in its entirety) on singlet oxygen generation from the following photosensitizers: protoporphyrin IX; riboflavin; retinol; ADMHP; and melanin after UV light exposure (355 nm). The hypothesis is that the compound of Formula (II) and the alkoxy crylene photostabilizers disclosed in the examples of this assignee's U.S. Pat. No. 7,597,825 act as excited state quenchers for porphyrin compounds and subsequently should prevent or significantly reduce singlet oxygen formation when the porphyrin compounds are exposed to light.

UV and visible light absorption spectra were recorded to investigate to what extent the stabilizers itself absorb UV light. FIG. 1 reveals that the stabilizers are strong UV absorbers with large extinction coefficients (molar absorptivity) of 16,200 M−1 cm−1 (RX-13949; λmax=334 nm) and 13,200 M−1 cm−1 (SolaStayS1; λmax=336 nm). The compound with the oxygen bridge (Formula IIbi) caused a bathocromic shift of the UV absorption of the lowest energy band. The compound with the sulfur bridge (Formula IIfi) shifted the lowest energy band further into the visible region.

Because of the strong absorption of the two compounds at 355 nm, the initially selected excitation wavelength for the sensitizers for the planned singlet oxygen experiments, the stabilizers would compete for the excitation photons of the excited porphyrin compound. This would lead to a reduced singlet oxygen generation from the sensitizers, but not by excited state quenching of the sensitizers by the stabilizers. To perform meaningful experiments, the sensitizer needs to be excited at a wavelength where the two compounds do not absorb. Protoporphyrin IX has weak absorption bands above 450 nm, where the two compounds are transparent (FIG. 2).

Photoexcitation in these absorption bands generates singlet excited states which deactivate to the ground state or intersystem cross to the triplet state. The two compounds could target the singlet excited states and/or the triplet states. Fluorescence lifetime measurements are a convenient way to measure singlet state quenching by the stabilizers (see this assignee's U.S. Pat. No. 7,776,614). Protoporphyrin IX decay traces were recorded in the absence and presence of difference of the two compounds (FIG. 3). The experiments show that the compound of Formula IIai significantly quenches the protoporphyrin IX fluorescence (reduces fluorescence lifetime; FIG. 3). However, the alkoxy crylene compound of U.S. Pat. No. 7,597,825 caused no reduction in fluorescence lifetime, even at high concentrations, such as 0.1 M (FIG. 3).

Figure 4B:
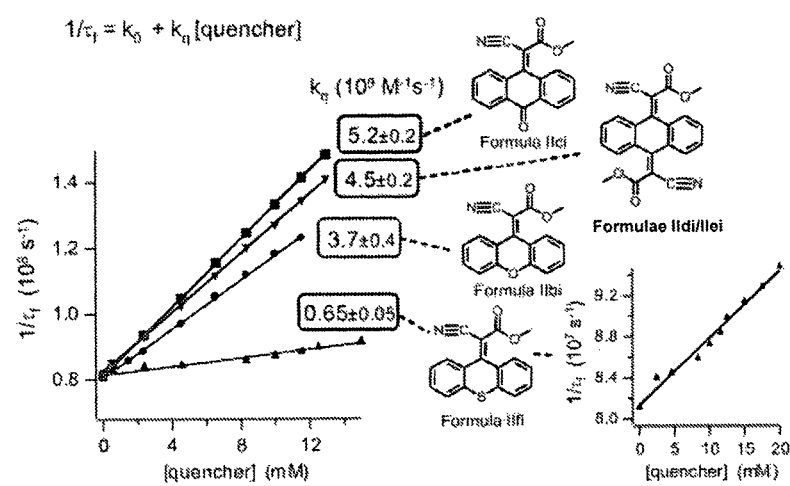
FIG. 4 is a graph showing the determination of $k_q$, the bimolecular rate constant for quenching of protoporphyrin IX fluorescence by Formula IIai and alkoxy crylene using the experimental data shown in FIG. 3 (FIG. 4a), and Formula IIbi, IIci, a mixture of IIdi and IIei, and IIfi (FIG. 4b). The graphs depict inverse fluorescence lifetime vs. quencher (stabilizer) concentration.

Data, such as the collected data shown in FIG. 3, were used to determine the bimolecular quenching rate constant for singlet excited state quenching by alkoxy crylene and compounds IIai, IIbi, IIci, a mixture of IIdi and IIei, and IIfi. The quenching rate constant can be directly extracted from the slope of the plot of the inverse fluorescence lifetime vs. the concentration of the two compounds (FIG. 4). The data reveal a high quenching rate constant with the compound of Formula IIai, IIbi, IIci, and the mixture of IIdi and IIei (close to the diffusion limit) but no observable quenching with the alkoxy crylene compound.

To investigate if triplet states of protoporphyrin IX are quenched, laser flash photolysis experiments were performed. In these experiments, a deoxygenated acetonitrile solution of protoporphyrin IX is excited with short laser pulses from a Nd-YAG laser (355 nm, 5 ns pulse width). Difference absorption kinetic traces were recorded at different observation wavelength (300 to 800 nm) and from these a transient absorption spectrum was constructed (FIG. 5a). This difference spectrum shows ground state depletion at 400 nm (where protoporphyrin IX absorbs strongly; see FIG. 2). In addition, two bands are observed at 320 and 440 nm, which are assigned to the triplet-triplet absorption of protoporphyrin IX. The triplet absorption decayed with a lifetime of 52 μs with subsequent recovery of the ground state absorption (FIGS. 5b and c, respectively).

Figure 6B:
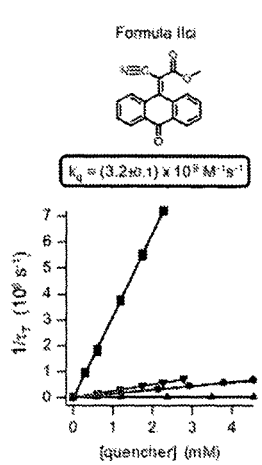
FIGS. 6b, 6c, and 6d are graphs showing the determination of $k_q$, the bimolecular rate constant for quenching of protoporphyrin IX triplet states by the compounds of Formulae IIbi, IIci, a mixture of IIdi and IIei, and IIfi. The graphs depict triplet state lifetime measured at 440 nm by laser flash photolysis vs. quencher (stabilizer) concentration.
Figure 6C:
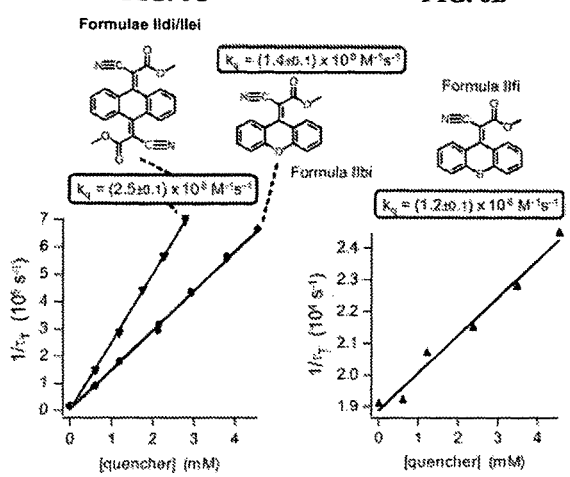
Figure 6D:
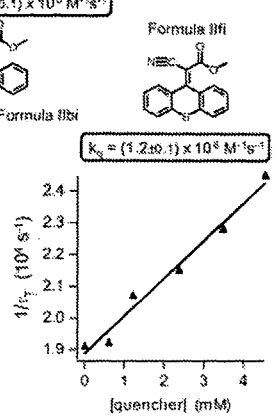

The triplet absorption kinetics at 440 nm can be utilized to obtain triplet quenching rate constants by the stabilizers. Triplet decay traces at 440 nm were recorded in the presence of different amounts of alkoxy crylene, Formula IIai, IIbi, IIci, a mixture of IIdi and IIei, and IIfi. The decay traces were fitted to a first-order kinetics. The plot of these pseudo-first-order rate constants (inverse decay lifetime) vs. the concentration of the two compounds gives directly the bimolecular triplet quenching rate constant from the slope (FIG. 6).

The triplet quenching rate constant for Formula IIai is three orders of magnitude smaller than singlet excited state quenching by the compound of Formula IIai. However, since the triplet lifetime (52 μs) is more than three orders of magnitude larger than the singlet excited state lifetime (13 ns), the smaller rate constant for triplet quenching is compensated by the longer triplet lifetime. This makes protoporphyrin IX triplet state quenching by the compound of Formula IIai more efficient than singlet excited state quenching. Similar to the fluorescence quenching experiments, no triplet quenching was observed by the alkoxy crylene compound. Similarly, the triplet excited state quenching of PPIX varies over three orders of magnitude for Formula IIbi, IIci, a mixture of IIdi and IIei, and IIfi. Interestingly, Formula IIci was the most efficient quencher—the PPIX triplet state quenching is almost as fast as the singlet state quenching.

Because Formula IIci contains a ketone functionality, intersystem crossing into the triplet state could be promoted after photoexcitation due to spin-orbit coupling. Stabilizer triplet states could generate singlet oxygen. Low-temperature luminescence experiments in a ethanol matrix at 77 K were performed in search for phosphorescence of potential triplet states. Only a very weak luminescence was observed with maximum at 492 nm and a quantum yield of less than 1%. Because the excitation spectrum of this luminescence did not match the absorption spectrum, it can be concluded that this luminescence is probably caused by an impurity and no long-lived triplet states of Formula IIci are formed.

The biomolecular quenching rate constants for singlet excited state ($k_q^S$) and triplet excited state ($k_q^T$) quenching of PPIX by stabilizers in acetonitrile solutions at room temperature is shown in Table 1, as well and the Stern-Volmer rate constants (discussed in more detail below).

TABLE 1

| Formula | Singlet Quenching $k_q^S$ ($10^9$ $M^{-1}S^{-1}$) | Triplet Quenching $k_q^T$ ($10^9$ $M^{-1}S^{-1}$) | Stern-Volmer Constant ($M^{-1}$) |
|---|---|---|---|
| IIai | 5.3 ± 0.2 | 0.0061 ± 0.0004 | 30 |
| IIbi | 3.7 ± 0.4 | 0.14 ± 0.01 | 27 |
| IIci | 5.2 ± 0.2 | 3.2 ± 0. | 240 |
| IIdi, IIei mixture | 4.5 ± 0.2 | 0.25 ± 0.2 | 31 |
| IIfi | 0.65 ± 0.05 | 0.0012 ± 0.0001 | 1.2 |
| Alkoxy Crylene | no observable quenching | no observable quenching | 0.2 |

The quenching mechanism of protoporphyrin IX singlet excited states and triplet states by the compound of Formula (II) is not clear. A simple energy transfer mechanism would depend on the singlet and triplet energies of the compound of Formula (II) and protoporphyrin IX. To obtain information on excited state energies of the stabilizer, luminescence experiments were performed. The compound of Formula IIai in ethanol solution did not give detectable fluorescence at room temperature. However, weak luminescence was observed of the compound of Formula IIai in a frozen ethanol matrix at 77 K. The luminescence with maximum at 575 nm (FIG. 7c) originates from the compound of Formula IIai, because the luminescence excitation spectrum (FIG. 7b) matches well the absorption spectrum of the compound of Formula IIai (FIG. 5a). The luminescence lifetime could not be determined, because of the weak signal intensity. However, attempts to record time resolved luminescence spectra suggests that the lifetime is shorter than the microsecond time scale. This suggests that the luminescence at 575 nm is not a typical phosphorescence and probably is the fluorescence. If the luminescence at 575 nm is the fluorescence, then the Stoke's shift is unusually large. Independent of the assignment of the luminescence to the fluorescence or phosphorescence, this excited state energy is higher than singlet and triplet energies of protoporphyrin IX and rules out a simple energy transfer quenching mechanism. Another possible quenching mechanism is electron transfer quenching which would depend on the redox potentials of the protoporphyrin and the two quencher compounds.

Figure 9A:
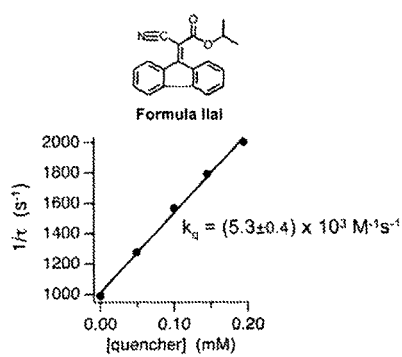
FIG. 9 shows determination of singlet oxygen quenching rate constants $k_q$ by the stabilizers. The graph depicts inverse phosphorescence lifetime vs. quencher (stabilizer) concentration.
Figure 9B:
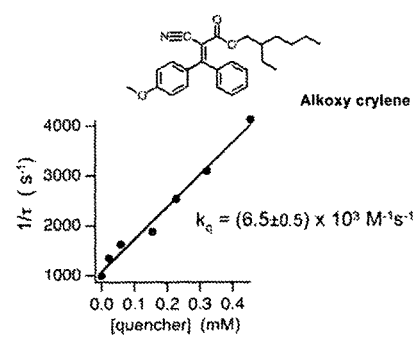

Singlet oxygen quenching by the compound of Formula (II) is another possible photoprotection mechanism. A convenient way to generate singlet oxygen is by photoexcitation of tetraphenylporphyrin (TPP) in the presence of dissolved oxygen. FIG. 8 shows a typical singlet oxygen phosphorescence spectrum (FIG. 8a) and its decay trace (FIG. 8b). The solvent $CCl_4$ was selected, because it is known that the singlet oxygen has a long lifetime in this solvent (ms time scale), which makes the measurement of quenching kinetics easier. Singlet oxygen phosphorescence decay traces, such as shown in FIG. 8b, were recorded in the presence of different quencher concentrations. After fitting the decay traces to a first-order kinetic model, the bimolecular quenching constants were determined from the plots shown in FIG. 9. The singlet oxygen quenching rate constants of both compounds are relatively low. The slightly higher rate constant for the alkoxy crylene compound is consistent with the additional substituents compared to the compound of Formula IIai.

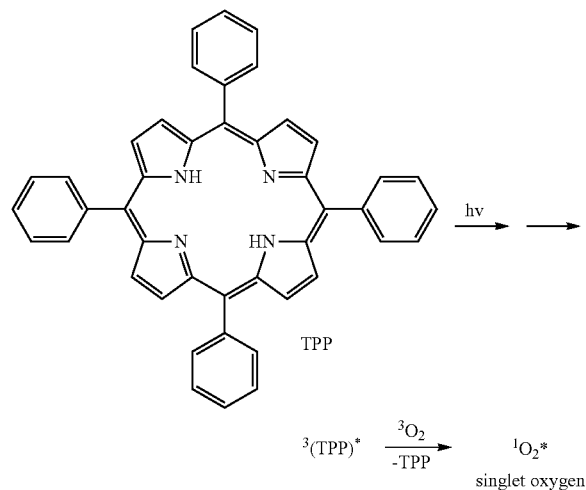

TPP $^3(TPP)^* \xrightarrow[-TPP]{^3O_2} {^1O_2}^*$ singlet oxygen

Figure 10:
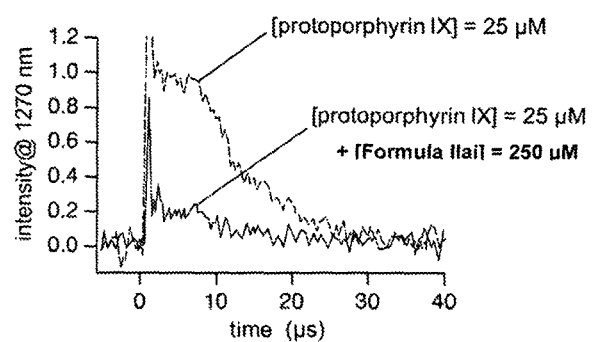
FIG. 10 is a graph showing singlet oxygen phosphorescence decay traces generated by pulsed laser excitation (355 nm) of protoporphyrin IX in air saturated DMSO-$d_6$ solutions in the absence and presence of the compound of Formula IIai.
Figure 11:
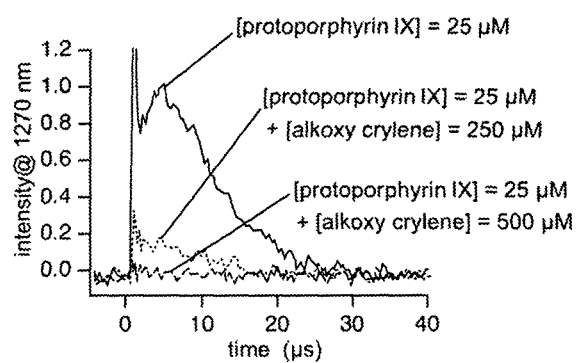
FIG. 11 is a graph showing singlet oxygen phosphorescence decay traces generated by pulsed laser excitation (355 nm) of protoporphyrin IX in air saturated DMSO-$d_6$ solutions in the absence and presence of the alkoxy crylene compound at different concentrations.

Finally, an example of the originally planned experiment was performed, where singlet oxygen was generated by pulsed laser excitation in the UV (355 nm) by protoporphyrin IX. Protoporphyrin IX was selected on the basis of its high extinction coefficient (FIG. 2). The solvent DMSO-$d_6$ was selected because of good solubility of the sensitizer and stabilizers. The deuterated form of DMSO was used because of the longer singlet oxygen lifetime in deuterated solvents compared to solvents containing hydrogen. FIGS. 10 and 11 show kinetic traces of singlet oxygen phosphorescence generated from photoexcitation of protoporphyrin IX. In the presence of small amounts (250 μM) of the compound of Formula IIai (FIG. 10) or the alkoxy crylene compound (FIG. 11) there was significantly reduced singlet oxygen phosphorescence. However, the reduced amount of generated singlet oxygen in the presence of the alkoxy cylene compound is probably caused by competitive excitation light absorption, where most of the light is absorbed by the compound of Formula IIai or the two compounds and not by protoporphyrin IX. Excited state quenching of the protoporphyrin IX by the two compounds is unlikely to occur at these low stabilizer concentrations (μM). As shown in FIGS. 4 and 6, much higher stabilizer concentrations are needed (mM) for excited sensitizer state quenching of porphyrin compounds (sensitizers).

To investigate to what extent the stabilizers can generate singlet oxygen upon direct UV photolysis, singlet oxygen phosphorescence measurements were performed under photolysis at 355 nm. For these experiments $CCl_4$ was selected as solvent, because of the long lifetime of singlet oxygen in this solvent, which makes these experiments easier to perform. Weak singlet oxygen signals were observed upon photolysis at 355 nm (FIG. 12). Using benzophenone as reference (quantum yield of singlet oxygen generation: 0.35) the low quantum yields of singlet oxygen generation were estimated: compound of Formula IIai: 0.015 and alkoxy crylene: ~0.001.

Figure 13:
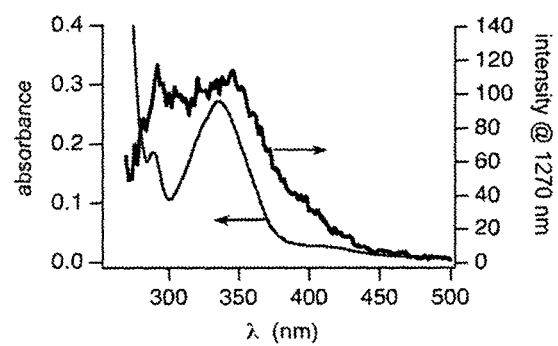
FIG. 13 is a graph showing an absorption spectrum and a singlet oxygen phosphorescence excitation spectrum (monitored at 1270 nm) of alkoxy crylene in air saturated $CCl_4$ solutions.

To ensure that the observed weak singlet oxygen signals truly originated from the two compounds and not from possible impurities in the sample or solvent, singlet oxygen phosphorescence excitation spectra were recorded. Because the excitation spectrum resembles the absorption spectrum (FIG. 13), it can be concluded that the major amount of observed weak singlet oxygen phosphorescence was generated from the compound of Formula (II). However, no match of the excitation spectrum with the absorption spectrum was observed for the alkoxy crylene compound, which suggests that the observed very weak singlet oxygen originated mostly from impurities.

In conclusion, the mechanism of photoprotection by the compound of Formula (II) and the non-fused alkoxy crylene compound is probably dominated by their strong light absorption and fast deactivation to the ground state. However, excited state quenching, as shown for protoporphyn IX with the compound of Formula IIai, should provide additional photoprotection.

Figure 14A:
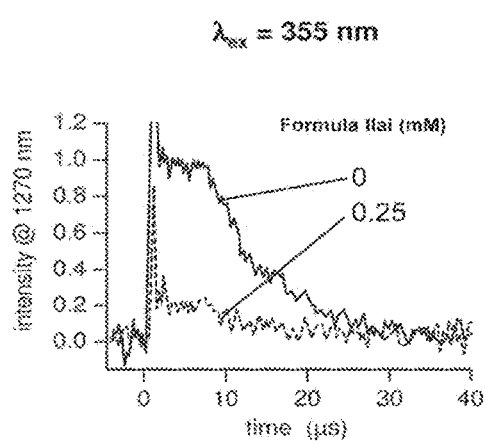
FIG. 14 shows singlet oxygen phosphorescence decay traces monitored at 1270 nm generated by pulsed laser excitation at 355 nm (FIGS. 14a and 14c) or 532 nm (FIGS. 14b and 14d) of protoporphyrin IX (25 µM) in air saturated DMSO-$d_6$ solutions in the absence and presence of the compound of Formula IIai and the alkoxy crylene compound.
Figure 14B:
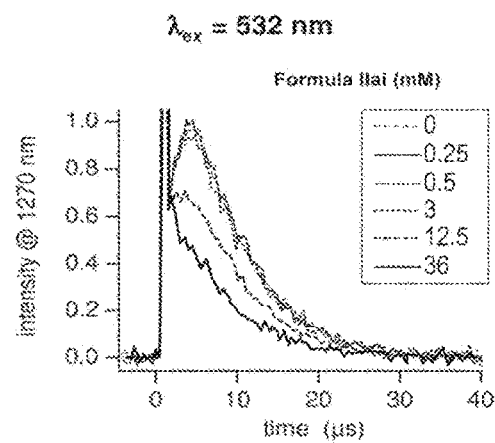
Figure 14C:
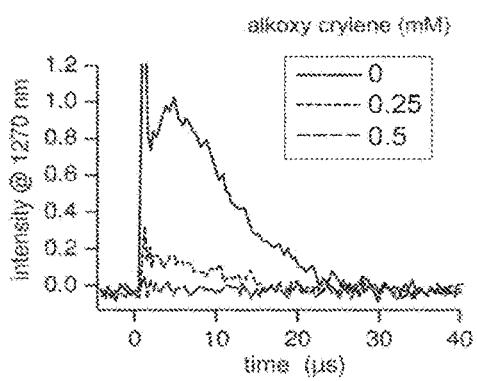
Figure 14D:
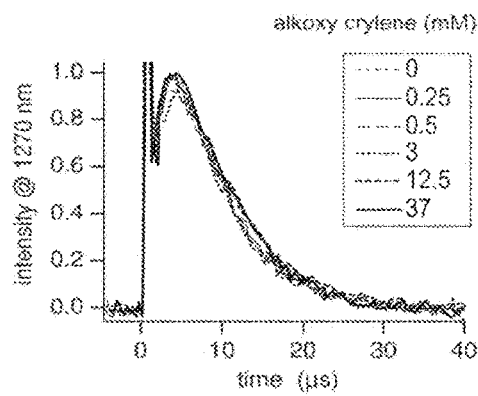

In the previous experiments, singlet oxygen was generated by pulsed laser excitation in the UV spectral region (355 nm) of protoporphyrory IX. The singlet oxygen generation was mostly suppressed by addition of small amounts of the compound of Formula IIai or the alkoxy crylene compound (FIGS. 14a and 14c). This was explained by a simple optical screening mechanism, where the compound of Formula IIai and alkoxy crylene absorb the UV light.

Figure 1D:
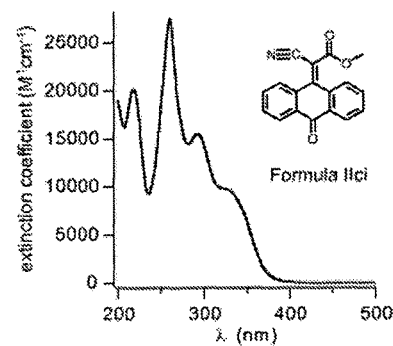

In the new experiments, laser excitation was performed with visible light at 532 nm, where the compound of Formula IIai and the alkoxy crylene compound are transparent. No suppression of singlet oxygen generation was observed by the presence of the alkoxy crylene compound even at high concentrations (37 mM) (FIG. 1d). The absence of singlet oxygen suppression with 532 nm excitation supports the optical screening mechanism with 355 nm excitation. In the presence of the compound of Formula IIai at concentrations above 3 mM the amount of generated singlet oxygen was reduced (FIG. 14b). This reduction is probably caused by protoporphyrin IX excited state quenching by the compound of Formula IIai. In the previous experiments it was shown that protoporphyrin IX singlet and triplet excited states are quenched by the compound of Formula IIai, but not by the alkoxy crylene compound.

The above-described experiments with protoporphyrin IX were performed in DMSO-$d_6$, a solvent with a relatively short singlet oxygen lifetime, because the polar protoporphyrin IX is not soluble enough is solvents with long singlet oxygen lifetimes, such as $CDCl_3$ and $CCl_4$. Solvents with long singlet oxygen lifetimes make singlet oxygen phosphorescence measurements significantly easier to perform.

Figure 15:
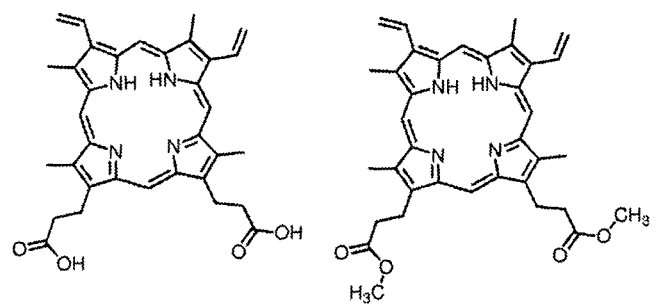
FIG. 15 shows the structures of protoporphyrin IX and protoporphyrin IX dimethyl ester.

Singlet oxygen phosphorescence experiments were performed to investigate if the large differences in triplet quenching rate constants have an impact on the observed singlet oxygen yields. The dimethyl ester derivative of PPIX (MePPIX, FIG. 15) was selected as sensitizer, because of better solubility in a solvent with long singlet oxygen lifetime ($CDCl_3$). The excited state properties of protoporphyrin IX should not be effected by the methyl ester functionality. Air saturated $CDCl_3$ of MePPIX were excited with a pulsed Nd-YAG laser with visible light at 532 nm, where the stabilizers are mostly transparent. FIG. 16 shows the generated kinetic traces of singlet oxygen phosphorescence in the absence and presence of stabilizers. Comparison of these kinetic traces shows major differences for the different stabilizers. The non-bridged stabilizer, alkoxy crylene did not suppress singlet oxygen generation. The lack of singlet oxygen suppression is consistent with the lack of observable quenching of singlet or triplet excited states of PPIX by alkoxy crylene. The bridged stabilizers suppressed singlet oxygen generation to different degrees with IIci showing the largest suppression.

Figure 16A:
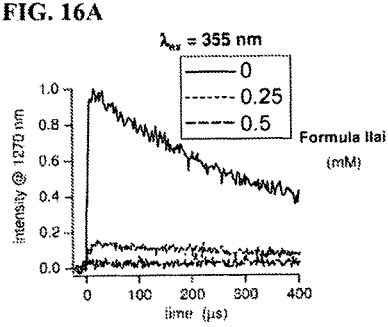
FIG. 16 shows singlet oxygen phosphorescence decay traces monitored at 1270 nm generated by pulsed laser excitation at 355 nm (FIGS. 16a and 16c) or 532 nm (FIGS. 16b and 16d) of protoporphyrin IX dimethyl ester (25 µM), and monitored at 1270 nm generated by pulsed laser excitation at 532 nm of protoporphyrin IX dimethyl ester (17 µM) (FIGS. 16e, 16f, 16g, 16h, 16i, and 16j) in air saturated $CDCl_3$ solutions in the absence and presence of the compound of Formulae IIai, IIbi, IIci, a mixture of IIdi and IIei, IIfi and the alkoxy crylene compound, commercially available as SolaStay® S1 (The HallStar Company).
Figure 16B:
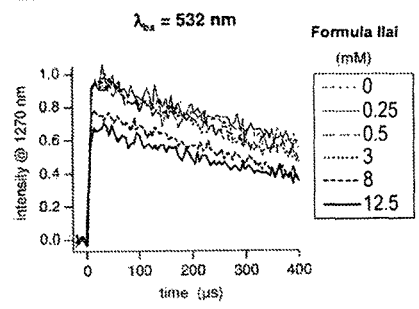
Figure 16C:
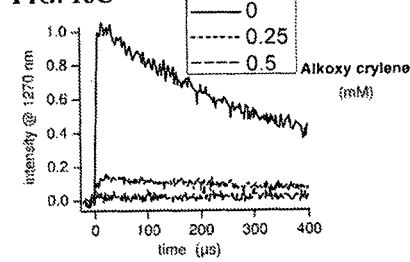
Figure 16D:
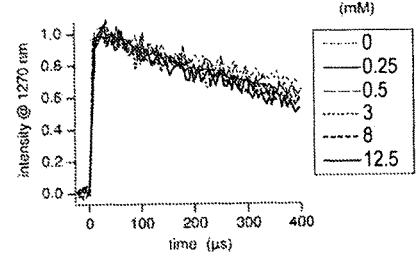
Figure 16E:
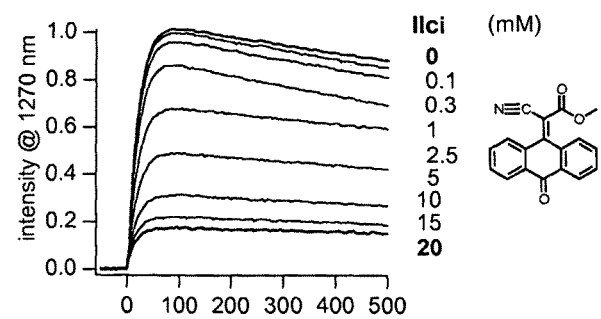
Figure 16F:
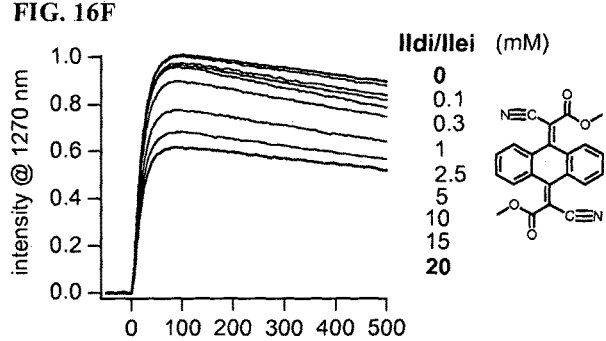
Figure 16G:
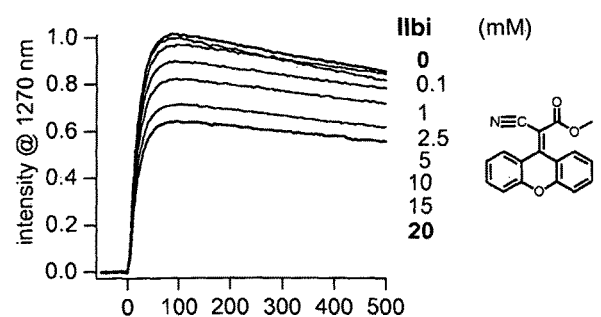
Figure 16H:
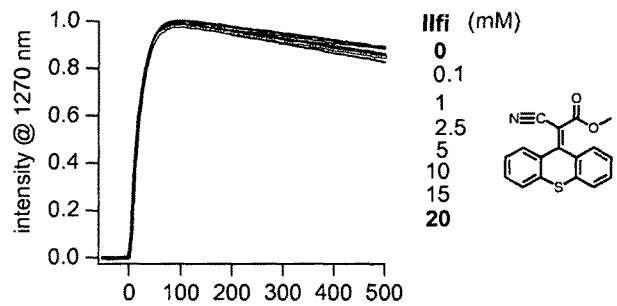
Figure 16I:
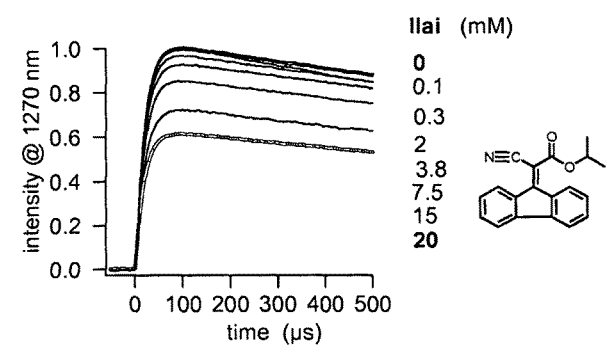
Figure 16J:
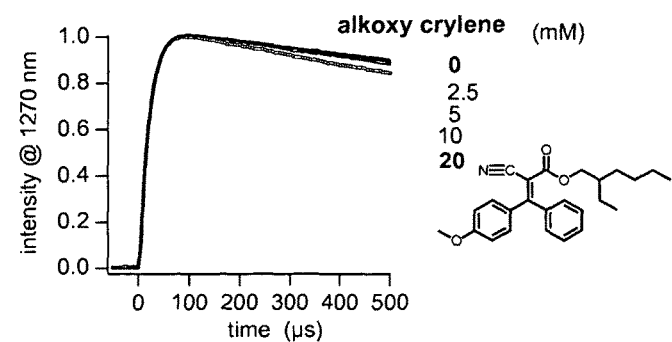

The singlet oxygen phosphorescence experiments shown in FIG. 3 using the dimethyl ester derivative of protoporphyrin IX in $CDCl_3$ are qualitatively similar to those shown in FIG. 14 using protoporphyrin IX in DMSO-$d_6$. Although singlet oxygen phosphorescence detection was easier in $CDCl_3$, decomposition of protoporphyrin IX dimethyl ester by singlet oxygen caused a larger error in phosphorescence intensity, which was especially visible in FIG. 16d compared to FIG. 14d. The longer singlet oxygen lifetime in $CDCl_3$ makes the chromophore more sensitive to oxidative damage.

Figure 17A:
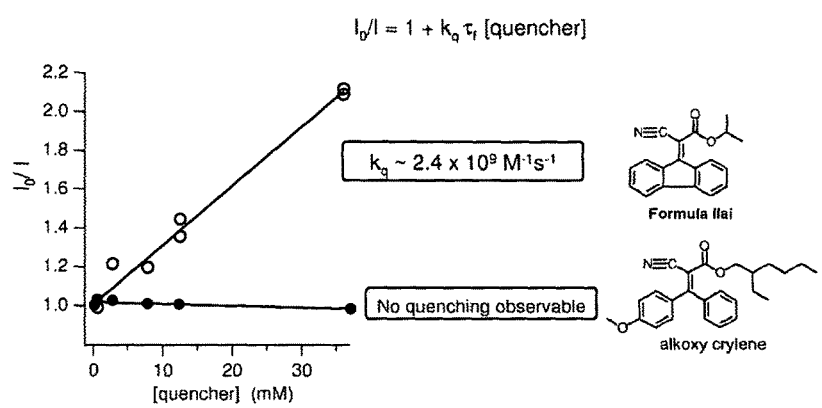
FIG. 17 shows a Stern-Volmer plot of singlet oxygen phosphorescence data from decay traces generated by pulsed laser excitation at 355 nm (FIGS. 14a and 14c) or 532 nm (FIGS. 14b and 14d)) of protoporphyrin IX (25 µM) in air saturated DMSO-$d_6$ solutions in the absence and presence of the compound of Formula IIai and the alkoxy crylene compound (FIG. 17a), and at 532 nm (FIGS. 16e, 16f, 16g, 16h, 16i, and 16j) of protoporphyrin IX dimethyl ester (17 µM) in air saturated $CDCl_3$ solutions in the absence and presence of the compound of Formulae IIai, IIbi, IIci, a mixture of IIdi and IIei, and IIf, and the alkoxy crylene compound (FIGS. 17b and 17c)i.
Figure 17B:
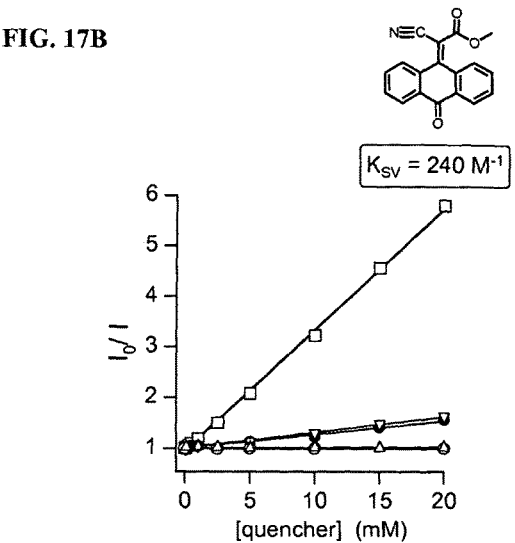
Figure 17C:
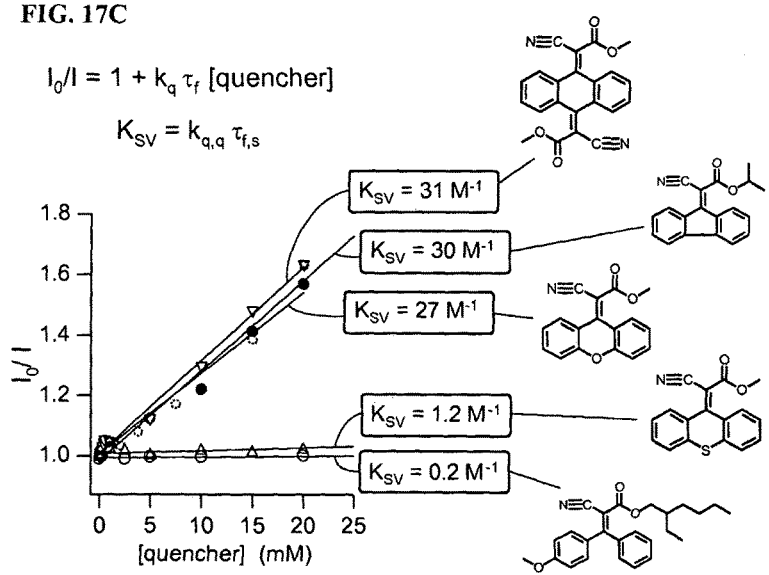

To demonstrate that the suppression of singlet oxygen generation from photoexcitation at 532 nm is caused by singlet excited state quenching of protoporphyrin IX by the compound of Formula (II), Stern-Volmer analysis of the data in FIG. 14b and FIG. 16 was performed. The singlet oxygen phosphorescence intensity in the absence of stabilizer (i.e, the compound of Formulae IIai, IIbi, IIci, a mixture of IIdi and IIei, or IIfi) ($I_0$) divided by the singlet oxygen phosphorescence intensity in the presence of stabilizer (i.e., the compound of Formulae IIai, IIbi, IIci, the mixture of IIdi and IIei, or IIfi) (I) was plotted against the Formula (II) concentration (FIG. 17). From the slope of these plots (Stern-Volmer constant) and the lifetime of the quenched excited state, the bimolecular quenching constant can be extracted. If the excited state, which is quenched by the compound of Formula IIai (which causes a reduction in singlet oxygen production) is the singlet excited state of protoporphyrin IX then, using the previously measured fluorescence lifetime in acetonitrile ($\tau f=12.7$ ns) a quenching rate constant of $2.4 \times 10^9$ $M^{-1}s^{-1}$ is estimated. This rate constant is in the same order of the previously measured rate constant using fluorescence quenching ($5.3 \times 10^9$ $M^{-1}s^{-1}$) which indicates that singlet excited state quenching of protoporphyrin by the compound of Formula IIai is predominantly causing the suppression of singlet oxygen generation. The rate constant derived from singlet oxygen phosphorescence quenching (FIG. 17) is only half of the more directly derived rate constant from fluorescence quenching, which could be caused by the difference in solvents or by some contribution of protoporphyrin triplet quenching by the compound of Formula IIai. If the suppression of singlet oxygen generation would be entirely caused by triplet protoporphyrin IX quenching by the compound of Formula IIai, the rate constant from the Stern-Volmer plot (FIG. 4) would be $\sim 3 \times 10^7$ $M^{-1}s^{-1}$ considering a protoporphyrin IX triplet lifetime of $\sim 1$ µs in air saturated DMSO. This rate constant is 5 times higher than the directly measured rate constant by laser flash photolysis ($6.1 \times 10^6$ $M^{-1}s^{-1}$) This suggests that protoporphyrin IX triplet quenching by the compound of Formula (II) makes only a minor contribution to the suppression of singlet oxygen generation under these conditions. It must be noted that protoporphyrin IX triplet lifetime of $\sim 1$ µs in air saturated DMSO was only estimated based on the directly measured triplet lifetime in air saturated acetonitrile and considering the different oxygen concentration in DMSO compared to acetonitrile. If necessary, the protoporphyrin IX triplet lifetime in air saturated DMSO can easily be measured by laser flash photolysis.

The Stern-Volmer constants are in direct correlation with the singlet oxygen suppression efficiency. Table 1 (above) summarizes the Stern-Volmer constants and PPIX singlet and triplet state quenching rate constants. Three different ranges of Stern-Volmer constants were observed. For alkoxy crylene and compound IIfi, only negligible singlet oxygen suppression and low Stern-Volmer constants were observed, which is probably caused by the low PPIX singlet and triplet quenching rate constants of these stabilizers. For compounds IIai, IIbi, and the mixture of IIdi and IIei, Stern-Volmer constants of about 30 $M^{-1}$ were observed. For these three stabilizers, high PPIX singlet quenching rate constants (about $5 \times 10^9$ $M^{-1}$ $s^{-1}$) but low triplet quenching rate constants ($<10^9$ $M^{-1}$ $s^{-1}$) were observed. Here, the singlet oxygen suppression is probably dominated by PPIX singlet excited state quenching by these stabilizers. The highest Stern-Volmer constant was observed for compound IIci (240 $M^{-1}$). Because of the very high PPIX triplet quenching rate constant by compound IIci ($3.2 \times 10^9$ $M^{-1}s^{-1}$), the singlet oxygen suppression is probably dominated by triplet quenching. To prove this switch in mechanism and kinetic control of singlet oxygen suppression, additional kinetic parameters would need to be determined, which are easily accessible by laser flash photolysis and time correlated single photon counting. These kinetic parameters include the MePPIX triplet and singlet lifetimes in air saturated and oxygen free $CDCl_3$ and the bimolecular quenching constant by oxygen.

The complex quenching reaction mechanism of protoporphyrin IX excited states is summarized in Scheme 1.

Scheme 1: Quenching mechanism of protoporphyrin IX excited states

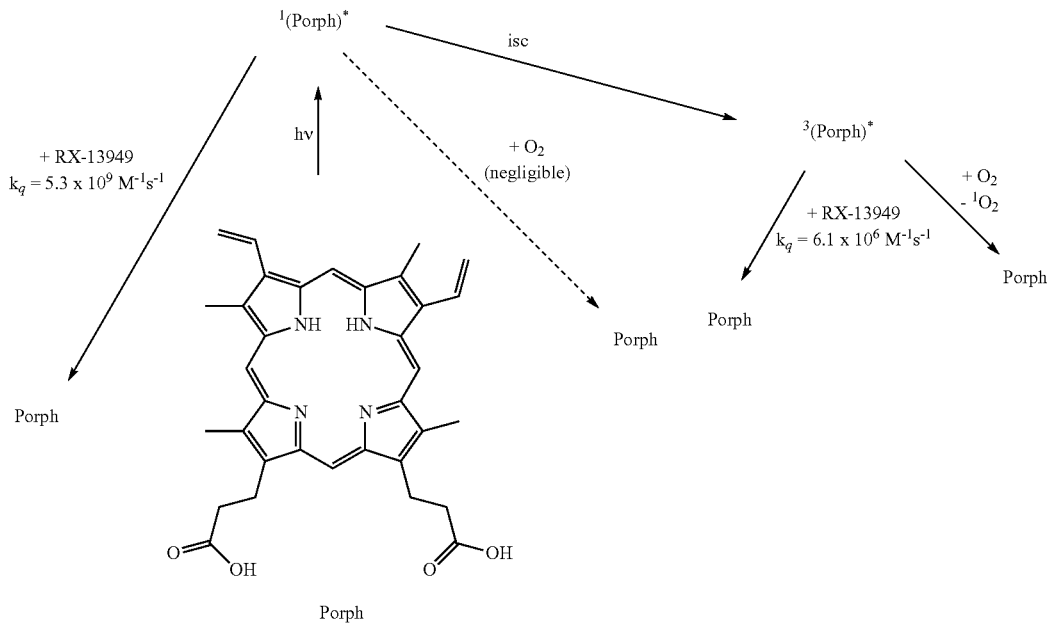

Figure 18A:
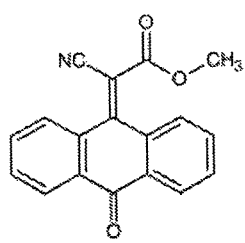
FIG. 18 shows the structures of additional specific compounds in accordance with Formula (II).
Figure 18B:
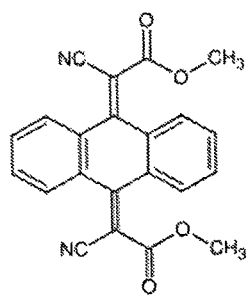
Figure 18C:
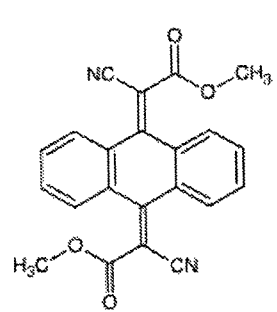

Additional conjugated fused tricyclic compounds having electron withdrawing groups having Formulas IIai, IIbi, IIci, IIdi, and IIei were tested against the alkoxy crylene compound as shown in FIGS. 18 and 19.

The redox potential of protoporphyrin IX, Formula IIai, IIbi, IIci, a mixture of IIdi and IIei, IIfi, and alkoxy crylene were determined with respect to a Ag/AgCl reference electrode. For these experiments, dimethylsulfoxide (DMSO) and tetrabutylammonium perchlorate (TBAP) were obtained from Sigma Aldrich and used as received. Acetone was obtained from Fisher Scienfitic. Solutions of 0.01 M (10 mM) of protoporphyrin IX, Formula IIai, IIbi, IIci, a mixture of IIdi and IIei, IIfi, and alkoxy crylene were prepared by dissolving measured amounts in a supporting electrolyte of 0.1 M TBAP in DMSO; the total volume of each sample solution was 15 mL. Platinum wires (BASi MW-1032) of diameter 0.5 mm were employed for both the working electrode (WE) and counter electrode (CE). A dry-solvent tolerant Ag/AgCl reference electrode (RE) was obtained from eDAQ (Model ET072). The WE and CE were cleaned prior to each by first rinsing in acetone, then DI, followed by soaking in ~50% aqueous $H_2SO_4$ for 10-20 minutes and then a final DI rinse. The RE electrode was cleaned prior to each use by an acetone rinse followed by DI rinse. Each sample solution was prepared in a fresh glass vial which had been rinsed with DI then acetone and allowed to dry. Immediately after preparing each solution, it was purged with pure $N_2$ gas for 15-20 minutes with the electrodes in place. Voltammetry data was collected shortly afterwards with an EG&G PAR 263 A Potentiostant/Galvanostat operated using a Labview-based control program. Scans were performed at various potential ranges between +2.0V and −2.0V (vs Ag/AgCl); all scan rates were constant at 200 mV/s.

Figure 19A:
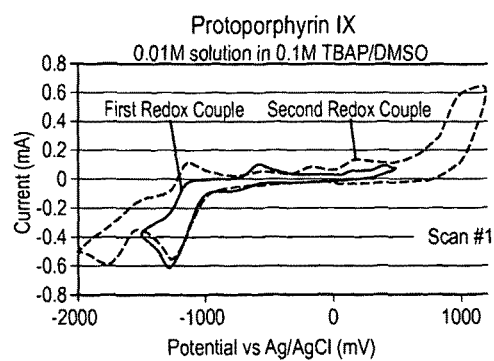
FIG. 19 shows the redox potential of protoporphyrin IX (FIG. 19a), Formula IIai (FIG. 19b), IIbi (FIG. 19c), IIfi (FIG. 19d), IIci (FIG. 19e), a mixture of IIdi and IIei (FIG. 19f), and alkoxy crylene (FIG. 19g).

The voltammograms for protoporphyrin IX appear to show the presence of two distinct redox couples (FIG. 19a). The first redox couple has a large reduction peak at −1255 mV and a smaller oxidation peak at −610 mV (two much smaller oxidation peaks are present at −202 mV and +164 mV which may also be associated with this couple); the redox potential for this couple is thus estimated as −932 mV. The second redox couple has a reduction peak near −1741 mV and an oxidation peak near −1152 mV; this yields a redox potential of approximately −1446 mV.

Figure 19B:
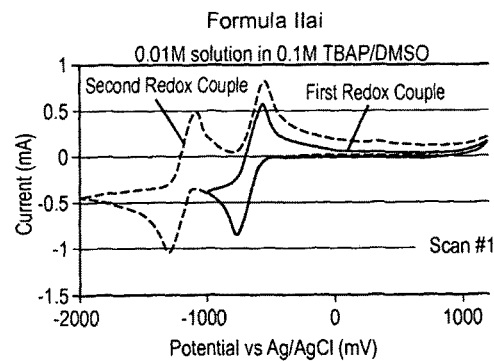

The voltammograms for Formula IIai also show the presence of two distinct redox couples (FIG. 19b). The first redox couple has a reduction peak at −757 mV and an oxidation peak at −560 mV; the redox potential for this couple is thus estimated as −658 mV. The second redox couple has a reduction peak at −1297 mV and an oxidation peak at −1102 mV; the redox potential is approximately −1199 mV.

Figure 19C:
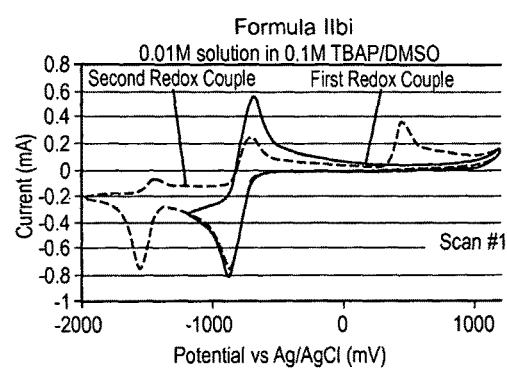

The voltammograms for Formula IIbi show the presence of two distinct redox couples (FIG. 19c). The first redox couple has a reduction peak at −864 mV and an oxidation peak at −706 mV; the redox potential for this couple is thus estimated as −785 mV. The second redox couple has a reduction peak at −1537 mV and oxidation peaks at −1466 mV (small) and +430 mV (large); the redox potential is estimated as −1501 mV.

Figure 19D:
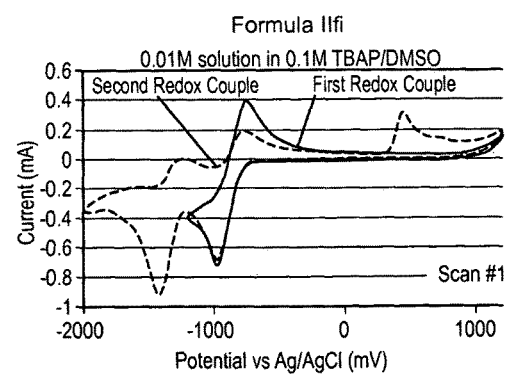

The voltammograms for Formula IIfi show the presence of two distinct redox couples (FIG. 19d). The first redox couple has a reduction peak at −969 mV and an oxidation peak at −782 mV; the redox potential for this couple is thus estimated as −875 mV. The second redox couple has a reduction peak at −1409 mV and oxidation peaks at −1286 mV (small) and +434 mV (large); the redox potential is estimated as −1347 mV.

Figure 19E:
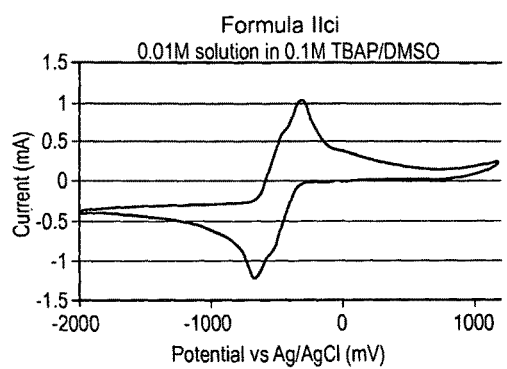

The voltammogram for Formula IIci shows the presence of only one distinct redox couple (FIG. 19e). This couple has a reduction peak at −656 mV and an oxidation peak at −300 mV; the redox potential is thus estimated as −493 mV.

Figure 19F:
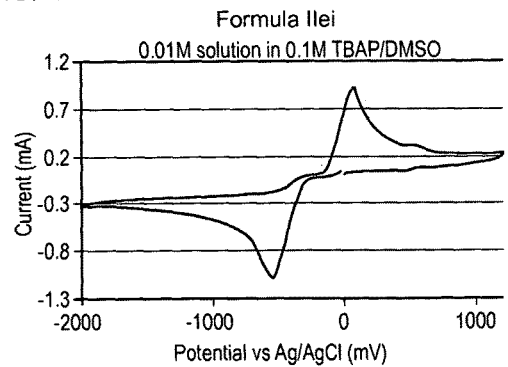

The voltammograms for the mixture of Formula IIdi and Formula IIei also shows the presence of only one distinct redox couple (FIG. 19f). This couple has a reduction peak at −545 mV and an oxidation peak at +54 mV; the redox potential for this couple is thus estimated as −245 mV.

Figure 19G:
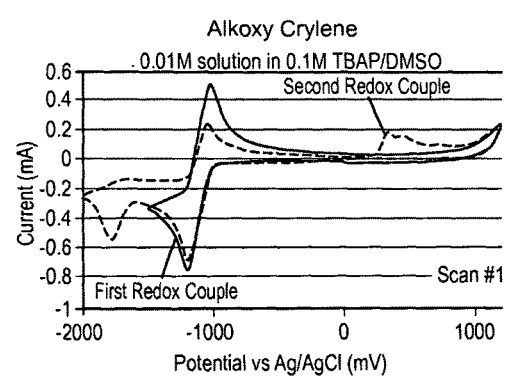

The voltammograms for alkoxy crylene show the presence of two distinct redox couples (FIG. 19g). The first redox couple has a reduction peak at −1183 mV and an oxidation peak at −1038 mV; the redox potential for this couple is thus estimated as −1110 mV. The second redox couple has a reduction peak at −1751 mV and an oxidation peak at +318 mV; the redox potential is estimated as −694 mV.

The invention claimed is:

1. A method of quenching excited state energy from a pigment that has been excited by absorption of light having a wavelength in the wavelength range of 290-800 nm, comprising reacting a pigment with a conjugated fused tricyclic compound having electron withdrawing groups of Formula (II) or a salt thereof:

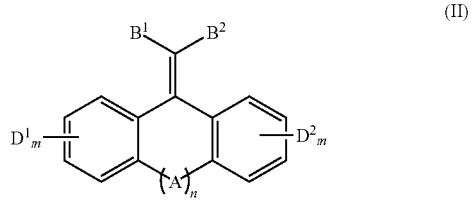

(II)

wherein:

A is selected from the group consisting of O, S, C=O, C=S,

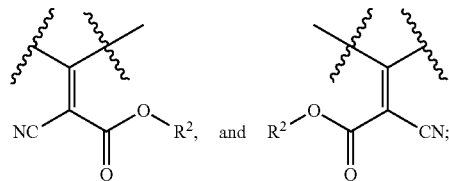

$B^1$, $B^2$, $D^1$, and $D^2$ are each independently selected from the group consisting of F, Cl, Br, I, $CF_3$, $CCl_3$, $NR^3_3{}^+$, $NO_2$, CN, C(=O)$R^4$, C(=O)$OR^1$, $SO_2R^5$, aryl, and —C=CH$R^6$;

each m independently is 0, 1, 2, 3, or 4;

each $R^1$ is independently selected from the group consisting of H, alkyl, alkenyl, alkynyl, cycloalkyl, cycloalkenyl, and aryl;

$R^2$ is selected from the group consisting of H, alkenyl, alkynyl, and aryl;

each $R^3$ is independently selected from the group consisting of H and $C_1$-$C_6$ alkyl;

each $R^4$ is independently selected from the group consisting of H, alkyl, alkenyl, alkynyl, cycloalkyl, cycloalkenyl, and aryl;

each $R^5$ is independently selected from the group consisting of H, OH, $NH_2$, and Cl; and, each $R^6$ is independently selected from the group consisting of alkyl, alkenyl, alkynyl, cycloalkyl, cycloalkenyl, and aryl, wherein if $B_1$=CN, and $B_2$=C(O)$OR^1$, then $R^1 \neq$alkyl or cycloalkyl.

2. A method of suppressing the generation of a reactive oxygen species selected from the group consisting of singlet oxygen, superoxide anion, peroxide, hydroxyl radical, hydroxyl ion, and mixtures thereof, by an excited pigment when mammalian endogenous pigment is exposed to light, thereby exciting the pigment to an excited state, by quenching the excited state of the pigment compound with a conjugated fused tricyclic compound having electron withdrawing groups of Formula (II) or a salt thereof:

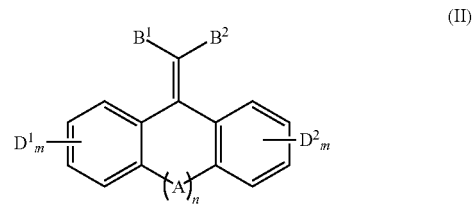

(II)

wherein:

A is selected from the group consisting of O, S, C=O, C=S,

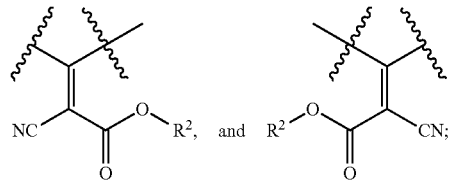

$B^1$, $B^2$, $D^1$, and $D^2$ are each independently selected from the group consisting of F, Cl, Br, I, $CF_3$, $CCl_3$, $NR^3_3{}^+$, $NO_2$, CN, C(=O)$R^4$, C(=O)$OR^1$, $SO_2R^5$, aryl, and —C=CH$R^6$;

each m independently is 0, 1, 2, 3, or 4;

n is 0 or 1;

each $R^1$ is independently selected from the group consisting of H, alkyl, alkenyl, alkynyl, cycloalkyl, cycloalkenyl, and aryl;

$R^2$ is selected from the group consisting of H, alkyl, cycloalkyl, alkenyl, alkynyl, and aryl;

each $R^3$ is independently selected from the group consisting of H and $C_1$-$C_6$ alkyl;

each $R^4$ is independently selected from the group consisting of H, alkyl, alkenyl, alkynyl, cycloalkyl, cycloalkenyl, and aryl;

each $R^5$ is independently selected from the group consisting of H, O$^-$, OH, $NH_2$, and Cl; and, each $R^6$ is independently selected from the group consisting of alkyl, alkenyl, alkynyl, cycloalkyl, cycloalkenyl, and aryl, wherein if $B_1$=CN, and $B_2$=C(=O)$OR^1$, then $R^1 \neq$alkyl or cycloalkyl wherein if n=0, $B_1$=CN, then $B_2 \neq$CN, and wherein if n=0, $B_1$=C(=O)$OR^1$, and $B_2$=C(=O)$OR^1$, then $R^1 \neq$alkyl or cycloalkyl.

3. A method of protecting skin from oxidative stress caused by the photogeneration of a reactive oxygen species from the group consisting of singlet oxygen, superoxide anion, peroxide, hydroxyl radical, hydroxyl ion, and mixtures thereof, comprising coating the skin with a pigment excited state quencher capable of accepting or donating an electron from or to a pigment compound in the excited state and returning the excited pigment compound to its ground state, said pigment quencher comprising a conjugated fused tricyclic compound having electron withdrawing groups of Formula (II) or a salt thereof:

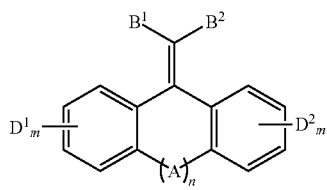

(II)

wherein:

A is selected from the group consisting of O, S, C=O, C=S,

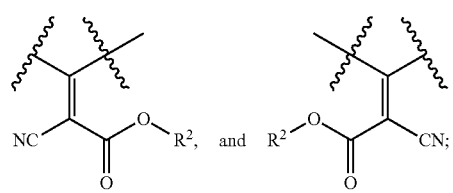

$B^1$, $B^2$, $D^1$, and $D^2$ are each independently selected from the group consisting of F, Cl, Br, I, $CF_3$, $CCl_3$, $NR^3_3{}^+$, $NO_2$, CN, $C(=O)R^4$, $C(=O)OR^1$, $SO_2R^5$, aryl, and —C=$CHR^6$;

each m independently is 0, 1, 2, 3, or 4;

n is 0 or 1;

each $R^1$ is independently selected from the group consisting of H, alkyl, alkenyl, alkynyl, cycloalkyl, cycloalkenyl, and aryl;

$R^2$ is selected from the group consisting of H, alkyl, cycloalkyl, alkenyl, alkynyl, and aryl;

each $R^3$ is independently selected from the group consisting of H and $C_1$-$C_6$ alkyl;

each $R^4$ is independently selected from the group consisting of H, alkyl, alkenyl, alkynyl, cycloalkyl, cycloalkenyl, and aryl;

each $R^5$ is independently selected from the group consisting of H, $O^-$, OH, $NH_2$, and Cl; and, each $R^6$ is independently selected from the group consisting of alkyl, alkenyl, alkynyl, cycloalkyl, cycloalkenyl, and aryl, wherein if $B_1$=CN, and $B_2$=C(=O)$OR^1$, then $R^1 \neq$ alkyl or cycloalkyl wherein if n=0, CN, then $B_2 \neq$ CN, and wherein if n=0, $B_1$=C(=O)$OR^1$, and $B_2$=C(=O)$OR^1$, then $R^1 \neq$ alkyl or cycloalkyl.

4. A method of protecting healthy cells adjacent to cancerous or pre-cancerous cells undergoing photodynamic therapy comprising applying a composition comprising a pigment excited state quencher compound to said adjacent cells to reduce the generation of reactive oxygen species from said healthy cells while the photodynamic therapy generates free radical oxygen from said cancerous or pre-cancerous cells, with a conjugated fused tricyclic compound having electron withdrawing groups of Formula (II) or a salt thereof:

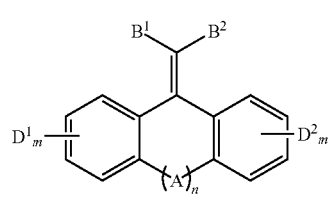

(II)

wherein:

A is selected from the group consisting of O, S, C=O, C=S,

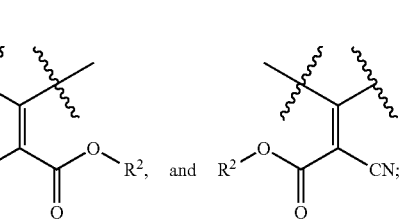

$B^1$, $B^2$, $D^1$, and $D^2$ are each independently selected from the group consisting of F, Cl, Br, I, $CF_3$, $CCl_3$, $NR^3_3{}^+$, $NO_2$, CN, $C(=O)R^4$, $C(=O)OR'$, $SO_2R^5$, aryl, and —C=$CHR^6$;

each m independently is 0, 1, 2, 3, or 4;

n is 0 or 1;

each $R^1$ is independently selected from the group consisting of H, alkyl, alkenyl, alkynyl, cycloalkyl, cycloalkenyl, and aryl;

$R^2$ is selected from the group consisting of H, alkyl, cycloalkyl, alkenyl, alkynyl, and aryl;

each $R^3$ is independently selected from the group consisting of H and $C_1$-$C_6$ alkyl;

each $R^4$ is independently selected from the group consisting of H, alkyl, alkenyl, alkynyl, cycloalkyl, cycloalkenyl, and aryl;

each $R^5$ is independently selected from the group consisting of H, $O^-$, OH, $NH_2$, and Cl; and, each $R^6$ is independently selected from the group consisting of alkyl, alkenyl, alkynyl, cycloalkyl, cycloalkenyl, and aryl, wherein if $B_1$=CN, and $B_2$=C(=O)$OR^1$, then $R^1 \neq$ alkyl or cycloalkyl wherein if n=0, $B_1$=CN, then $B_2 \neq$ CN, and wherein if n=0, $B_1$=C(=O)$OR^1$, and $B_2$=C(=O)$OR^1$, then $R^1 \neq$ alkyl or cycloalkyl.

5. The method of claim 1, wherein the pigment is selected from the group consisting of a melanin, hemoglobin, a bile pigment, a flavin, a pterin, urocanic acid, a porphyrin compound, and combinations thereof.

6. The method of claim 5, wherein the pigment is a melanin selected from the group consisting of eumelanin, pheomelanin, neuromelanin, and combinations thereof.

7. The method of claim 5, wherein the pigment is hemoglobin.

8. The method of claim 5, wherein the pigment is a bile pigment selected from the group consisting of bilirubin, biliverdin, and a combination thereof.

9. The method of claim 5, wherein the pigment is a flavin selected from the group consisting of riboflavin, flavin mononucleotide, a flavoprotein, flavin adenine dinucleotide, and combinations thereof.

10. The method of claim 5, wherein the pigment is a pterin selected from the group consisting of pteridine, biopterin, tetrahydrobiopterin, molybdopterin, cyanopterin, tetrahydromethanopterin, folic acid, and combinations thereof.

11. The method of claim 5, wherein the pigment is urocanic acid.

12. The method of claim 5, wherein the porphyrin compound comprises a porphyrin moiety of Formula (I) or derivatives or tautomers thereof:

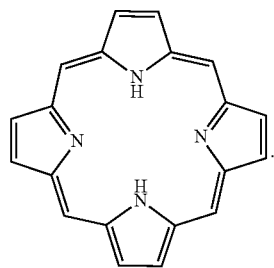

(I)

13. The method of claim 9, wherein the porphyrin compound of Formula (I) comprises:

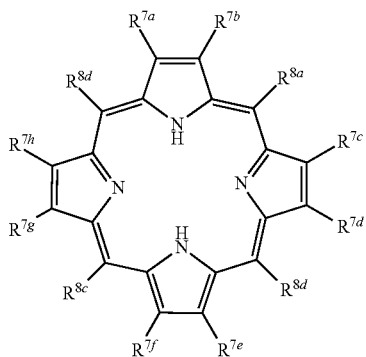

or a multimer thereof,
wherein:
$R^{7a}$, $R^{7b}$, $R^{7c}$, $R^{7d}$, $R^{7e}$, $R^{7f}$, $R^{7g}$, $R^{7h}$ are each independently selected from the group consisting of H, alkyl, alkenyl, alkynyl, hydroxyl, alkoxyl, carboxyl, carboxylic ester, amino, sulfhydryl, aryl, and heteroaryl; and,
$R^{8a}$, $R^{8b}$, $R^{8c}$, $R^{8d}$, and $R^{8e}$ are each independently selected from the group consisting of H, alkyl, alkenyl, alkynyl, hydroxyl, alkoxyl, carboxyl, carboxylic ester, amino, sulfhydryl, aryl, and heteroaryl.

14. The method of claim 13, wherein:
$R^{7a}$, $R^{7b}$, $R^{7c}$, $R^{7d}$, $R^{7e}$, $R^{7f}$, $R^{7g}$, $R^{7h}$ are each independently selected from the group consisting of H, $C_1$-$C_6$ unsubstituted alkyl, $C_1$-$C_6$ hydroxyalkyl, $C_1$-$C_6$ carboxyalkyl, $C_1$-$C_6$ esteralkyl, $C_1$-$C_6$ sulfhydrylalkyl $C_1$-$C_6$ alkenyl, amino, aryl, and heteroaryl; and,
$R^{8a}$, $R^{8b}$, $R^{8c}$, $R^{8d}$, and $R^{8e}$ are each independently selected from the group consisting of H, $C_1$-$C_6$ alkyl, $C_1$-$C_6$ alkenyl, aryl, and heteroaryl.

15. The method of claim 5, wherein the porphyrin compound is selected from the group consisting of 5-azaprotoporphyrin IX, bis-porphyrin, coproporphyrin III, deuteroporphyrin, deuteroporphyrin IX dichloride, diformyl deuteroprophyrin IX, dodecaphenylporphyrin, hematoporphyrin, hematoporphyrin IX, hematoporphyrin monomer, hematoporphyrin dimer, hematoporphyrin derivative, hematoporphyrin derivative A, hematoporphyrin IX dihydrochloride, hematoporphyrin dihydrochloride, mesoporphyrin, mesoporphyrin IX, monohydroxyethylvinyl deuteroporphyrin, 5,10,15,20-tetra(o-hydroxyphenyl) porphyrin, 5,10,15,20-tetra(m-hydroxyphenyl)porphyrin, 5,10,15,20-tetra(p-hydroxyphenyl) porphyrin, 5,10,15,20-tetrakis(3-methoxyphenyl)-porphyrin, 5,10,15,20-tetrakis(3,4-dimethoxyphenyl)porphyrin, 5,10,15,20-tetrakis(3,5-dimethoxyphenyl)porphyrin, 5,10,15,20-tetrakis(3,4,5-trimethoxyphenyl)porphyrin, 2,3,7,8,12,13,17,18-octaethyl-5,10,15,20-tetraphenylporphyrin, porphyrin c, protoporphyrin, protoporphyrin IX, tetra-(4-N-carboxyphenyl)-porphine, tetra-(3-methoxyphenyl)-porphine, tetra-(3-methoxy-2,4-difluorophenyl)-porphine, 5,10,15,20-tetrakis (4-N-methylpyridyl)porphine, tetra-(4-N-methylpyridyl)-porphine tetrachloride, tetra-(3-N-methylpyridyl)-porphine, tetra-(2-N-methylpyridyl)-porphine, tetra(4-N,N,N-trimethylanilinium)porphine, tetra-(4-N,N,N'''-trimethylamino-phenyl)porphine tetrachloride, tetranaphthaloporphyrin, tetraphenylporphyrin, tetra-(4-sulfonatophenyl)-porphine, 4-sulfonatophenylporphine, uroporphyrin, uroporphyrin III, uroporphyrin IX, and uroporphyrin I, and esters thereof.

16. The method of claim 15, wherein the porphyrin compound is selected from the group consisting of coproporphyrin III, coproporphyrin III tetramethylester, deuteroporphyrin, deuteroporphyrin DC dichloride, deuteroporphyrin IX dimethylester, hematoporphyrin, hematoporphyrin DC, hematoporphyrin derivative, hematoporphyrin derivative A, hematoporphyrin IX dihydrochloride, hematoporphyrin dihydrochloride, hematoporphyrin IX dimethylester, mesoporphyrin, mesoporphyrin dimethylester, mesoporphyrin IX, mesoporphyrin IX dimethylester, protoporphyrin, protoporphyrin DC, protoporphyrin dimethylester, protoporphyrin IX dimethylester, uroporphyrin, uroporphyrin III, uroporphyrin IX, and uroporphyrin I.

17. The method of claim 16, wherein the porphyrin compound is selected from the group consisting of protoporphyrin IX, deuteroporphyrin IX dichloride, deuteroporphyrin IX dimethylester, hematoporphyrin, hematoporphyrin DC, hematoporphyrin derivative, mesoporphyrin dimethylester, mesoporphyrin IX, and mesoporphyrin IX dimethylester.

18. The method of claim 17, wherein the porphyrin compound is protoporphyrin IX.

19. The method of claim 1, wherein:
$B^1$ and $B^2$ are each independently selected from the group consisting of $CF_3$, $CCl_3$, $NR^3_3{}^+$, $NO_2$, CN, $C(=O)R^4$, $C(=O)OR^1$, $SO_2R^5$, aryl, and —C=$CHR^6$;
$D^1$ and $D^2$ are each independently selected from the group consisting of F, Cl, Br, I, $CF_3$, $CCl_3$, $NR^3_3{}^+$, $NO_2$, CN, $C(=O)R^4$, $C(=O)OR^1$, $SO_2R^5$, aryl, and —C=$CHR^6$;
each m independently is 0, 1, or 2;
n is 0 or 1;
each $R^1$ is independently selected from the group consisting of H, alkyl, alkenyl, alkynyl, and aryl;
$R^2$ is selected from the group consisting of H, alkyl, cycloalkyl, alkenyl, alkynyl, and aryl;
each $R^3$ is independently selected from the group consisting of H and $C_1$-$C_6$ alkyl;
each $R^4$ is independently selected from the group consisting of H, alkyl, alkenyl, alkynyl, and aryl;
each $R^5$ is independently selected from the group consisting of H, O$^-$, OH, $NH_2$, and Cl; and,
each $R^6$ is independently selected from the group consisting of alkyl, alkenyl, alkynyl, and aryl.

20. The method of claim 19, wherein:
B$^1$ and B$^2$ are each independently selected from the group consisting of CN, C(=O)R$^4$, C(=O)OR$^1$, SO$_2$R$^5$;
D$^1$ and D$^2$ are each independently selected from the group consisting of F, Cl, Br, CF$_3$, CCl$_3$, NR$^3{}_3{}^+$, NO$_2$, CN, C(=O)R$^4$, C(=O)OR$^1$, and SO$_2$R$^5$;
each m independently is 0, 1, or 2;
each R$^1$ is independently selected from the group consisting of H, C$_1$-C$_{20}$ alkyl, C$_1$-C$_{20}$ alkenyl, C$_1$-C$_{20}$ alkynyl, and aryl;
R$^2$ is selected from the group consisting of H, alkyl, cycloalkyl, alkenyl, alkynyl, and aryl;
each R$^3$ is independently selected from the group consisting of H and C$_1$-C$_4$ alkyl;
each R$^4$ is independently selected from the group consisting of H, C$_1$-C$_{20}$ alkyl, C$_1$-C$_{20}$ alkenyl, C$_1$-C$_{20}$ alkynyl, and aryl; and,
each R$^5$ is independently selected from the group consisting of H, O$^-$, OH, NH$_2$, and Cl.

21. The method of claim 1, wherein the conjugated fused tricyclic compound having electron withdrawing groups of Formula (II) is selected from the group consisting of:

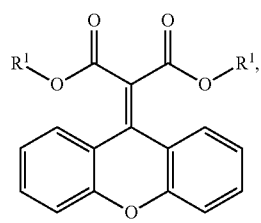
Formula IIi

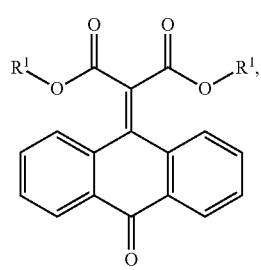
Formula IIj

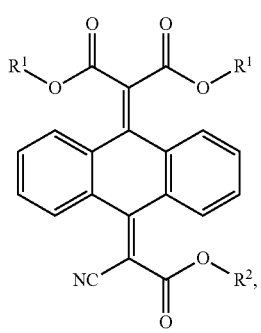
Formula IIk

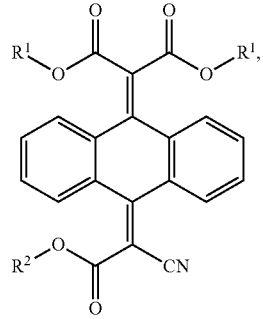
Formula IIl

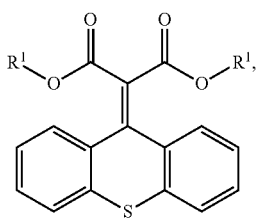
Formula IIm

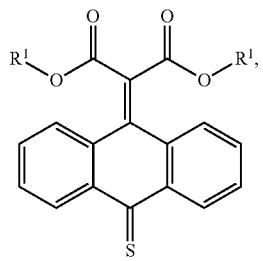
Formula IIn and mixtures thereof.

22. The method of claim 21, wherein R$^1$ and R$^2$ are each independently H, C$_1$-C$_{20}$ alkyl.

23. The method of claim 22, wherein R$^1$ and R$^2$ are each independently H, C$_1$-C$_{10}$ alkyl.

24. The method of claim 23, wherein R$^1$ and R$^2$ are each independently H, methyl, ethyl, propyl, butyl, pentyl, hexyl, heptyl, octyl, nonyl, or decyl.

25. The method of claim 24, wherein R$^1$ and R$^2$ are each independently H, methyl, ethyl, propyl, isopropyl, n-butyl, sec-butyl, isobutyl, tert-butyl, or 2-ethylhexyl.

26. The method of claim 24, wherein the compound of Formula (II) is selected from the group consisting of:

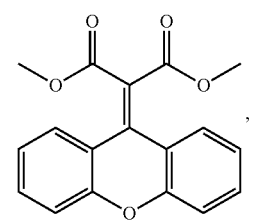
Formula IIii

51

-continued

Formula IIji
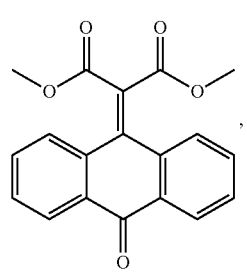

Formula IIki
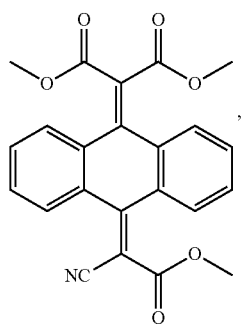

Formula IIli
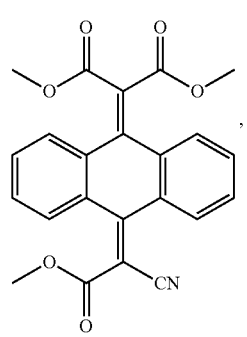

Formula IImi
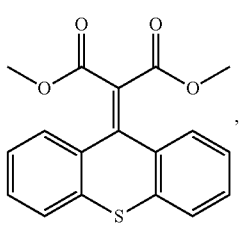

Formula IIni
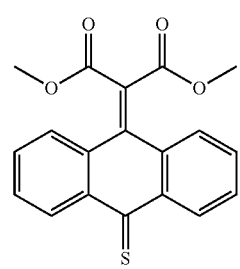

and mixtures thereof.

27. A cosmetic or dermatological composition for coating a skin surface to protect the skin from getting damaging amounts of photogenerated reactive oxygen species when skin cell-contained or blood-contained pigments are exposed to sunlight, or other visible light comprising a cosmetically acceptable carrier, and a compound of Formula IIh, IIi, IIj, IIk, IIl, IIm, IIn or a combination thereof:

52

Formula IIh
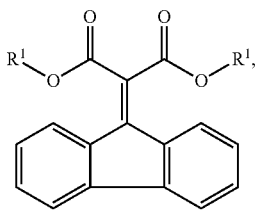

Formula IIi
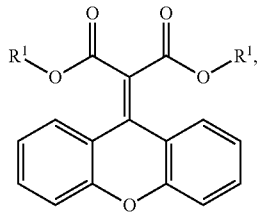

Formula IIj
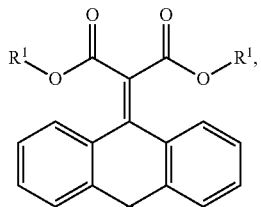

Formula IIk
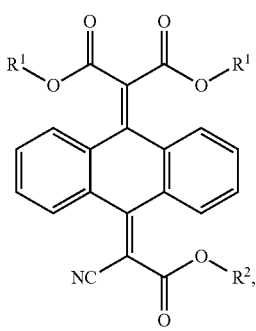

Formula IIl
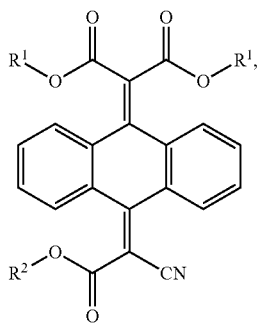

Formula IIm
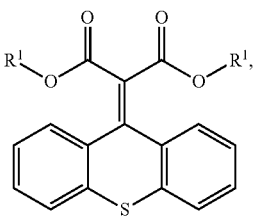

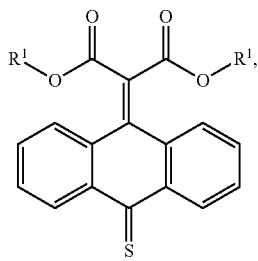

Formula IIn and mixtures thereof,
wherein:
each $R^1$ is independently selected from the group consisting of H, alkyl, alkenyl, alkynyl, cycloalkyl, cycloalkenyl, and aryl; and,
$R^2$ is selected from the group consisting of H, alkyl, cycloalkyl, alkenyl, alkynyl, and aryl.

28. The cosmetic or dermatological composition of claim 27, wherein the compound of Formula IIb, IIc, IId, IIe, IIf, IIg, IIh, IIi, IIk, III, IIm, IIn, or a combination thereof, is present in an amount of about 0.01% by weight to about 20% by weight, based on the total weight of the composition.

29. The cosmetic or dermatological composition of claim 27 further comprising an additional photoactive compound selected from the group consisting of p-aminobenzoic acid and salts and derivatives thereof; anthranilate and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naptholsulfonate and salts and derivatives thereof; benzalacetophenone naphtholsulfonate and salts and derivatives thereof; dihydroxy-naphthoic acid and salts thereof; o-hydroxydiphenyldisulfonate and salts and derivatives thereof; p-hydroxydiphenyldisulfonate and salts and derivatives thereof; coumarin and derivatives thereof; di azole derivatives; quinine derivatives and salts thereof; quinoline derivatives; hydroxyl-substituted benzophenone derivatives; naphthalate derivatives; methoxy-substituted benzophenone derivatives; uric acid derivatives; vilouric acid derivatives; tannic acid and derivatives thereof; hydroquinone; benzophenone derivatives; 1,3,5-triazine derivatives; phenyldibenzimidazole tetrasulfonate and salts and derivatives thereof; terephthalyidene dicamphor sulfonic acid and salts and derivatives thereof; methylene bis-benzotriazolyl tetramethylbutylphenol and salts and derivatives thereof; bis-ethylhexyloxyphenol methoxyphenyl triazine and salts, diethylamino hydroxyl benzoyl and derivatives thereof; and combinations of the foregoing.

30. A method of quenching excited state energy from a pigment that has been excited by absorption of light having a wavelength in the wavelength range of 290-800 nm, comprising reacting a pigment with a conjugated fused tricyclic compound having electron withdrawing groups of Formula (II-2) or a salt thereof:

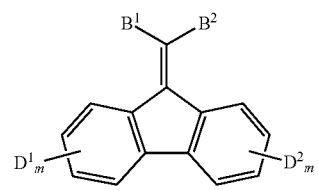

(II-2)

wherein:
$B^1$, $B^2$, $D^1$, and $D^2$ are each independently selected from the group consisting of F, Cl, Br, I, $CF_3$, $CCl_3$, $NR^2_3{}^+$, $NO_2$, CN, $C(=O)R^3$, $C(=O)OR^1$, $SO_2R^4$, aryl, and —C=$CHR^5$;
each m independently is 0, 1, 2, 3, or 4;
each R' is independently selected from the group consisting of H, alkyl, alkenyl, alkynyl, cycloalkyl, cycloalkenyl, and aryl;
each $R^2$ is independently selected from the group consisting of H and $C_1$-$C_6$ alkyl;
each $R^3$ is independently selected from the group consisting of H, alkyl, alkenyl, alkynyl, cycloalkyl, cycloalkenyl, and aryl;
each $R^4$ is independently selected from the group consisting of H, $O^-$, OH, $NH_2$, and Cl; and,
each $R^5$ is independently selected from the group consisting of alkyl, alkenyl, alkynyl, cycloalkyl, cycloalkenyl, and aryl,
wherein if $B_1$ CN, and $B_2$=$C(=O)OR^1$, then $R^1 \neq$ alkyl or cycloalkyl,
Wherein if $B_1$=CN, then $B_2 \neq$ CN, and
wherein if $B_1$=$C(=O)OR^1$, and $B_2$=$C(=O)OR^1$, then $R^1 \neq$ alkyl or cycloalkyl.

31. The method of claim 21, further comprising reacting the pigment with a conjugated fused tricyclic compound according to Formula (II) selected from the group consisting of:

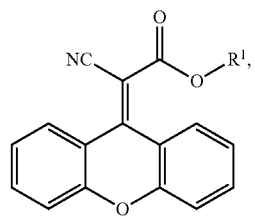

Formula IIb

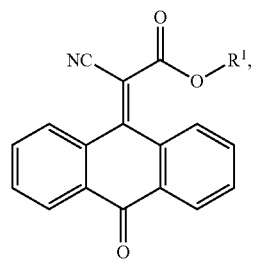

Formula IIc

Formula IId

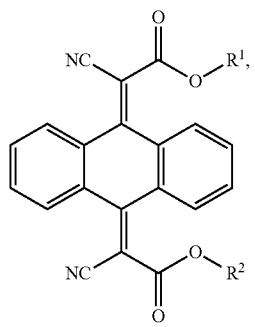

Formula IIe

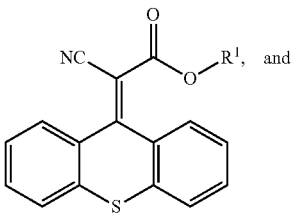

Formula IIf

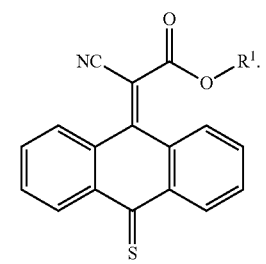

Formula IIg

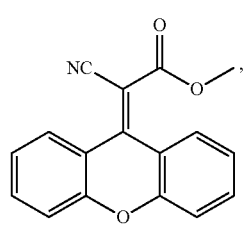

32. The method of claim 26, further comprising reacting the pigment with a conjugated fused tricyclic compound according to Formula (II) selected from the group consisting of:

Formula IIbi

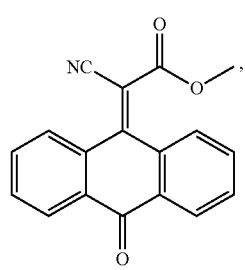

Formula IIci

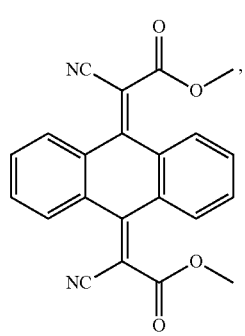

Formula IIdi

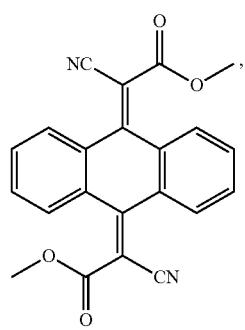

Formula IIei

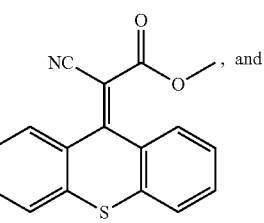

Formula IIfi, and

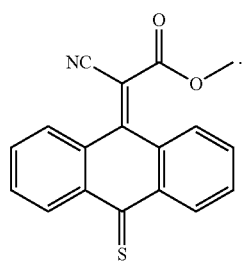

Formula IIgi

33. A cosmetic or dermatological composition according to claim 27, further comprising a compound according to Formula (II) selected from the group consisting of IIb, IIc, IId, IIe, IIf, and IIg:

Formula IIb
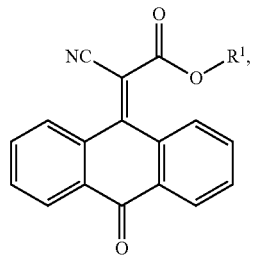
Formula IIc
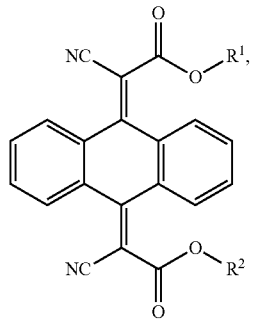
Formula IId
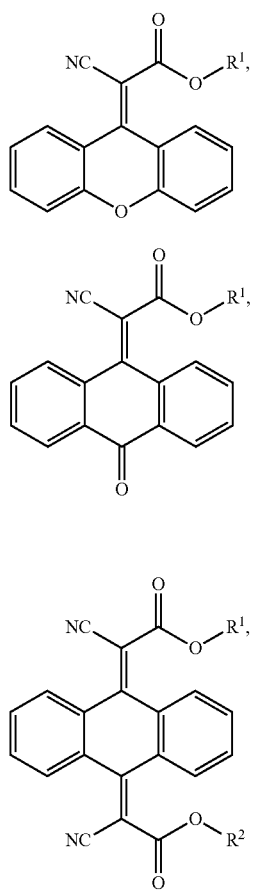
Formula IIe
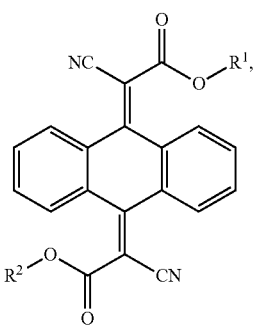
Formula IIf
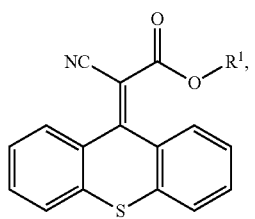
Formula IIg
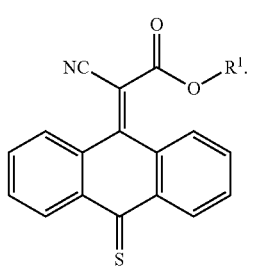
* * * * *